(12) United States Patent
Liu et al.

(10) Patent No.: US 7,341,850 B2
(45) Date of Patent: Mar. 11, 2008

(54) HUMAN LXRα VARIANTS

(75) Inventors: Qiang-Yuan Liu, West Chester, PA (US); Ponnal Nambi, Berwyn, PA (US)

(73) Assignee: Wyeth, Madison, NJ (US)

( * ) Notice: Subject to any disclaimer, the term of this patent is extended or adjusted under 35 U.S.C. 154(b) by 84 days.

(21) Appl. No.: 10/921,023

(22) Filed: Aug. 18, 2004

(65) Prior Publication Data
US 2005/0095677 A1 May 5, 2005

Related U.S. Application Data

(60) Provisional application No. 60/496,007, filed on Aug. 18, 2003.

(51) Int. Cl.
C12P 21/06 (2006.01)
(52) U.S. Cl. .................................................. 435/69.1
(58) Field of Classification Search ................ 530/350; 435/69.1
See application file for complete search history.

(56) References Cited

U.S. PATENT DOCUMENTS

| 6,500,938 B1 * | 12/2002 | Au-Young et al. ......... 536/23.1 |
| 2003/0073623 A1 | 4/2003 | Drmanac et al. | |

FOREIGN PATENT DOCUMENTS

| EP | 1 371 662 A1 | 12/2003 |
| WO | WO 96/21726 | 7/1996 |
| WO | WO 01/57276 A2 | 8/2001 |
| WO | WO 0157272 A2 * | 9/2001 |
| WO | WO 0157277 A2 * | 9/2001 |
| WO | WO 01/86003 A2 | 11/2001 |
| WO | WO 02/077229 A2 | 10/2002 |
| WO | WO 03/016475 A2 | 2/2003 |
| WO | WO 03/059884 A1 | 7/2003 |
| WO | WO 03/060078 A2 | 7/2003 |
| WO | WO 2004/011604 A2 | 2/2004 |
| WO | WO 2004/023973 A2 | 3/2004 |

OTHER PUBLICATIONS

GenCore vesrion 5.1.6, pp. 1-2 for SEQ ID No. 16.*
GenCore version 5.1.6, pp. 1-2 for SEQ ID No. 17.*
SCORE Search Results for SEQ ID No. 3, pp. 1-14.*
Database Genseq XP-002308605,"Human diagnostic and therapeutic polynucleotide Seq ID No. 577", accession No. ACN41702.
Database Geneseq XP002308608, "Human protein Q13133, Seq ID No. 8105", accession No. ADE62176.
Database EMBL XP-002319711, EPO proteins, "Sequence 34095 from Patent WO0186003", CQ 322990.
Database EMBL XP-002319712, "*Homo sapiens* nuclear receptor subfamily 1, group H, member 3, mRNA (cDNA clone MGC:10474 Image:3957848), complete cds", accession No. BC008819.
Database Genseq XP-002319713, "Human bone marrow expressed probe encoded protein SEQ ID No. 34898", accession No. AAM74592.
Database EMBL XP-002319714, "Human diagnostic and therapeutic polynucleotide Seq. ID No. 576", accession No. ACN41702.
Database EMBL XP-002319715, "7a55f01.x1 NCI_CGAP_GC6 *Homo sapiens* cDNA clone Image: 32226493' similar to TR:Q13133 Q13133 Nuclear orphan receptor LXR-alpha; mRNA sequence", accession No. BE671656.
Database Genseq XP-002319716, "Human genome-derived single exon probe from lung Seq ID No. 8759," accession No. ABS08768.
Database EMBL XP-002319717,"Sequence 8516 from Patent WO0157276", accession No. CQ138494.
Database EMBL XP-002319718, "*Homo sapiens* chromosome 11, clone RP11-17G12, complete sequence", accession No. ACO18410.
Edwards et al., "LXRs: Oxysterol-activated nuclear receptors that regulate genes controlling lipid homeostasis", Vasc. Pharmacol. 38: 249-256 (2002).
Frias et al., "A major isoform of the maize plasma membrane $H^+$-ATPase: characterization and induction by auxin in coleoptiles", 8:1533-1544 (1996).
Peet et al., "The LXRs: a new class of oxysterol receptors," 8:571-575 (1998).
Willy et al., "LXR, a nuclear receptor that defines a distinct retinoid response pathway," Genes & Development 9:1033-1045 (1995).
Written Opinion of the International Searching Authority and International Search Report.

* cited by examiner

*Primary Examiner*—Karen Cochrane Carlson
*Assistant Examiner*—Agnes B. Rooke
(74) *Attorney, Agent, or Firm*—Wilmer Cutler Pickering Hale and Dorr LLP

(57) ABSTRACT

This invention provides novel human LXRα variant polypeptides and nucleic acids encoding such polypeptides. This invention also provides the therapeutic, diagnostic, and research utilities as well as the production of such polynucleotides and polypeptides. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims. 37 CFR 1.72(b).

21 Claims, 16 Drawing Sheets

```
801  gatagttgactttgctaaacagctacccggcttcctgcagctcagccggg  850
     ||||||||||||||||||||||||||||||||||||||||||||||||||
801  gatagttgactttgctaaacagctacccggcttcctgcagctcagccggg  850

851  aggaccagattgccctgcgaagacctctgcgatcg..............  886
     ||||||||||||||||||||||||||||||||||
851  aggaccagattgccctgcgaagacctctgcgatcgaggtggctggagaa  900 (SEQ ID NO : 25)

887  ..............................aggtgatgcttctggagacatc  908
                                   ||||||||||||||||||||||
1051 cccgtttgaggtttgctgtgtgcaggtgatgcttctggagacatc  1100

909  tcggaggtacaaccctgggagtgagagtatcacctcctcaaggattca  958 (SEQ ID NO : 24)
     ||||||||||||||||||||||||||||||||||||||||||||||||
1101 tcggaggtacaaccctgggagtgagagtatcacctcctcaaggattca  1150 (SEQ ID NO : 26)
```

FIG. 1A

251
QQRFAHFTEL AIVSVQEIVD FAKQLPGFLQ LSREDQIALL KTSAIE..... 300
QQRFAHFTEL AIVSVQEIVD FAKQLPGFLQ LSREDQIALL KTSAIEVAGE

301
......... .......... .......... RDEENRPPWK RPCSKTSPPS 350
GQGMKGEAEW DYLWEGPPDI ELGEPNLLGS RDEENRPPWK RPCSKTSPPS

351
.......... VMLLETSRRY NPGSESITFL KDFSYNREDF AKAGLQVEFI 400
PRLRFAACVQ VMLLETSRRY NPGSESITFL KDFSYNREDF AKAGLQVEFI

401
NPIFEFSRAM NELQLNDAEF ALLIAISIFS ADRPNVQDQL QVERLQHTYV (SEQ ID NO : 27) 450
NPIFEFSRAM NELQLNDAEF ALLIAISIFS ADRPNVQDQL QVERLQHTYV (SEQ ID NO : 28)

FIG. 1B

```
1001  aattcatcaacccatcttcgagttctccagggccatgaatgagctgcaa  1050
      ||||||||||||||||||||||||||||||||||||||||||||||||||
 821  aattcatcaacccatcttcgagttctccagggccatgaatgagctgcaa   870

1051  ctcaatgatgccgagtttgccttgctcattgctatcagcatctttctgc   1100
      ||||||||||||||||||||||||||||||||||||||||||||||||||
 871  ctcaatgatgccgagtttgccttgctcattgctatcagcatctttctgc   920  (SEQ ID NO : 30)

1101  ..................................agaccggcccaacgtg  1116
                                        ||||||||||||||||
1121  ccagacctgctcctcaactctcttggtgacctatagaccggcccaacgtg  1170

1117  caggaccagctccaggtggagaggctgcagcacacatatgtggaagccct  1166  (SEQ ID NO : 29)
      ||||||||||||||||||||||||||||||||||||||||||||||||||
1171  caggaccagctccaggtggagaggctgcagcacacatatgtggaagccct  1220  (SEQ ID NO : 31)
```

FIG. 2A

```
301 ETSRRYNPGSESITFLKDFSYNREDFAKAGLQVEFINPIFEFSRAMNELQ 350
    ||||||||||||||||||||||||||||||||||||||||||||||||||
301 ETSRRYNPGSESITFLKDFSYNREDFAKAGLQVEFINPIFEFSRAMNELQ 350

351 LNDAEFALLIAISIFSA................................. 367
    ||||||||||||||||||
351 LNDAEFALLIAISIFSAGVEEGQWETARDLHQGGLQVPQESVGGGGWWLG 400

368 ..........DRPNVQDQLQVERLQHTYVEALHAYVSIHHPHDRLMFPRM 407

401 RVEAFAVLF*....................................... 409 (SEQ ID NO:33)
    |||||||||
408 LMKLVSLRTLSSVHSEQVFALRLQDKKLPPLLSEIWDVHE 447 (SEQ ID NO:32)
```

FIG. 2B

```
651  cgtcgctgcccagcaacagtgtaaccggcgctccttttctgaccggcttc  700
     ||||||||||||||||||||||||||||||||||||||||||||||||||
651  cgtcgctgcccagcaacagtgtaaccggcgctccttttctgaccggcttc  700  (SEQ ID NO : 34)

701  gagtcacgccttggcccatggccaccagatccccatagccgggaggcccgt  750
     ||||||||
701  gagtcac..........................................  707  (SEQ ID NO : 41)

851  aggaccagattgccctgctgaagacctctgcgatcgaggtgatgcttctg  900  (SEQ ID NO : 35)
                                      ||||||||||||||||
708  ..............................ggtgatgcttctg  720

1051 ctcaatgatgccgagtttgccttgctcattgctatcagcatcttctctgc  1100
     ||||||||||||||||||||||||||||||||||||||||||||||||||
871  ctcaatgatgccgagtttgccttgctcattgctatcagcatcttctctgc  920  (SEQ ID NO : 36)

1101 ..............................agaccggcccaacgtg  1116
                                    ||||||||||||||||
1121 ccagacctgctcctcaactctcttggtgacctatagaccggcccaacgtg  1170

1117 caggaccagctccaggtggagaggctgcagcacacatatgtggaagccct  1166  (SEQ ID NO : 37)
     ||||||||||||||||||||||||||||||||||||||||||||||||||
1171 caggaccagctccaggtggagaggctgcagcacacatatgtggaagccct  1220  (SEQ ID NO : 38)
```

FIG. 3A

```
151 QECRLRKCRQAGMREECVLSEEQIRLKKLKRQEEEQAHATSLPPRRSSPP 200
    |||||||||||||||||||||||||||||||||||||||||||||||||
151 QECRLRKCRQAGMREECVLSEEQIRLKKLKRQEEEQAHATSLPPRRSSPP 200

201 QILPQLSPEQLGMIEKLVAAQQQCNRRSFSDRLRVTPMPMAPDPHSREAR 250
    |||||||||||||||||||||||||||||||||||
201 QILPQLSPEQLGMIEKLVAAQQQCNRRSFSDRLRVT............. 236

251 QQRFAHFTELATVSVQEIVDFAKQLPGFLQLSREDQIALLKTSAIEVMLL 300
                                                  |||
237 ..........................................VMLL 240

301 ETSRRYNPGSESITFLKDFSYNREDFAKAGLQVEFINPIFEFSRAMNELQ 350
    |||||||||||||||||||||||||||||||||||||||||||||||||
241 ETSRRYNPGSESITFLKDFSYNREDFAKAGLQVEFINPIFEFSRAMNELQ 290

351 LNDAEFALLIAISIFSA................................ 367
    ||||||||||||||||
291 LNDAEFALLIAISIFSAGVEEGQMETARDLHQGLQVPQESVGGGMWLG 340

368 ........DRPNVQDLQVERLQHTYVEALHAYVSIHHPHDRLMFPRM 407

341 RVEAFAVLF*............................... 349 (SEQ ID NO : 40)

408 LMKLVSLRILSSVHSEQVFALRLQDKKLPPLLSEIWDVHE 447 (SEQ ID NO : 39)
```

FIG. 3B

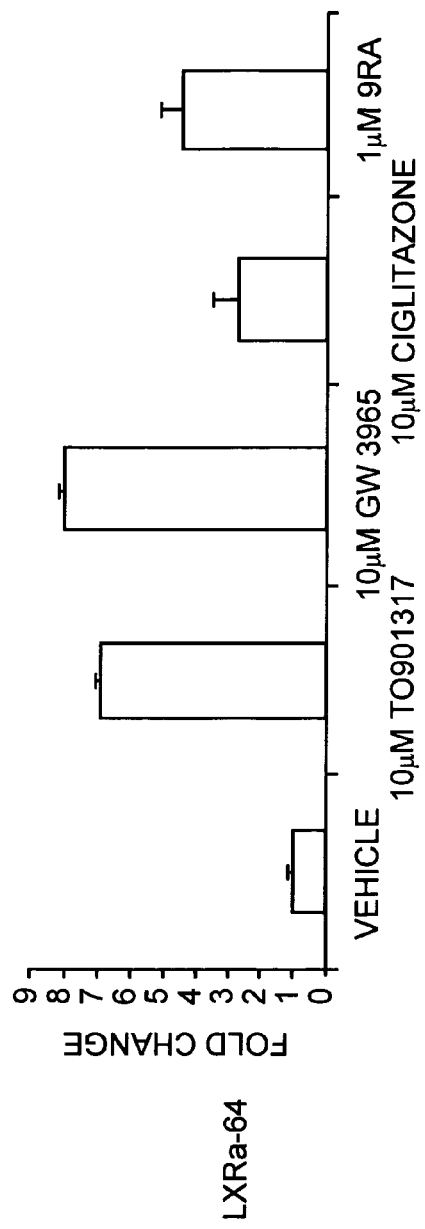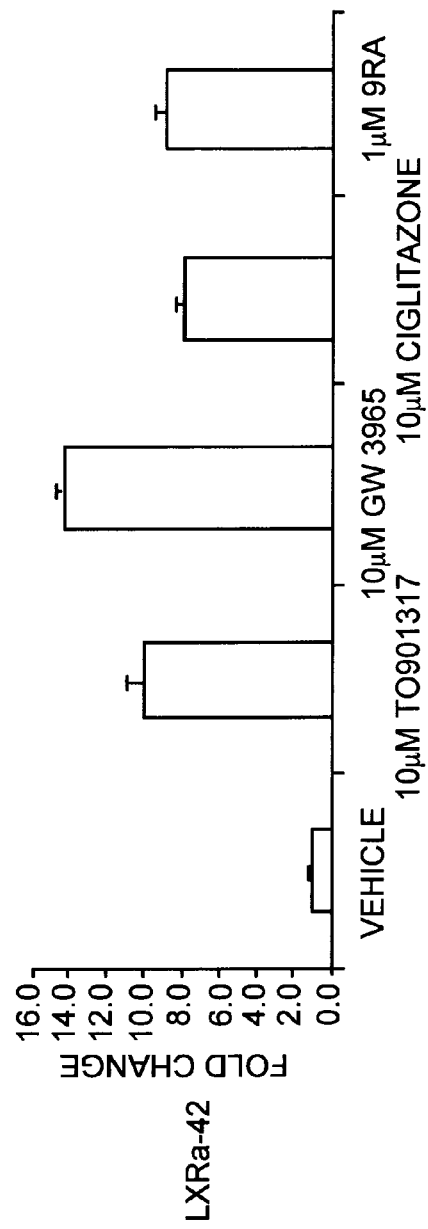

```
                        SEQUENCE LISTING

<160> NUMBER OF SEQ ID NOS: 41

<210> SEQ ID NO 1
<211> LENGTH: 1344
<212> TYPE: DNA
<213> ORGANISM: Homo sapiens

<400> SEQUENCE: 1
atgtccttgt ggctgggggc ccctgtgcct gacattcctc ctgactctgc ggtggagctg      60
tggaagccag gcgcacagga tgcaagcagc caggcccagg gaggcagcag ctgcatcctc     120
agagaggaag ccaggatgcc ccactctgct gggggtactg caggggtggg gctggaggct     180
gcagagccca cagccctgct caccagggca gagcccctt cagaacccac agagatccgt      240
ccacaaaagc ggaaaaaggg gccagccccc aaaatgctgg ggaacgagct atgcagcgtg     300
tgtggggaca aggcctcggg cttccactac aatgttctga gctgcgaggg ctgcaaggga     360
ttcttccgcc gcagcgtcat caagggagcg cactacatct gccacagtgg cggccactgc     420
cccatggaca cctacatgcg tcgcaagtgc caggagtgtc ggcttcgcaa atgccgtcag     480
gctggcatgc gggaggagtg tgtcctgtca gaagaacaga tccgcctgaa gaaactgaag     540
cggcaagagg aggaacaggc tcatgccaca tccttgcccc ccaggcgttc ctcaccccc      600 caaatcctgc cccagctcag cccggaacaa ctgggcatga tcgagaagct cgtcgctgcc     660
cagcaacagt gtaaccggcg ctcctttttct gaccggcttc gagtcacgcc ttggcccatg     720
gcaccagatc cccatagccg ggaggcccgt cagcagcgct ttgcccactt cactgagctg     780
gccatcgtct ctgtgcagga gatagttgac tttgctaaac agctacccgg cttcctgcag     840
ctcagccggg aggaccagat tgccctgctg aagacctctg cgatcgaggt gatgcttctg     900
gagacatctc ggaggtacaa ccctgggagt gagagtatca ccttcctcaa ggatttcagt     960
```

```
tataaccggg aagactttgc caaagcaggg ctgcaagtgg aattcatcaa ccccatcttc    1020
gagttctcca gggccatgaa tgagctgcaa ctcaatgatg ccgagtttgc cttgctcatt    1080
gctatcagca tcttctctgc agaccggccc aacgtgcagg accagctcca ggtggagagg    1140
ctgcagcaca catatgtgga agccctgcat gcctacgtct ccatccacca tccccatgac    1200
cgactgatgt tcccacggat gctaatgaaa ctggtgagcc tccggaccct gagcagcgtc    1260
cactcagagc aagtgtttgc actgcgtctg caggacaaaa agctcccacc gctgctctct    1320
gagatctggg atgtgcacga atga                                           1344
```

<210> SEQ ID NO 2
<211> LENGTH: 447
<212> TYPE: PRT
<213> ORGANISM: Homo sapiens

<400> SEQUENCE: 2

```
Met Ser Leu Trp Leu Gly Ala Pro Val Pro Asp Ile Pro Pro Asp Ser
 1               5                  10                  15

Ala Val Glu Leu Trp Lys Pro Gly Ala Gln Asp Ala Ser Ser Gln Ala
             20                  25                  30

Gln Gly Gly Ser Ser Cys Ile Leu Arg Glu Glu Ala Arg Met Pro His
         35                  40                  45

Ser Ala Gly Gly Thr Ala Gly Val Gly Leu Glu Ala Ala Glu Pro Thr
     50                  55                  60

Ala Leu Leu Thr Arg Ala Glu Pro Pro Ser Glu Pro Thr Glu Ile Arg
 65                  70                  75                  80

Pro Gln Lys Arg Lys Lys Gly Pro Ala Pro Lys Met Leu Gly Asn Glu
                 85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300
```

```
Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
            325                 330                 335

Asn Pro Ile Phe Glu Phe Ser Arg Ala Met Asn Glu Leu Gln Leu Asn
                340                 345                 350

Asp Ala Glu Phe Ala Leu Leu Ile Ala Ile Ser Ile Phe Ser Ala Asp
            355                 360                 365

Arg Pro Asn Val Gln Asp Gln Leu Gln Val Glu Arg Leu Gln His Thr
370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445

<210> SEQ ID NO 3
<211> LENGTH: 1536
<212> TYPE: DNA
<213> ORGANISM: Homo sapiens

<400> SEQUENCE: 3
atgtccttgt ggctgggggc ccctgtgcct gacattcctc ctgactctgc ggtggagctg      60
tggaagccag gcgcacagga tgcaagcagc caggcccagg gaggcagcag ctgcatcctc     120
agagaggaag ccaggatgcc ccactctgct gggggtactg caggggtggg gctggaggct     180
gcagagccca cagccctgct caccagggca gagccccctt cagaacccac agagatccgt     240
ccacaaaagc ggaaaaaggg gccagccccc aaaatgctgg ggaacgagct atgcagcgtg     300
tgtggggaca aggcctcggg cttccactac aatgttctga gctgcgaggg ctgcaaggga     360
ttcttccgcc gcagcgtcat caaggaggcg cactacatct gccacagtgg cggccactgc     420
cccatggaca cctacatgcg ctgcaagtgc caggagtgtc ggcttcgcaa atgccgtcag     480
gctggcatgc gggaggagtg tgtcctgtca gaagaacaga tccgcctgaa gaaactgaag     540
cggcaagagg aggaacaggc tcatgccaca tccttgcccc caggcgttc ctcacccccc     600 caaatcctgc cccagctcag cccggaacaa ctgggcatga tcgagaagct cgtcgctgcc     660
cagcaacagt gtaaccggcg ctccttttct gaccggcttc gagtcacgcc ttggcccatg     720
gcaccagatc cccatagccg ggaggcccgt cagcagcgct tgcccacttc actgagctg     780 gccatcgtct ctgtgcagga gatagttgac tttgctaaac agctacccgg cttcctgcag     840
ctcagccggg aggaccagat tgccctgctg aagacctctg cgatcgaggt ggctggagaa     900
gggcaaggga tgaagggaga agcagagtgg gattatctgt ggagggggcc tccagacatc     960
gagctggaga agccaaatct gctgggaagc agggatgagg agaatcggcc tcctggaag    1020 aggccatgct ccaagaccag ccctcctagt ccccgtttga ggtttgctgc ttgtgtgcag    1080
gtgatgcttc tggagacatc tcggaggtac aaccctggga gtgagagtat cacct tcctc    1140 aaggatttca gttataaccg ggaagacttt gccaaagcag gctgcaagt ggaattcatc    1200 aaccccatct tcgagttctc cagggccatg aatgagctgc aactcaatga tgccgagttt    1260
gccttgctca ttgctatcag catcttctct gcagaccggc ccaacgtgca ggaccagctc    1320
```

-continued

```
caggtggaga ggctgcagca cacatatgtg gaagccctgc atgcctacgt ctccatccac   1380
catccccatg accgactgat gttcccacgg atgctaatga aactggtgag cctccggacc   1440
ctgagcagcg tccactcaga gcaagtgttt gcactgcgtc tgcaggacaa aaagctccca   1500
ccgctgctct ctgagatctg ggatgtgcac gaatga                              1536
```

<210> SEQ ID NO 4
<211> LENGTH: 511
<212> TYPE: PRT
<213> ORGANISM: Homo sapiens

<400> SEQUENCE: 4

```
Met Ser Leu Trp Leu Gly Ala Pro Val Pro Asp Ile Pro Pro Asp Ser
 1               5                  10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
           100                 105                 110

Leu Ser Cys Glu Gly Cys Lys Gly Phe Phe Arg Arg Ser Val Ile Lys
       115                 120                 125

Gly Ala His Tyr Ile Cys His Ser Gly Gly His Cys Pro Met Asp Thr
   130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Ala Gly Glu Gly Gln Gly Met
    290                 295                 300

Lys Gly Glu Ala Glu Trp Asp Tyr Leu Trp Glu Gly Pro Pro Asp Ile
305                 310                 315                 320

Glu Leu Gly Glu Pro Asn Leu Leu Gly Ser Arg Asp Glu Glu Asn Arg
                325                 330                 335
```

```
Pro Pro Trp Lys Arg Pro Cys Ser Lys Thr Ser Pro Ser Pro Arg
            340                 345                 350

Leu Arg Phe Ala Ala Cys Val Gln Val Met Leu Leu Glu Thr Ser Arg
            355                 360                 365

Arg Tyr Asn Pro Gly Ser Glu Ser Ile Thr Phe Leu Lys Asp Phe Ser
            370                 375                 380

Tyr Asn Arg Glu Asp Phe Ala Lys Ala Gly Leu Gln Val Glu Phe Ile
385                 390                 395                 400

Asn Pro Ile Phe Glu Phe Ser Arg Ala Met Asn Glu Leu Gln Leu Asn
                405                 410                 415

Asp Ala Glu Phe Ala Leu Leu Ile Ala Ile Ser Ile Phe Ser Ala Asp
            420                 425                 430

Arg Pro Asn Val Gln Asp Gln Leu Gln Val Glu Arg Leu Gln His Thr
            435                 440                 445

Tyr Val Glu Ala Leu His Ala Tyr Val Ser Ile His His Pro His Asp
            450                 455                 460

Arg Leu Met Phe Pro Arg Met Leu Met Lys Leu Val Ser Leu Arg Thr
465                 470                 475                 480

Leu Ser Ser Val His Ser Glu Gln Val Phe Ala Leu Arg Leu Gln Asp
                485                 490                 495

Lys Lys Leu Pro Pro Leu Leu Ser Glu Ile Trp Asp Val His Glu
            500                 505                 510

<210> SEQ ID NO 5
<211> LENGTH: 1230
<212> TYPE: DNA
<213> ORGANISM: Homo sapiens

<400> SEQUENCE: 5
atgtccttgt ggctgggggc ccctgtgcct gacattcctc ctgactctgc ggtggagctg      60
tggaagccag gcgcacagga tgcaagcagc caggcccagg gaggcagcag ctgcatcctc     120
agagaggaag ccaggatgcc ccactctgct gggggtactg caggggtggg gctgaggct     180 gcagagccca cagccctgct caccagggca gccccctt cagaacccac agagatccgt      240
ccacaaaagc ggaaaaaggg gccagccccc aaaatgctgg ggaacgagct atgcagcgtg     300
tgtggggaca aggcctcggg cttccactac aatgttctga gctgcgaggg ctgcaaggga     360
ttcttccgcc gcagcgtcat caagggagcg cactacatct gccacagtgg cggccactgc     420
cccatggaca cctacatgcg tcgcaagtgc caggagtgtc ggcttcgcaa atgccgtcag     480
gctggcatgc gggaggagtg tgtcctgtca gaagaacaga tccgcctgaa gaaactgaag     540
cggcaagagg aggaacaggc tcatgccaca tccttgcccc caggcgttc ctcacccccc      600 caaatcctgc cccagctcag cccggaacaa ctgggcatga tcgagaagct cgtcgctgcc     660
cagcaacagt gtaaccggcg ctcctttct gaccggcttc gagtcacgcc ttggcccatg      720
gcaccagatc cccatagccg ggaggcccgt cagcagcgct ttgcccactt cactgagctg     780
gccatcgtct ctgtgcagga gatagttgac tttgctaaac agctaccgg cttcctgcag     840 ctcagccggg aggaccagat tgccctgctg aagacctctg cgatcgaggt gatgcttctg     900
gagacatctc ggaggtacaa ccctgggagt gagagtatca ccttcctcaa ggatttcagt     960
tataaccggg aagactttgc caaagcaggg ctgcaagtgg aattcatcaa ccccatcttc    1020
gagttctcca gggccatgaa tgagctgcaa ctcaatgatg ccgagtttgc cttgctcatt    1080
gctatcagca tcttctctgc aggtgtggag gaggggcaat gggaaacagc aagagactta    1140
```

```
caccaaggag ggctgcaggt cccacaggaa tcggtggggg gagggggggtg gtggcttggg    1200 agggtggagg catttgctgt gttattttag                                      1230
```

<210> SEQ ID NO 6
<211> LENGTH: 409
<212> TYPE: PRT
<213> ORGANISM: Homo sapiens

<400> SEQUENCE: 6

```
Met Ser Leu Trp Leu Gly Ala Pro Val Pro Asp Ile Pro Pro Asp Ser
 1               5                  10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350
```

Asp Ala Glu Phe Ala Leu Leu Ile Ala Ile Ser Ile Phe Ser Ala Gly
        355                 360                 365

Val Glu Glu Gly Gln Trp Glu Thr Ala Arg Asp Leu His Gln Gly Gly
    370                 375                 380

Leu Gln Val Pro Gln Glu Ser Val Gly Gly Gly Trp Trp Leu Gly
385                 390                 395                 400

Arg Val Glu Ala Phe Ala Val Leu Phe
                405

<210> SEQ ID NO 7
<211> LENGTH: 1050
<212> TYPE: DNA
<213> ORGANISM: Homo sapiens

<400> SEQUENCE: 7
atgtccttgt ggctgggggc ccctgtgcct gacattcctc ctgactctgc ggtggagctg      60
tggaagccag gcgcacagga tgcaagcagc caggcccagg gaggcagcag ctgcatcctc     120
agagaggaag ccaggatgcc ccactctgct gggggtactg caggggtggg gctggaggct     180
gcagagccca cagccctgct caccagggca gagcccccct tcagaaccca cagagatccgt     240 ccacaaaagc ggaaaaaggg gccagccccc aaaatgctgg ggaacgagct atgcagcgtg     300
tgtggggaca aggcctcggg cttccactac aatgttctga gctgcgaggg ctgcaaggga     360
ttcttccgcc gcagcgtcat caagggagcg cactacatct gccacagtgg cggccactgc     420
cccatggaca cctacatgcg tcgcaagtgc caggagtgtc ggcttcgcaa atgccgtcag     480
gctggcatgc gggaggagtg tgtcctgtca gaagaacaga tccgcctgaa gaaactgaag     540
cggcaagagg aggaacaggc tcatgccaca tccttgcccc ccaggcgttc ctcaccccc       600 caaatcctgc cccagctcag cccggaacaa ctgggcatga tcgagaagct cgtcgctgcc     660
cagcaacagt gtaaccggcg ctccttttct gaccggcttc gagtcacggt gatgcttctg     720
gagacatctc ggaggtacaa ccctgggagt gagagtatca ccttcctcaa ggatttcagt     780
tataaccggg aagactttgc caaagcaggg ctgcaagtgg aattcatcaa ccccatcttc     840
gagttctcca gggccatgaa tgagctgcaa ctcaatgatg ccgagtttgc cttgctcatt     900
gctatcagca tcttctctgc aggtgtggag gaggggcaat gggaaacagc aagagactta     960
caccaaggag ggctgcaggt cccacaggaa tcggtggggg aggggggtg gtggcttggg    1020 agggtggagg catttgctgt gttattttag                                    1050

<210> SEQ ID NO 8
<211> LENGTH: 349
<212> TYPE: PRT
<213> ORGANISM: Homo sapiens

<400> SEQUENCE: 8

Met Ser Leu Trp Leu Gly Ala Pro Val Pro Asp Ile Pro Pro Asp Ser
 1               5                  10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

```
Pro Gln Lys Arg Lys Lys Gly Pro Ala Pro Lys Met Leu Gly Asn Glu
            85                  90                  95
Leu Cys Ser Val Cys Gly Asp Lys Ala Ser Gly Phe His Tyr Asn Val
           100                 105                 110
Leu Ser Cys Glu Gly Cys Lys Gly Phe Phe Arg Arg Ser Val Ile Lys
           115                 120                 125
Gly Ala His Tyr Ile Cys His Ser Gly Gly His Cys Pro Met Asp Thr
       130                 135                 140
Tyr Met Arg Arg Lys Cys Gln Glu Cys Arg Leu Arg Lys Cys Arg Gln
145                 150                 155                 160
Ala Gly Met Arg Glu Glu Cys Val Leu Ser Glu Glu Gln Ile Arg Leu
               165                 170                 175
Lys Lys Leu Lys Arg Gln Glu Glu Gln Ala His Ala Thr Ser Leu
           180                 185                 190
Pro Pro Arg Arg Ser Ser Pro Pro Gln Ile Leu Pro Gln Leu Ser Pro
           195                 200                 205
Glu Gln Leu Gly Met Ile Glu Lys Leu Val Ala Ala Gln Gln Gln Cys
           210                 215                 220
Asn Arg Arg Ser Phe Ser Asp Arg Leu Arg Val Thr Val Met Leu Leu
225                 230                 235                 240
Glu Thr Ser Arg Arg Tyr Asn Pro Gly Ser Glu Ser Ile Thr Phe Leu
               245                 250                 255
Lys Asp Phe Ser Tyr Asn Arg Glu Asp Phe Ala Lys Ala Gly Leu Gln
               260                 265                 270
Val Glu Phe Ile Asn Pro Ile Phe Glu Phe Ser Arg Ala Met Asn Glu
           275                 280                 285
Leu Gln Leu Asn Asp Ala Glu Phe Ala Leu Leu Ile Ala Ile Ser Ile
           290                 295                 300
Phe Ser Ala Gly Val Glu Gly Gln Trp Glu Thr Ala Arg Asp Leu
305                 310                 315                 320
His Gln Gly Gly Leu Gln Val Pro Gly Glu Ser Val Gly Gly Gly
               325                 330                 335
Trp Trp Leu Gly Arg Val Glu Ala Phe Ala Val Leu Phe
               340                 345

<210> SEQ ID NO 9
<211> LENGTH: 26
<212> TYPE: DNA
<213> ORGANISM: Homo sapiens

<400> SEQUENCE: 9
cggtcgacat gtccttgtgg ctgggg                                          26

<210> SEQ ID NO 10
<211> LENGTH: 31
<212> TYPE: DNA
<213> ORGANISM: Homo sapiens

<400> SEQUENCE: 10
cagcggccgc ttcgtgcaca tcccagatct c                                    31

<210> SEQ ID NO 11
<211> LENGTH: 18
<212> TYPE: DNA
<213> ORGANISM: Homo sapiens

<400> SEQUENCE: 11
```

-continued

```
tgggaagcag ggatgagg                                              18

<210> SEQ ID NO 12
<211> LENGTH: 19
<212> TYPE: DNA
<213> ORGANISM: Homo sapiens

<400> SEQUENCE: 12
gagggctggt cttggagca                                             19

<210> SEQ ID NO 13
<211> LENGTH: 21
<212> TYPE: DNA
<213> ORGANISM: Homo sapiens

<400> SEQUENCE: 13
tcggcctccc tggaagaggc c                                          21

<210> SEQ ID NO 14
<211> LENGTH: 300
<212> TYPE: DNA
<213> ORGANISM: Homo sapiens

<400> SEQUENCE: 14
tgggaactgg agttcatagc aaaacaggaa gagccggtga gcaggaaact gggaatgggg    60 caggggtga atgaccagca gtaacctcag cagcttgcct cccacatctg gactggagca   120
tctgcagggt tctcagcctc tcccctgtag cccaccagcc ctggctgctt ccattacagc   180
acttcactgg cccaagacgc aacaagacaa gattgtcctg gactctgaca cagcaaaggg   240
actggagtga ggacatctgg gttctgatcc cagcccagcc actaactgtg tggtcttgga   300

<210> SEQ ID NO 15
<211> LENGTH: 16
<212> TYPE: DNA
<213> ORGANISM: Homo sapiens
<220> FEATURE:
<221> NAME/KEY: modified_base
<222> LOCATION: (7)..(10)
<223> OTHER INFORMATION: a, t, c, g, other or unknown

<400> SEQUENCE: 15
aggtcannnn aggtca                                                16

<210> SEQ ID NO 16
<211> LENGTH: 192
<212> TYPE: DNA
<213> ORGANISM: Homo sapiens

<400> SEQUENCE: 16
gctggagaag gcaagggat gaagggagaa gcagagtggg attatctgtg ggagggcct    60 ccagacatcg agctgggaga gccaaatctg ctgggaagca gggatgagga gaatcggcct   120
ccctggaaga ggccatgctc caagaccagc cctcctagtc cccgtttgag gtttgctgct   180
tgtgtgcagg tg                                                    192

<210> SEQ ID NO 17
<211> LENGTH: 64
<212> TYPE: PRT
<213> ORGANISM: Homo sapiens

<400> SEQUENCE: 17

Val Ala Gly Glu Gly Gln Gly Met Lys Gly Glu Ala Glu Trp Asp Tyr
```

```
                 1               5              10              15
Leu Trp Glu Gly Pro Pro Asp Ile Glu Leu Gly Glu Pro Asn Leu Leu
                    20                  25                  30

Gly Ser Arg Asp Glu Asn Arg Pro Pro Trp Lys Arg Pro Cys Ser
            35                  40                  45

Lys Thr Ser Pro Pro Ser Pro Arg Leu Arg Phe Ala Ala Cys Val Gln
            50                  55                  60
```

<210> SEQ ID NO 18
<211> LENGTH: 234
<212> TYPE: DNA
<213> ORGANISM: Homo sapiens

<400> SEQUENCE: 18

```
gtgtggagga ggggcaatgg gaaacagcaa gagacttaca ccaaggaggg ctgcaggtcc    60
cacaggaatc ggtgggggga ggggggtggt ggcttgggag ggtggaggca tttgctgtgt   120
tattttagga tgagagagct tggctggagc atgtctctat attttggttg caatttgggg   180
tatggaactg gaccctggcc agacctgctc ctcaactctc ttggtgacct atag          234
```

<210> SEQ ID NO 19
<211> LENGTH: 42
<212> TYPE: PRT
<213> ORGANISM: Homo sapiens

<400> SEQUENCE: 19

```
                 1               5              10              15
Gly Val Glu Glu Gly Gln Trp Glu Thr Ala Arg Asp Leu His Gln Gly
                    20                  25                  30

Gly Leu Gln Val Pro Gln Glu Ser Val Gly Gly Gly Trp Trp Leu
            35                  40

Gly Arg Val Glu Ala Phe Ala Val Leu Phe
```

<210> SEQ ID NO 20
<211> LENGTH: 16
<212> TYPE: DNA
<213> ORGANISM: Homo sapiens

<400> SEQUENCE: 20

```
tgaccagcag taacct                                                    16
```

<210> SEQ ID NO 21
<211> LENGTH: 20
<212> TYPE: DNA
<213> ORGANISM: Homo sapiens

<400> SEQUENCE: 21

```
ggtggaggca tttgctgtgt                                                20
```

<210> SEQ ID NO 22
<211> LENGTH: 24
<212> TYPE: DNA
<213> ORGANISM: Homo sapiens

<400> SEQUENCE: 22

```
cccaaattgc aaccaaaata taga                                           24
```

<210> SEQ ID NO 23
<211> LENGTH: 29
<212> TYPE: DNA
<213> ORGANISM: Homo sapiens -continued

<400> SEQUENCE: 23
tttaggatga gagagcttgg ctggagcat                                         29

<210> SEQ ID NO 24
<211> LENGTH: 157
<212> TYPE: DNA
<213> ORGANISM: Homo sapiens

<400> SEQUENCE: 24
gatagttgac tttgctaaac agctacccgg cttcctgcag ctcagccggg aggaccagat      60
tgccctgctg aagacctctg cgatcgaggt gatgcttctg agacatctc ggaggtacaa      120 ccctgggagt gagagtatca ccttcctcag gatttca                              157

<210> SEQ ID NO 25
<211> LENGTH: 100
<212> TYPE: DNA
<213> ORGANISM: Homo sapiens

<400> SEQUENCE: 25
gatagttgac tttgctaaac agctacccgg cttcctgcag ctcagccggg aggaccagat      60
tgccctgctg aagacctctg cgatcgaggt ggctggagaa                           100

<210> SEQ ID NO 26
<211> LENGTH: 100
<212> TYPE: DNA
<213> ORGANISM: Homo sapiens

<400> SEQUENCE: 26
ccccgtttga ggtttgctgc ttgtgtgcag gtgatgcttc tggagacatc tcggaggtac      60
aaccctggga gtgagagtat caccttcctc aaggatttca                           100

<210> SEQ ID NO 27
<211> LENGTH: 136
<212> TYPE: PRT
<213> ORGANISM: Homo sapiens

<400> SEQUENCE: 27

Gln Gln Arg Phe Ala His Phe Thr Glu Leu Ala Ile Val Ser Val Gln
  1               5                  10                  15

Glu Ile Val Asp Phe Ala Lys Gln Leu Pro Gly Phe Leu Gln Leu Ser
                 20                  25                  30

Arg Glu Asp Gln Ile Ala Leu Leu Lys Thr Ser Ala Ile Glu Val Met
             35                  40                  45

Leu Leu Glu Thr Ser Arg Arg Tyr Asn Pro Gly Ser Glu Ser Ile Thr
         50                  55                  60

Phe Leu Lys Asp Phe Ser Tyr Asn Arg Glu Asp Phe Ala Lys Ala Gly
 65                  70                  75                  80

Leu Gln Val Glu Phe Ile Asn Pro Ile Phe Glu Phe Ser Arg Ala Met
                 85                  90                  95

Asn Glu Leu Gln Leu Asn Asp Ala Glu Phe Ala Leu Leu Ile Ala Ile
                100                 105                 110

Ser Ile Phe Ser Ala Asp Arg Pro Asn Val Gln Asp Gln Leu Gln Val
            115                 120                 125

Glu Arg Leu Gln His Thr Tyr Val
        130                 135

<210> SEQ ID NO 28
<211> LENGTH: 200
<212> TYPE: PRT
<213> ORGANISM: Homo sapiens

<400> SEQUENCE: 28

```
Gln Gln Arg Phe Ala His Phe Thr Glu Leu Ala Ile Val Ser Val Gln
 1               5                  10                  15
Glu Ile Val Asp Phe Ala Lys Gln Leu Pro Gly Phe Leu Gln Leu Ser
            20                  25                  30
Arg Glu Asp Gln Ile Ala Leu Leu Lys Thr Ser Ala Ile Glu Val Ala
        35                  40                  45
Gly Glu Gly Gln Gly Met Lys Gly Glu Ala Glu Trp Asp Tyr Leu Trp
    50                  55                  60
Glu Gly Pro Pro Asp Ile Glu Leu Gly Glu Pro Asn Leu Leu Gly Ser
65                  70                  75                  80
Arg Asp Glu Glu Asn Arg Pro Pro Trp Lys Arg Pro Cys Ser Lys Thr
                85                  90                  95
Ser Pro Pro Ser Pro Arg Leu Arg Phe Ala Ala Cys Val Gln Val Met
            100                 105                 110
Leu Leu Glu Thr Ser Arg Arg Tyr Asn Pro Gly Ser Glu Ser Ile Thr
        115                 120                 125
Phe Leu Lys Asp Phe Ser Tyr Asn Arg Glu Asp Phe Ala Lys Ala Gly
    130                 135                 140
Leu Gln Val Glu Phe Ile Asn Pro Ile Phe Glu Phe Ser Arg Ala Met
145                 150                 155                 160
Asn Glu Leu Gln Leu Asn Asp Ala Glu Phe Ala Leu Leu Ile Ala Ile
                165                 170                 175
Ser Ile Phe Ser Ala Asp Arg Pro Asn Val Gln Asp Gln Leu Gln Val
            180                 185                 190
Glu Arg Leu Gln His Thr Tyr Val
        195                 200
```

<210> SEQ ID NO 29
<211> LENGTH: 166
<212> TYPE: DNA
<213> ORGANISM: Homo sapiens

<400> SEQUENCE: 29

```
aattcatcaa ccccatcttc gagttctcca gggccatgaa tgagctgcaa ctcaatgatg    60
ccgagtttgc cttgctcatt gctatcagca tcttctctgc agaccggccc aacgtgcagg   120
accagctcca ggtggagagg ctgcagcaca catatgtgga agccct                  166
```

<210> SEQ ID NO 30
<211> LENGTH: 100
<212> TYPE: DNA
<213> ORGANISM: Homo sapiens

<400> SEQUENCE: 30

```
aattcatcaa ccccatcttc gagttctcca gggccatgaa tgagctgcaa ctcaatgatg    60
ccgagtttgc cttgctcatt gctatcagca tcttctctgc                         100
```

<210> SEQ ID NO 31
<211> LENGTH: 100
<212> TYPE: DNA
<213> ORGANISM: Homo sapiens

<400> SEQUENCE: 31

```
ccagacctgc tcctcaactc tcttggtgac ctatagaccg gcccaacgtg caggaccagc    60
tccaggtgga gaggctgcag cacacatatg tggaagccct                         100
```

<210> SEQ ID NO 32
<211> LENGTH: 147
<212> TYPE: PRT
<213> ORGANISM: Homo sapiens

<400> SEQUENCE: 32

Glu Thr Ser Arg Arg Tyr Asn Pro Gly Ser Glu Ser Ile Thr Phe Leu
 1               5                  10                  15

Lys Asp Phe Ser Tyr Asn Arg Glu Asp Phe Ala Lys Ala Gly Leu Gln
                20                  25                  30

Val Glu Phe Ile Asn Pro Ile Phe Glu Phe Ser Arg Ala Met Asn Glu
            35                  40                  45

Leu Gln Leu Asn Asp Ala Glu Phe Ala Leu Leu Ile Ala Ile Ser Ile
        50                  55                  60

Phe Ser Ala Asp Arg Pro Asn Val Gln Asp Gln Leu Gln Val Glu Arg
65                  70                  75                  80

Leu Gln His Thr Tyr Val Glu Ala Leu His Ala Tyr Val Ser Ile His
                85                  90                  95

His Pro His Asp Arg Leu Met Phe Pro Arg Met Leu Met Lys Leu Val
            100                 105                 110

Ser Leu Arg Thr Leu Ser Ser Val His Ser Glu Gln Val Phe Ala Leu
        115                 120                 125

Arg Leu Gln Asp Lys Lys Leu Pro Pro Leu Leu Ser Glu Ile Trp Asp
130                 135                 140

Val His Glu
145

<210> SEQ ID NO 33
<211> LENGTH: 109
<212> TYPE: PRT
<213> ORGANISM: Homo sapiens

<400> SEQUENCE: 33

Glu Thr Ser Arg Arg Tyr Asn Pro Gly Ser Glu Ser Ile Thr Phe Leu
 1               5                  10                  15

Lys Asp Phe Ser Tyr Asn Arg Glu Asp Phe Ala Lys Ala Gly Leu Gln
                20                  25                  30

Val Glu Phe Ile Asn Pro Ile Phe Glu Phe Ser Arg Ala Met Asn Glu
            35                  40                  45

Leu Gln Leu Asn Asp Ala Glu Phe Ala Leu Leu Ile Ala Ile Ser Ile
        50                  55                  60

Phe Ser Ala Gly Val Glu Glu Gly Gln Trp Glu Thr Ala Arg Asp Leu
65                  70                  75                  80

His Gln Gly Gly Leu Gln Val Pro Gln Glu Ser Val Gly Gly Gly Gly
                85                  90                  95

Trp Trp Leu Gly Arg Val Glu Ala Phe Ala Val Leu Phe
            100                 105

<210> SEQ ID NO 34
<211> LENGTH: 100
<212> TYPE: DNA
<213> ORGANISM: Homo sapiens

<400> SEQUENCE: 34
cgtcgctgcc cagcaacagt gtaaccggcg ctccttttct gaccggcttc gagtcacgcc        60
ttggcccatg gcaccagatc cccatagccg ggaggcccgt                              100

<210> SEQ ID NO 35
<211> LENGTH: 70
<212> TYPE: DNA
<213> ORGANISM: Homo sapiens

<400> SEQUENCE: 35
cgtcgctgcc cagcaacagt gtaaccggcg ctccttttct gaccggcttc gagtcacggt        60
gatgcttctg                                                               70

<210> SEQ ID NO 36
<211> LENGTH: 50
<212> TYPE: DNA
<213> ORGANISM: Homo sapiens

<400> SEQUENCE: 36
ctcaatgatg ccgagtttgc cttgctcatt gctatcagca tcttctctgc                   50

<210> SEQ ID NO 37
<211> LENGTH: 113
<212> TYPE: DNA
<213> ORGANISM: Homo sapiens

<400> SEQUENCE: 37
ctcaatgatg ccgagtttgc cttgctcatt gctatcagca tcttctctgc agaccggccc        60
aacgtgcagg accagctcca ggtggagagg ctgcacacat atgtggaagc cct              113

<210> SEQ ID NO 38
<211> LENGTH: 100
<212> TYPE: DNA
<213> ORGANISM: Homo sapiens

<400> SEQUENCE: 38
ccagacctgc tcctcaactc tcttggtgac ctatagaccg gcccaacgtg caggaccagc        60
tccaggtgga gaggctgcag cacacatatg tggaagccct                              100

<210> SEQ ID NO 39
<211> LENGTH: 296
<212> TYPE: PRT
<213> ORGANISM: Homo sapiens

<400> SEQUENCE: 39

Gln Glu Cys Arg Leu Arg Lys Cys Arg Gln Ala Gly Met Arg Glu Glu
  1               5                  10                  15

Cys Val Leu Ser Glu Glu Gln Ile Arg Leu Lys Lys Leu Lys Arg Gln
                 20                  25                  30

Glu Glu Glu Gln Ala His Ala Thr Ser Leu Pro Pro Arg Arg Ser Ser
             35                  40                  45

Pro Pro Gln Ile Leu Pro Gln Leu Ser Pro Glu Gln Leu Gly Met Ile
         50                  55                  60

Glu Lys Leu Val Ala Ala Gln Gln Gln Cys Asn Arg Arg Ser Phe Ser
 65                  70                  75                  80

Asp Arg Leu Arg Val Thr Pro Trp Pro Met Ala Pro Asp Pro His Ser
                 85                  90                  95

Arg Glu Ala Arg Gln Gln Arg Phe Ala His Phe Thr Glu Leu Ala Ile
                100                 105                 110

Val Ser Val Gln Glu Ile Val Asp Phe Ala Lys Gln Leu Pro Gly Phe
            115                 120                 125

Leu Gln Leu Ser Arg Glu Asp Gln Ile Ala Leu Leu Lys Thr Ser Ala
        130                 135                 140

Ile Glu Val Met Leu Leu Glu Thr Ser Arg Arg Tyr Asn Pro Gly Ser
145                 150                 155                 160

Glu Ser Ile Thr Phe Leu Lys Asp Phe Ser Tyr Asn Arg Glu Asp Phe
                165                 170                 175

Ala Lys Ala Gly Leu Gln Val Glu Phe Ile Asn Pro Ile Phe Glu Phe
            180                 185                 190

Ser Arg Ala Met Asn Glu Leu Gln Leu Asn Asp Ala Glu Phe Ala Leu
        195                 200                 205

Leu Ile Ala Ser Ile Phe Ser Ala Asp Arg Pro Asn Val Gln Asp Gln
210                 215                 220

Leu Gln Val Glu Arg Leu Gln His Thr Tyr Val Glu Ala Leu His Ala
225                 230                 235                 240

Tyr Val Ser Ile His His Pro His Asp Arg Leu Met Phe Pro Arg Met
                245                 250                 255

Leu Met Lys Leu Val Ser Leu Arg Thr Leu Ser Ser Val His Ser Glu
            260                 265                 270

Gln Val Phe Ala Leu Arg Leu Gln Asp Lys Lys Leu Pro Pro Leu Leu
        275                 280                 285

Ser Glu Ile Trp Asp Val His Glu
    290                 295

<210> SEQ ID NO 40
<211> LENGTH: 199
<212> TYPE: PRT
<213> ORGANISM: Homo sapiens

<400> SEQUENCE: 40

Gln Glu Cys Arg Leu Arg Lys Cys Arg Gln Ala Gly Met Arg Glu Glu
1               5                   10                  15

Cys Val Leu Ser Glu Glu Gln Ile Arg Leu Lys Lys Leu Lys Arg Gln
            20                  25                  30

Glu Glu Glu Gln Ala His Ala Thr Ser Leu Pro Pro Arg Arg Ser Ser
        35                  40                  45

Pro Pro Gln Ile Leu Pro Gln Leu Ser Pro Glu Gln Leu Gly Met Ile
    50                  55                  60

Glu Lys Leu Val Ala Ala Gln Gln Gln Cys Asn Arg Arg Ser Phe Ser
65                  70                  75                  80

Asp Arg Leu Arg Val Thr Val Met Leu Leu Glu Thr Ser Arg Arg Tyr
                85                  90                  95

Asn Pro Gly Ser Glu Ser Ile Thr Phe Leu Lys Asp Phe Ser Tyr Asn
            100                 105                 110

Arg Glu Asp Phe Ala Lys Ala Gly Leu Gln Val Glu Phe Ile Asn Pro
        115                 120                 125

Ile Phe Glu Phe Ser Arg Ala Met Asn Glu Leu Gln Leu Asn Asp Ala
    130                 135                 140

Glu Phe Ala Leu Leu Ile Ala Ile Ser Ile Phe Ser Ala Gly Val Glu
145                 150                 155                 160

Glu Gly Gln Trp Glu Thr Ala Arg Asp Leu His Gln Gly Gly Leu Gln
                165                 170                 175

Val Pro Gln Glu Ser Val Gly Gly Gly Gly Trp Trp Leu Gly Arg Val

```
                180               185               190
Glu Ala Phe Ala Val Leu Phe
        195

<210> SEQ ID NO 41
<211> LENGTH: 50
<212> TYPE: DNA
<213> ORGANISM: Homo sapiens

<400> SEQUENCE: 41
aggaccagat tgccctgctg aagacctctg cgatcgaggt gatgcttctg              50
```

HUMAN LXRα VARIANTS

CROSS-REFERENCE TO RELATED APPLICATIONS

This application claims priority to provisional U.S. Application Ser. No. 60/496,007, filed on Aug. 18, 2003, which is herein incorporated by reference in its entirety.

FIELD OF THE INVENTION

The present invention relates to novel liver X receptors (LXR) and nucleic acid sequences encoding such receptors.

BACKGROUND OF THE INVENTION

Gene expression is regulated in eukaryotic cells by the interplay of transcription factors. Steroid hormones (e.g., glucocorticoids, mineralocorticoids, estrogens, progestins, androgens and vitamin D) were found to bind to their nuclear receptors which are transcription factors and by this means regulate expression of gene coding for specific proteins and control critical cellular activities such as differentiation, proliferation and apoptosis (Meier, Recept. Signal Transduct. Res. 1997, 17, 319-335). The liver X receptors (LXRs) are a family of transcription factors that were first identified as orphan members of the nuclear receptor superfamily. The identification of a specific class of oxidized derivatives of cholesterol as ligands for the LXRs has been crucial to helping understand the function of these receptors in vivo and first suggested their role in the regulation of lipid metabolism. LXRs, members of the nuclear receptor superfamily, include LXRα (also termed RLD-1) and ubiquitous receptor (UR, also called LXRβ). LXR-dependent pathways include but are not limited to cholesterol-7alpha-hydroxylase to increase the consumption of cholesterol via the bile acid route, expression of ABC proteins with the potential to stimulate reverse cholesterol transport and increase plasma HDL-C levels (Venkateswaran et al., J. Biol. Chem. 275, 2000, 14700-14707; Costet et al., J. Biol. Chem. 2000 275(36):28240-28245; Ordovas, Nutr. Rev. 58, 2000, 76-79, Schmitz and Kaminsky, Front. Biosci. 6, 2001, D505-D514), and/or inhibit intestinal cholesterol absorption (Mangelsdorf, XIIth International Symposium on Atherosclerosis, Stockholm, June 2000). In addition, possible cross talk between fatty acid and cholesterol metabolism mediated by liver LXR have been hypothesized (Tobin et al., Mol. Endocrinol. 14, 2000, 741-752).

In summary, ongoing research suggests that there exists complexity in LXR-dependent pathways and LXR variants may contribute to these pathways differently.

In order to understand the LXR-dependent pathways and mechanism of LXR action, it is important to isolate and characterize novel subtypes, variants, and/or isoforms of the LXR. Identification of the underlying LXR subtype, variant, or isoform responsible for a particular disease state or pathological condition can permit a more accurate means of prognosticating the LXR-related disease outcomes. Furthermore, the presence or amount of expression of such polynucleotides and/or the polypeptides encoded by such polynucleotides can be used for diagnosing associated pathological conditions, diagnosing a susceptibility to an associated pathological condition; develop gene-specific and isoform-specific therapies for diseases or disorders influenced by LXR, follow the progress of a therapy for an LXR-related disease or disorder, and/or develop new pharmaceutical drug targets.

With the recognition that these variants can be as critical to metabolic and physiologic function as proteins that are separately encoded, there is a need to identify and to characterize additional variants of the LXRα proteins. The present invention satisfies this need and provides related advantages as well.

SUMMARY OF THE INVENTION

The invention relates to the identification of nucleic acid sequences encoding novel LXRα variants (e.g., LXRα-64, LXRα-42e$^+$, and LXRα-42e$^-$) and certain activities and features of those variants. Accordingly, the invention relates to an isolated nucleic acid molecule encoding a human liver X receptor alpha (LXRα) variant polypeptide such as an isolated nucleic acid molecule encoding SEQ ID NO:4, 6, 8, 17, or 19, an isolated nucleic acid molecule encoding an amino acid sequence having at least 90% (e.g., 90%, 95%, or 99%) identity with the SEQ ID NO:4, 6, 8, 17, or 19, an isolated nucleic acid molecule that hybridizes with the isolated nucleic acid molecule of described above under hybridization conditions of 6×SSC (1 M NaCl), 50% formamide, 1% SDS at 42° C., and a wash in 1×SSC at 42° C., and a wash at 68° C., in 0.2×SSC, and 0.1% SDS; and an isolated nucleic acid molecule that is complementary to any of the LXRα variant sequences described herein. The LXRα variant nucleic acid molecule can also be a fragment of a full length LXRα variant mRNA or cDNA. In general, at least a portion of the fragment is sequence that is not found in a wild type LXRα mRNA or cDNA. In some embodiments, the isolated nucleic acid molecule consists of SEQ ID NO:3, 5, 7, 16, or 18.

In certain embodiments, the isolated nucleic acid molecule is a DNA molecule. The isolated nucleic acid molecule can be an RNA molecule, or can contain synthetic nucleotides and naturally occurring nucleotides. In some cases, the isolated nucleic acid molecule includes the nucleic acid sequence of SEQ ID NO:3, 5, 7, 16, or 18 or a fragment thereof, or can consist of the nucleic acid sequence of SEQ ID NO:3, 5, 7, 16, or 18. In certain embodiments, a nucleic acid molecule of the invention can encode a polypeptide that has LXR-responsive pathway activity, e.g., can form a dimer with a wild-type LXRα, can form a heterodimer with a retinoid X receptor (RXR) (e.g., an RXRα, RXRβ, or RXRγ), or can affect the expression or activity of an LXR-responsive pathway molecule such as expression of ABCA1 or SREBP-1C.

In another embodiment, the invention relates to a polypeptide (an LXRα variant polypeptide, e.g., an LXRα-64 polypeptide, an LXRα-42e$^+$ polypeptide, an LXRα-42e$^-$ polypeptide, or a fragment thereof) encoded by an isolated LXRα variant nucleic acid molecule described herein. In some cases, the polypeptide can form a dimer with a wild-type LXRα. In some cases, the polypeptide can form a heterodimer with an RXR (e.g., an RXRα, RXRβ or RXRγ). Formation of the heterodimer can, in certain embodiments, inhibit formation of a heterodimer between the RXR and a nuclear receptor with which the RXR naturally heterodimerizes. In this case, the formation of the heterodimer can result in modulation (e.g., a decrease or increase) of an activity associated with dimerization of the RXR and the nuclear receptor with which it naturally heterodimerizes. In another embodiment, an LXRα variant polypeptide can form a heterodimer that inhibits formation of an RXR homodimer. In some cases, the inhibition results in modulation (e.g., an increase or decrease) of an activity induced by the RXR homodimer. In certain embodiments, an LXRα variant polypeptide or fragment thereof can exhibit dominant negative activity with respect to an LXR (e.g., a wild type LXRα). In certain embodiments, the polypeptide described herein is a fragment of an LXRα variant and can exhibit at least one function of an LXRα variant, e.g., binding to an antibody that specifically binds to the LXRα variant.

Also included in the invention is a construct (e.g., a plasmid, including without limitation, pCMV/myc, pcDNA 3.1, or a derivative thereof) that includes an isolated nucleic acid molecule of an LXRα variant or a fragment thereof. The isolated nucleic acid molecule can be operatively linked to a regulatory sequence.

In another embodiment, the invention relates to a host cell comprising an isolated nucleic acid molecule as described herein (e.g., an LXRα variant or a derivative thereof) or a descendent of the cell. Also included is host cell comprising a construct described supra. The host cell can be a prokaryotic cell (e.g., an *E. coli* cell), or an eukaryotic cell such as a mammalian cell, e.g., a mouse cell, rat cell, monkey cell, or human cell (such as a human embryonic cell or other type of stem cell). Examples of host cells, without limitation include a human hepatoma cell (HepG2), a Chinese hamster ovary cell (CHO), a monkey COS-1 cell, and a human embryonic kidney cell (HEK 293). Other examples of host cells include, without limitation, a *Saccharomyces cerevisiae* cell, a *Schizosaccharomyces pombe* cell, and a *Pichia pastoris* cell.

In one aspect the invention is an isolated LXRα variant polypeptide that includes the amino acid sequence of an LXRα-64, LXRα-42e$^+$, or and LXRα-42e$^-$, e.g., the isolated polypeptide includes the amino acid sequence of SEQ ID NO:4, 6, 8, 17, 19, a naturally occurring allelic variant thereof, or a fragment thereof. The isolated polypeptide can consist of the amino acid sequence of SEQ ID NO:4, 6, 8, 17, 19, or a fragment thereof. In general, a fragment does not share homology with more than 25 contiguous amino acids of SEQ ID NO:2 (e.g., 20, 15, 10, or 5 contiguous amino acids). In certain embodiments, the isolated LXRα variant polypeptide includes heterologous amino acid sequences.

In another aspect, the invention relates to a method for detecting the presence of an LXRα variant polypeptide (e.g., an LXRα-64, LXRα-42e+, or LXRα-42e−) in a sample. The method includes contacting the sample with a compound (e.g., an antibody such as a monoclonal antibody) that selectively binds to an LXRα variant polypeptide (or a fragment thereof) and determining whether the compound binds to the polypeptide in the sample. The invention also includes a kit that includes a compound that selectively binds to an LXRα variant polypeptide (e.g., an LXRα-64, LXRα-42e+, or LXRα-42e−) and instructions for use.

An embodiment of the invention includes an antibody that specifically binds to an isolated LXRα variant polypeptide described herein (e.g., an LXRα-64, LXRα-42e+, or LXRα-42e−), or a fragment thereof. In some cases, the antibody does not bind significantly to wild type LXRα. The antibody is, in certain embodiments, a polyclonal antibody. In other embodiments, the antibody is a monoclonal antibody. The antibody can include a detectable label. Also included is a fragment of an antibody such as a Fab fragment of an antibody that specifically binds to an LXRα variant. The invention also relates to a composition that includes an antibody described herein or a fragment thereof and a pharmaceutically acceptable carrier.

An aspect of the invention includes a method of identifying a new LXRα variant nucleic acid molecule (e.g., an LXRα-64, LXRα-42e$^+$, or LXRαe−). The method includes hybridizing a sample comprising one or more nucleic acid molecules with an LXRα variant nucleic acid molecule or a fragment thereof under stringent hybridization conditions, identifying a nucleic acid molecule in the sample that hybridizes with the LXRα variant nucleic acid molecule, thereby identifying a putative LXRα variant nucleic acid molecule, and determining the sequence of the putative LXRα variant nucleic acid molecule, wherein a putative LXRα variant nucleic acid molecule having a sequence that is not identical to the sequence of an LXRα variant is a new LXRα variant nucleic acid. In some cases, the new LXRα variant nucleic acid molecule encodes a known LXRα variant polypeptide. In some cases the new LXRα variant nucleic acid molecule encodes an LXRα polypeptide that is not identical to a known LXRα variant (e.g., an LXRα-64, LXRα-42e$^+$, or LXRαe−). A new LXRα variant polypeptide can include one or more conservative substitutions compared to a known LXRα variant polypeptide.

In one aspect, the invention relates to a method of detecting expression of an LXRα variant (e.g., an LXRα-64, LXRα-42e$^+$, or LXRα-42e$^-$) in a biological sample. The method includes hybridizing the biological sample with an LXRα variant nucleic acid molecule or fragment thereof (as described herein) and determining whether the nucleic acid molecule hybridizes to a nucleic acid molecule in the sample, wherein hybridization indicates that the LXRα variant is expressed. In some embodiments, the amount of hybridization is determined (e.g., an absolute amount or a relative amount compared to a control or reference amount).

Another aspect of the invention relates to a method of decreasing RXR dimer formation in a cell. The method includes contacting the cell with an LXRα variant polypeptide (e.g., an LXRα-64, LXRα-42e$^+$, or LXRα-42e$^-$) or fragment thereof, thereby inhibiting RXR dimer formation (e.g., RXR heterodimerization is inhibited or RXR homodimerization is inhibited).

In yet another aspect the invention relates to a method of identifying an LXRα variant (e.g., an LXRα-64, LXRα-42e$^+$, or LXRα-42e$^-$) ligand. The method includes providing a sample comprising an LXRα variant polypeptide, contacting the sample with a test compound, determining whether the test compound can bind to the LXRα variant, such that a compound that can bind to the LXRα variant is an LXRα variant ligand. In some embodiments, the Kd of the ligand is less than $1\times10^6$, less than $1\times10^9$, between $1\times10^6$ and $1\times10^{12}$, between $1\times10^9$ and $1\times10^{12}$. In some cases, an RXR is present in the sample. The method can include determining whether the LXRα variant ligand can bind a wild type LXRα, e.g., determining that the LXRα variant ligand does not bind to a wild type LXRα. In some cases, the identified LXRα variant ligand has a higher affinity for an LXRα variant compared to a wild type LXRα.

An aspect of the invention relates to modulating (e.g., increasing or decreasing) the expression of an LXRα-regulated gene. The method includes modulating expression or activity of an LXRα variant (e.g., an LXRα-64, LXRα-42e$^+$, or LXRα-42e$^-$). Examples of the LXRα-regulated gene include, without limitation, an SREBP-1C (sterol regulatory binding element 1c), FAS, CYP7A1 (cholesterol 7-alpha hydroxylase), ApoE, CETP (cholesterol ester transfer protein), LPL (lipoprotein lipase), ABCA1 (ATP-binding cassette transporter-1), ABCG1, ABCG5, ABCG8, ABCG4, and PLTP (phospholipid transfer protein).

In yet another aspect, the invention relates to a method of modulating LXRα variant (e.g., an LXRα-64, LXRα-42e$^+$, or LXRα-42e$^-$) expression or activity in a subject. The method includes introducing into a subject an LXRα variant nucleic acid molecule or a fragment thereof in an amount and for a time sufficient for the LXRα variant to be expressed and modulate LXRα expression or activity. In some embodiments the LXRα variant inhibits expression or activity (e.g., induction of expression of an LXRα-dependent pathway gene) of a wild-type LXRα. In some cases, the activity is LXRα heterodimerization, e.g., ligand-stimulated heterodimerization.

In another aspect, the invention includes a method of modulating expression or activity of an RXR in a subject. The method includes introducing into a subject an LXRα variant (e.g., an LXRα-64, LXRα-42e$^+$, or LXRα-42e$^-$) nucleic acid molecule or a fragment thereof in an amount and for a time sufficient for the LXRα variant to be expressed and modulate expression or activity of the RXR. In some embodiments, heterodimerization of the RXR (e.g., heterodimerization of RXR with a PPARα, PPARγ, PPARδ, RAR, XR, or PXR) is modulated (e.g., inhibited) or homodimerization of the RXR is modulated (e.g., inhibited). The RXR can be, e.g., an RXRα, RXRβ, or RXRγ.

In yet another aspect, the invention includes a method for treating an individual having an RXR-related disease or disorder, the method comprising administering to the individual a pharmaceutically effective amount of an LXRα variant (e.g., an LXRα-64, LXRα-42e$^+$, or LXRαe-) or a fragment thereof.

The invention also relates to a pharmaceutical, composition that includes a cell that can express an LXRα variant (e.g., an LXRα-64, LXRα-42e$^+$, or LXRαe$^-$) or fragment thereof, and optionally, includes a pharmaceutically acceptable carrier; an isolated LXRα variant nucleic acid molecule or fragment thereof as described herein and a pharmaceutically acceptable carrier; or an LXRα variant (e.g., an LXRα-64, LXRα-42e$^+$, or LXRαe-) polypeptide as described herein and a pharmaceutically acceptable carrier.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE DRAWINGS AND SEQUENCE DESCRIPTIONS

The invention can be more fully understood from the following detailed description, the drawings, and sequences, which form a part of this application.

FIG. 1A depicts a sequence comparison of wild type LXRα (native) cDNA with a portion of the variant LXRα-64 cDNA (referred to in Example 2). The top line illustrates a portion of the wild type LXRα sequence and the bottom line depicts portions of the LXRα-64 sequence. The numbers represent the nucleotide position from the start codon of each cDNA sequence.

FIG. 1B depicts a sequence comparison of the predicted amino acid sequences of human LXRα (native) with LXRα-64 corresponding to the sequences in FIG. 1A. The top line depicts a portion of the native LXRα amino acid sequence and the bottom line is a portion of the LXRα-64 amino acid sequence. The numbers represent the amino acid positions in the predicted sequences. The additional sequence that is specific for the LXRα-64 variant is underlined.

FIG. 2A depicts a sequence comparison of a portion of wild type LXRα cDNA with a portion of the novel variant LXRα-42e$^+$ cDNA (referred to in Example 2). The top line depicts portions of the native LXRα sequence and the bottom line is a portion of the LXRα-42e$^+$ sequence. The numbers represent the nucleotide positions from the start codon of the cDNAs.

FIG. 2B depicts a sequence comparison of the predicted amino acid sequences of a human LXRα (wild type) with LXRα-42e$^+$. The top line is a portion of the native LXRα sequence and the bottom line is a portion of the new variant. The numbers represent the amino acid positions. Sequence that is specific for the LXRα-42e$^+$variant is underlined.

FIG. 3A depicts a sequence comparison of a portion of a wild type LXRα cDNA with a portion of the novel variant LXRα-42e$^-$ cDNA (referred to in Example 2). The top line depicts portions of the wild type LXRα sequence and the bottom line is a portion of the LXRα-42e$^-$ sequence. The numbers represent the nucleotide positions from the start codon of the cDNAs.

FIG. 3B depicts a sequence comparison of the predicted amino acid sequences of a wild type human LXRα with LXRα-42e$^-$. The top line is a portion of the wild type LXRα sequence and the bottom line is a portion of the new variant. The numbers represent the amino acid positions. Sequence that is specific for the LXRα-42e$^-$ variant is underlined.

FIG. 8A is a bar graph depicting the results of experiments assaying gene regulation of RNA expression of LXRα-64 in THP-1 cells.

FIG. 8B is a bar graph depicting the results of experiments assaying gene regulation of RNA expression of LXRα-42 in THP-1 cells.

Figure 11:
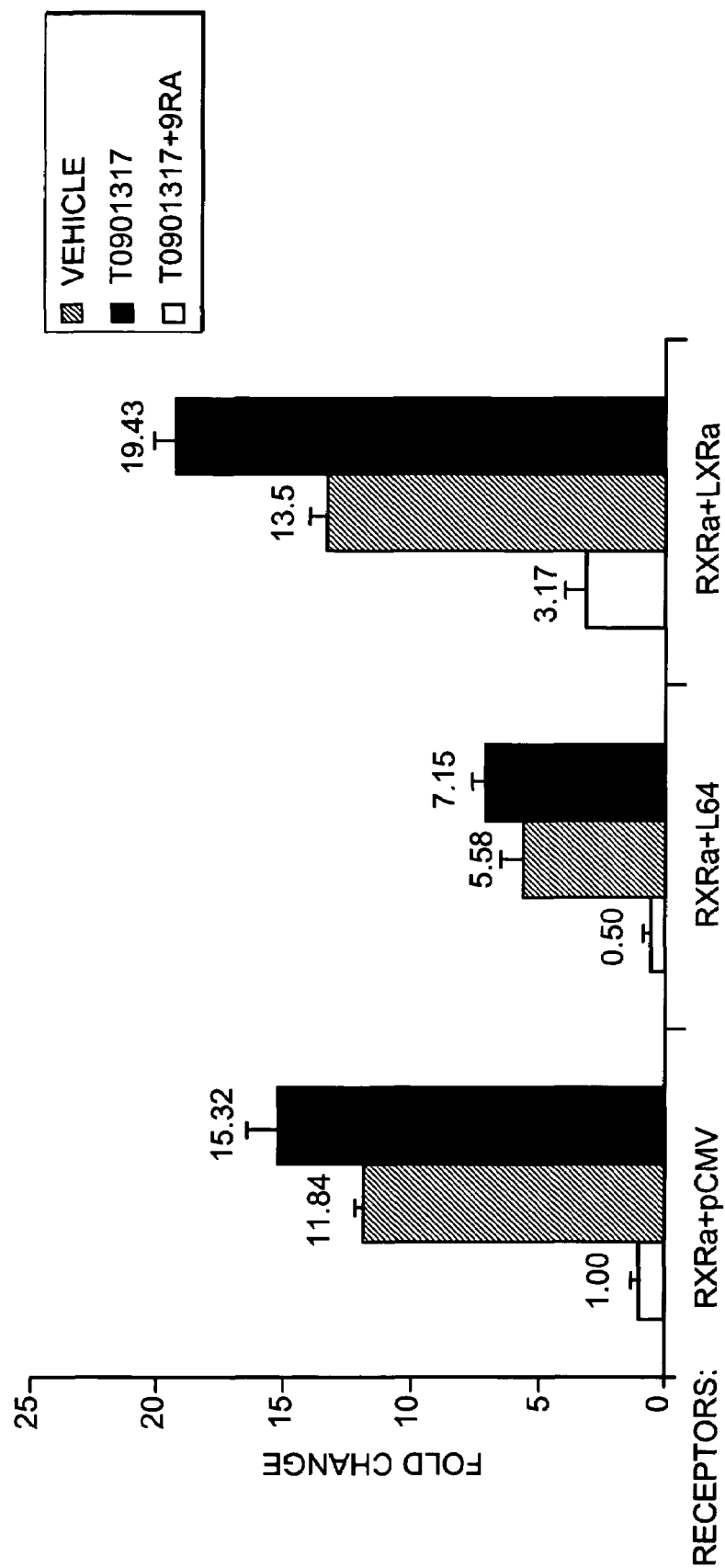

FIG. 11 is a bar graph depicting the results of experiments assaying SREBP-1C expression in HEK293 cells transfected with expression vectors encoding RXRα (RXRa), wild type LXRα (LXRa) and RXRα, or LXRα-64 (L64) and RXRα in the presence or absence of an LXRα agonist (TO901317), an RXRα agonist (9RA), or both agonists. Samples are RXRα+pCMV (control vector), RXRa+L64, RXRa+LXRa. Expression is displayed as a fold change compared to control.

Figure 12:
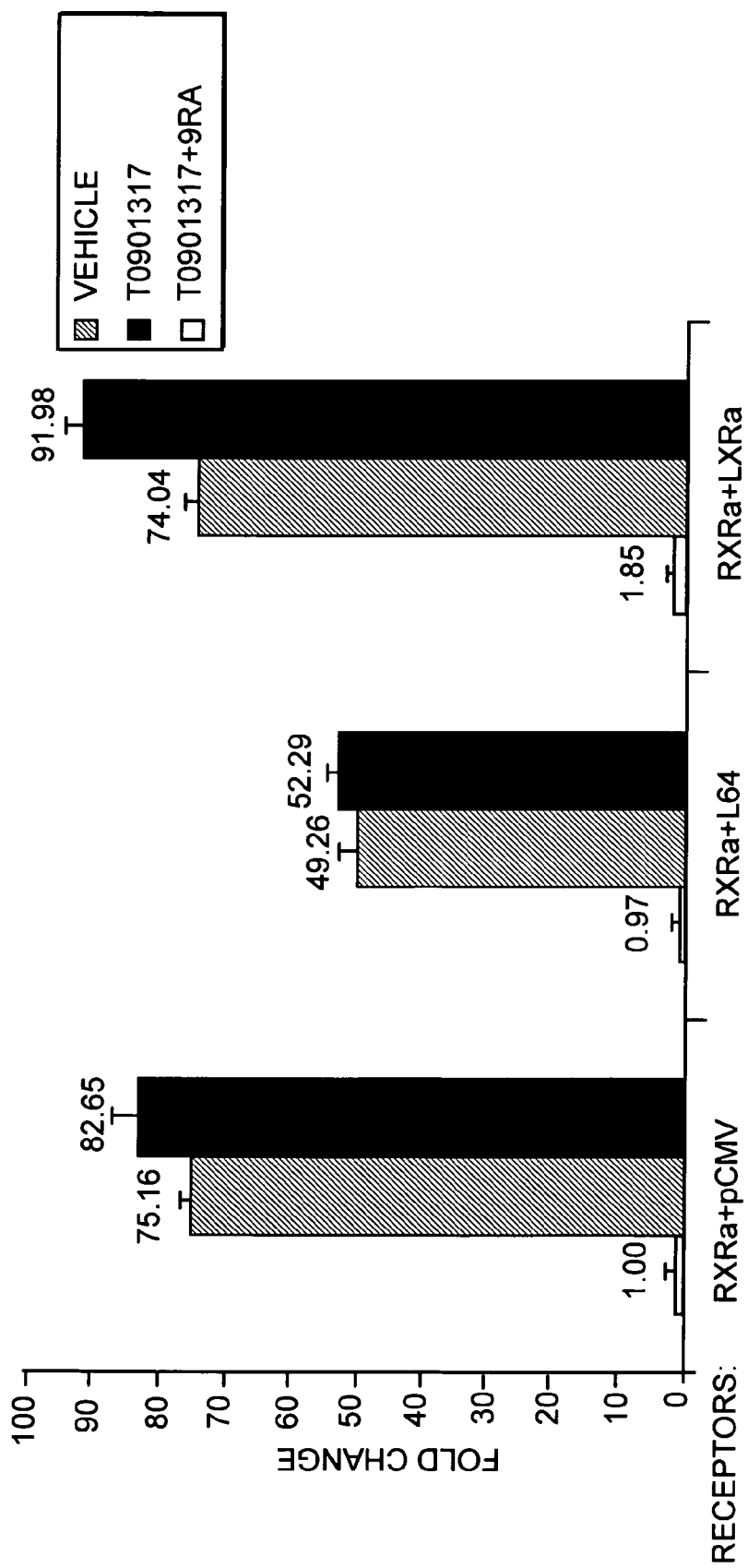

FIG. 12 is a bar graph depicting the results of experiments assaying ABCA1 expression in HEK 293 cells transfected with expression vectors encoding RXRα (RXRa), wild type LXRα (LXRa) and RXRα, or LXRα-64 (L64) and RXRα in the presence or absence of an LXRα agonist (TO901317), an RXRα agonist (9RA), or both agonists. Samples are RXRα+pCMV (control vector), RXRa+L64, RXRa+LXRa. Expression is displayed as a fold change compared to control.

A brief list of sequence descriptions is provided below and sequences are provided after the Examples and in the figures.

SEQ ID NO:1 is the nucleotide sequence that codes for the wild type LXRα.
SEQ ID NO:2 is the deduced amino acid sequence of wild type LXRα.
SEQ ID NO:3 is the nucleotide sequence that codes for the variant, LXRα-64.
SEQ ID NO:4 is the deduced amino acid sequence of variant, LXRα-64.
SEQ ID NO:5 is the nucleotide sequence that codes for the variant, LXRα-42e$^+$.
SEQ ID NO:6 is the deduced amino acid sequence of variant, LXRα-42e$^+$.
SEQ ID NO:7 is the nucleotide sequence that codes for the variant, LXRα-42e$^-$.
SEQ ID NO:8 is the deduced amino acid sequence of variant, LXRα-42e$^-$.
SEQ ID NO:9 is the nucleotide sequence of the forward primer LXRα-For.
SEQ ID NO:10 is the nucleotide sequence of the reverse primer LXRα-rev.
SEQ ID NO:11 is the nucleotide sequence of the forward primer L64-for.
SEQ ID NO:12 is the nucleotide sequence of the reverse primer L64-rev.
SEQ ID NO:13 is the nucleotide sequence of the L64 TaqMan probe.
SEQ ID NO:14 is part of LXRα promoter sequence used for the luciferase assay (referred to in Example 6)
SEQ ID NO:15 is the nucleotide sequence of the LXR response element (LXRE).
SEQ ID NO:16 is the unique nucleotide sequence of LXRα-64 variant which contains additional sequence compared to the wild type that connects exons 6 and 7 of wild type LXRα, creating a longer exon 6 in LXRα-64 variant. The new exon 6 includes all of exon 6 as described for wild-type LXRα in addition to extra sequence that is derived from sequence in intron 6 of wild type LXRα that is located between exon 6 and exon 7.
SEQ ID NO:17 is the deduced amino acid sequence encoded by SEQ ID NO:16.
SEQ ID NO:18 is the unique nucleotide sequence of LXRα-42e that combines with exon 8 of wild type LXRα to create a longer exon 8 in the LXRα-42 variant. This sequence is 234 nucleotides in length and contains a stop codon (TAG) at position 126, thus the following 108 nucleotides are untranslated. It is found in both LXRα-42e$^-$ and LXRα-42e$^+$.
SEQ ID NO:19 is the deduced amino acid sequence encoded by SEQ ID NO:18.
SEQ ID NO:20 is the nucleotide sequence of the LXRα response element (LXRE) used in the present invention.
SEQ ID NO:21 is the nucleotide sequence of the primer L42-For.
SEQ ID NO:22 is the nucleotide sequence of the primer L42-Rev.
SEQ ID NO:23 is the nucleotide sequence of an L42 probe.
SEQ ID NO:24 is a portion of the nucleotide sequence of a wild type (native) LXRα cDNA.
SEQ ID NO:25 is a portion of the nucleotide sequence of an LXRα-64 cDNA.
SEQ ID NO:26 is a portion of the nucleotide sequence of an LXRα-64 cDNA.
SEQ ID NO:27 is a portion of the amino acid sequence of a wild type LXRα cDNA.
SEQ ID NO:28 is a portion of the amino acid sequence of an LXRα-64 cDNA.
SEQ ID NO:29 is a portion of the nucleotide sequence of a wild type LXRα cDNA.
SEQ ID NO:30 is a portion of the nucleotide sequence of an LXRα-42e+ cDNA.
SEQ ID NO:31 is a portion of the nucleotide sequence of an LXRα-42e+ cDNA.
SEQ ID NO:32 is a portion of the amino acid sequence of a wild type LXRα.
SEQ ID NO:33 is a portion of the amino acid sequence of an LXRα-42e+ cDNA.
SEQ ID NO:34 is a portion of the nucleotide sequence a wild type LXRα cDNA.
SEQ ID NO:35 is a portion of the nucleotide sequence an LXRα-42e– cDNA.
SEQ ID NO:36 is a portion of the nucleotide sequence LXRα-42e– cDNA.
SEQ ID NO:37 is a portion of the nucleotide sequence a wild type LXRα cDNA.
SEQ ID NO:38 is a portion of the nucleotide sequence LXRα-42e– cDNA.
SEQ ID NO:39 is a portion of the amino acid sequence of a wild type LXRα.
SEQ ID NO:40 is a portion of the amino acid sequence of an LXRα-43e–.
SEQ ID NO:41 is a portion of the nucleotide sequence of a wild type LXRα cDNA.

DETAILED DESCRIPTION OF THE INVENTION

Applicants have succeeded in identifying and characterizing new splice variants of an LXRα gene that encode novel LXRα variants referred to herein as LXRα-64, LXRα-42e$^+$ and LXRα-42e$^-$, respectively. The newly identified sequences produce variants that differ structurally and functionally from known LXRα proteins. LXRα-64, LXRα-42e$^+$ and LXRα-42e$^-$ variants are encoded by the polynucleotide sequences of SEQ ID NO:3, SEQ ID NO:5, and SEQ ID NO:7, respectively, and represent alternative variants of the full-length LXRα cDNA.

Figure 4:
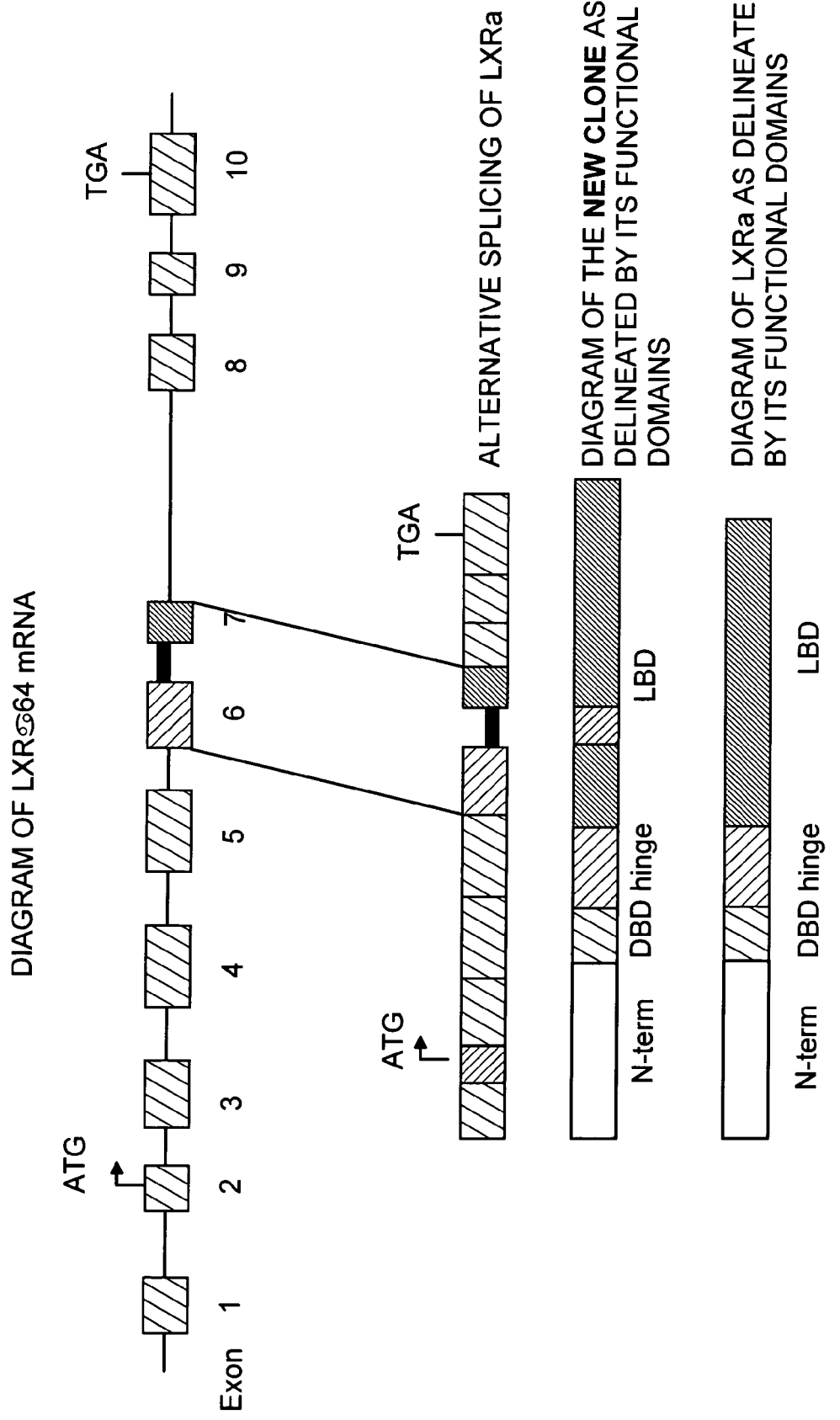
FIG. 4 is a diagrammatic representation of LXRα-64 mRNA.
Figure 5:
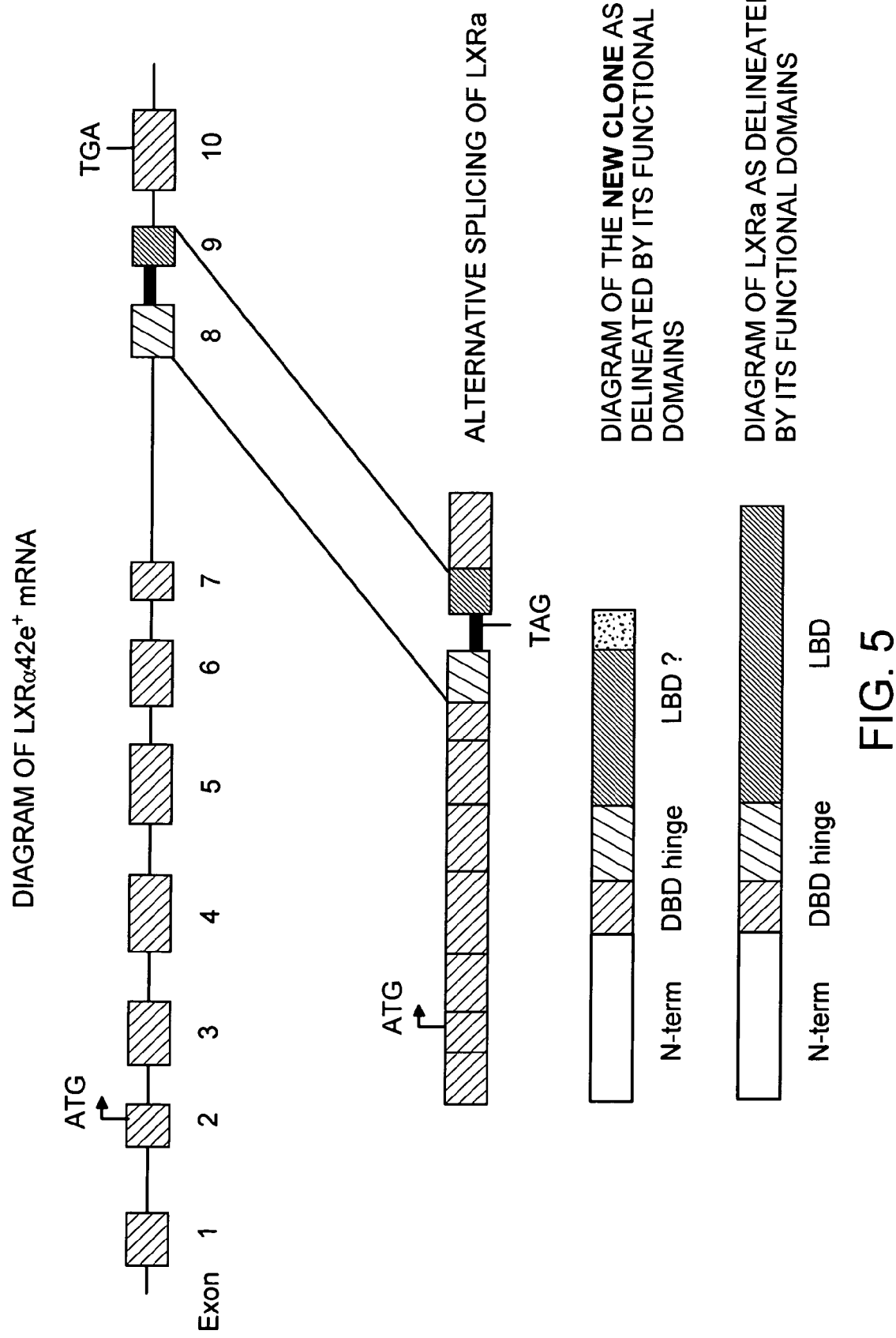
FIG. 5 is a diagrammatic representation of LXRα-42e$^+$ mRNA.
Figure 6:
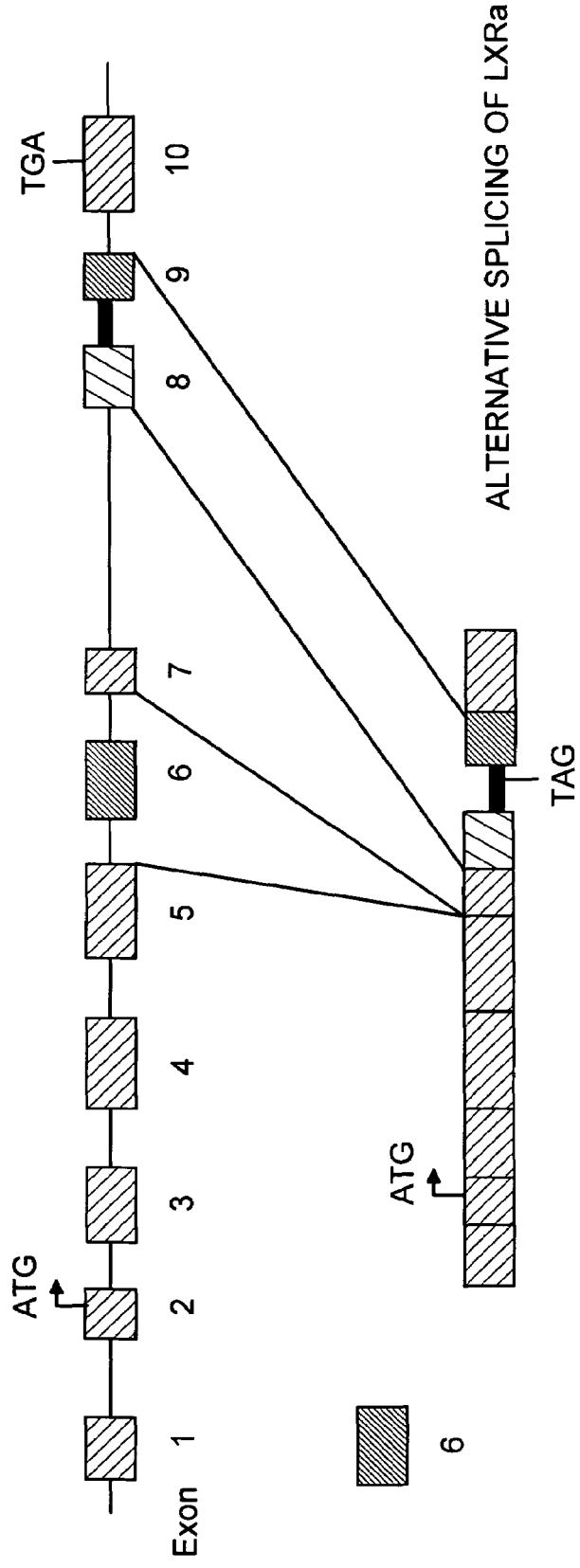
FIG. 6 is a diagrammatic representation of LXRα-42e$^-$ mRNA.
Figure 7A:
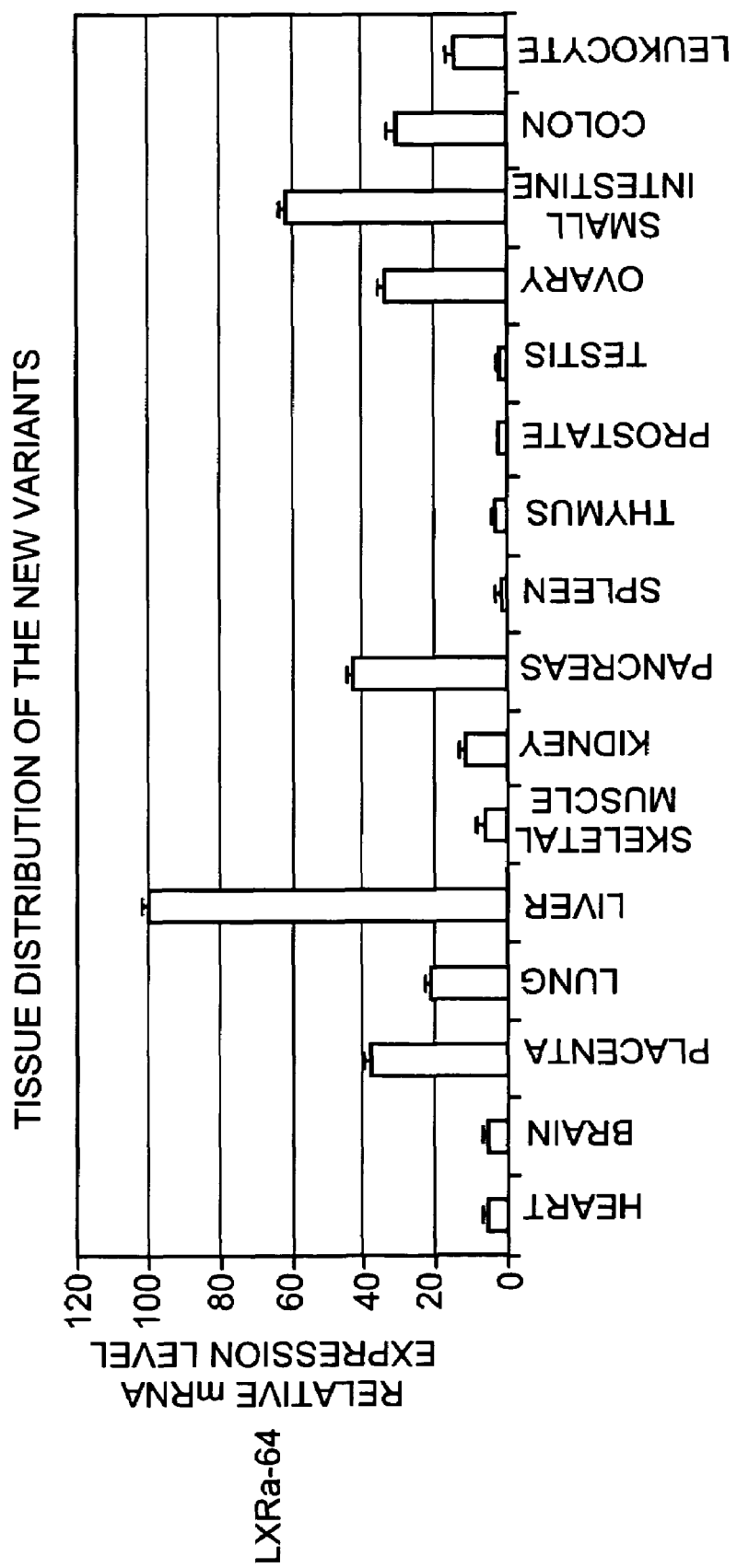
FIG. 7A is a bar graph depicting the results of experiments assaying the relative RNA expression of LXRα-64 in various tissues.
Figure 7B:
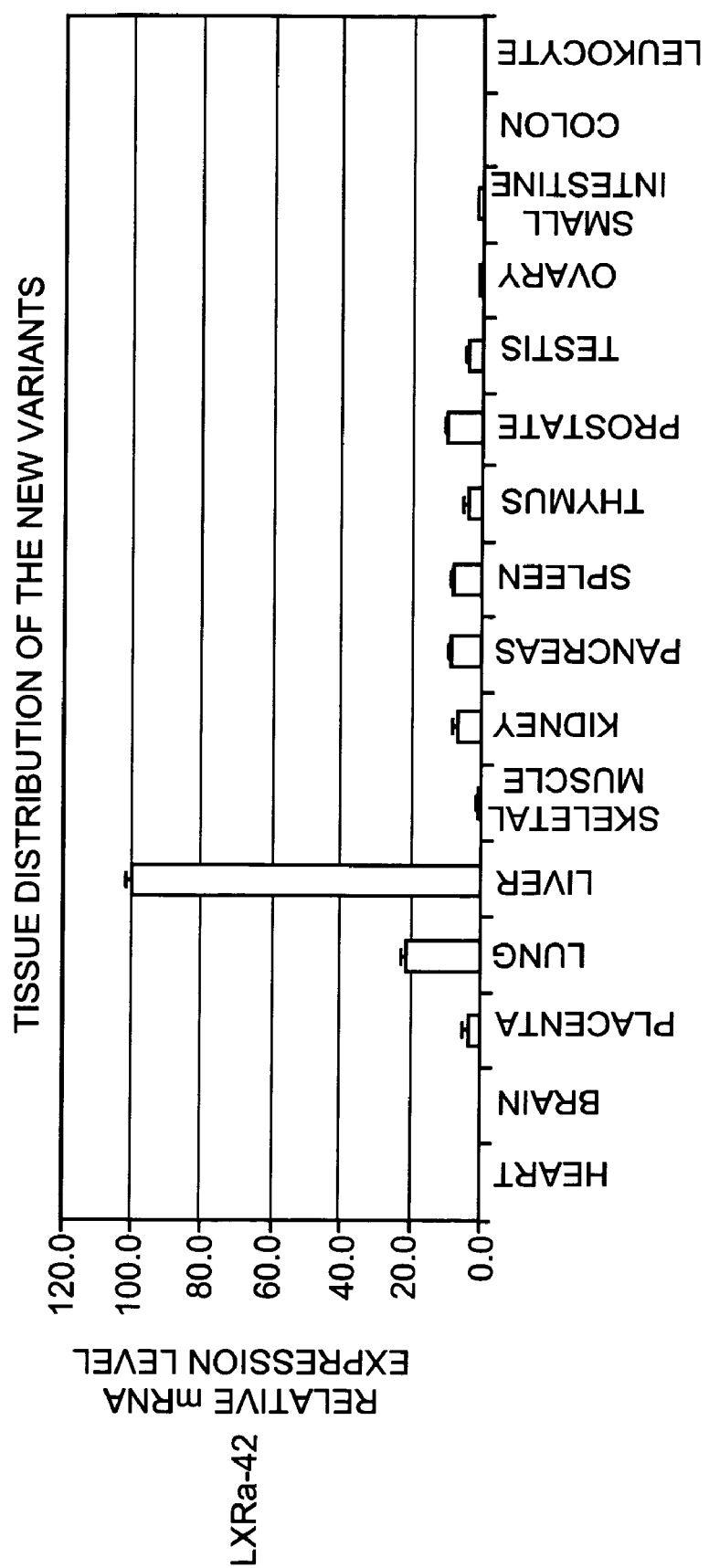
FIG. 7B is a bar graph depicting the results of experiments assaying the relative RNA expression of LXRα-42 (LXRα-42e$^+$ and LXRα-42e$^-$ combined) in various tissues.

Genomic organization analysis showed that the newly isolated variants; LXRα-64, LXRα-42e$^+$, and LXRα-42e$^-$ share certain protein domains and structural organization with wild type LXRα (FIGS. 4, 5, and 6). RT-PCR analysis revealed that the variant mRNA transcripts of the present invention are most abundant in liver (FIGS. 7A and 7B). More particularly, LXRα-64 is most highly expressed in liver, small intestine, and pancreas. LXRα-42e$^+$ and LXRα-42e$^-$ are most highly expressed in liver. There is significantly less expression in other tissues. The N-terminal, DNA binding, and hinge domains of the three LXRα subtypes are identical to the corresponding regions of wild type LXRα, whereas the C-terminal domain and the ligand binding domain (LBD) exhibit some variability. In contrast with wild type LXRα, LXRα-64 variant has an extra 64 amino acids in its ligand binding domain, LXRα-42e$^+$ has an alternative 42 amino acids starting at residue 367 of the wild type LXRα sequence and the C terminal from residue 368 to the end of the wild type LXRα (80 amino acids) is not present in this variant, and therefore lacks a portion of the ligand binding domain that is present in the wild type LXRα. LXRα-42e⁻ contains 349 amino acids and lacks 60 amino acids that are encoded by exon 6 of wild type LXRα. Starting at amino acid 237 of LXRα-42⁻, there is 100% identity for 71 amino acids with the wild type LXRα. This is followed by 42 amino acids that are completely different from wild type. Like LXRα-42+, the C-terminal of wild type LXRα is not present in LXRα-42e−.

Figure 9:
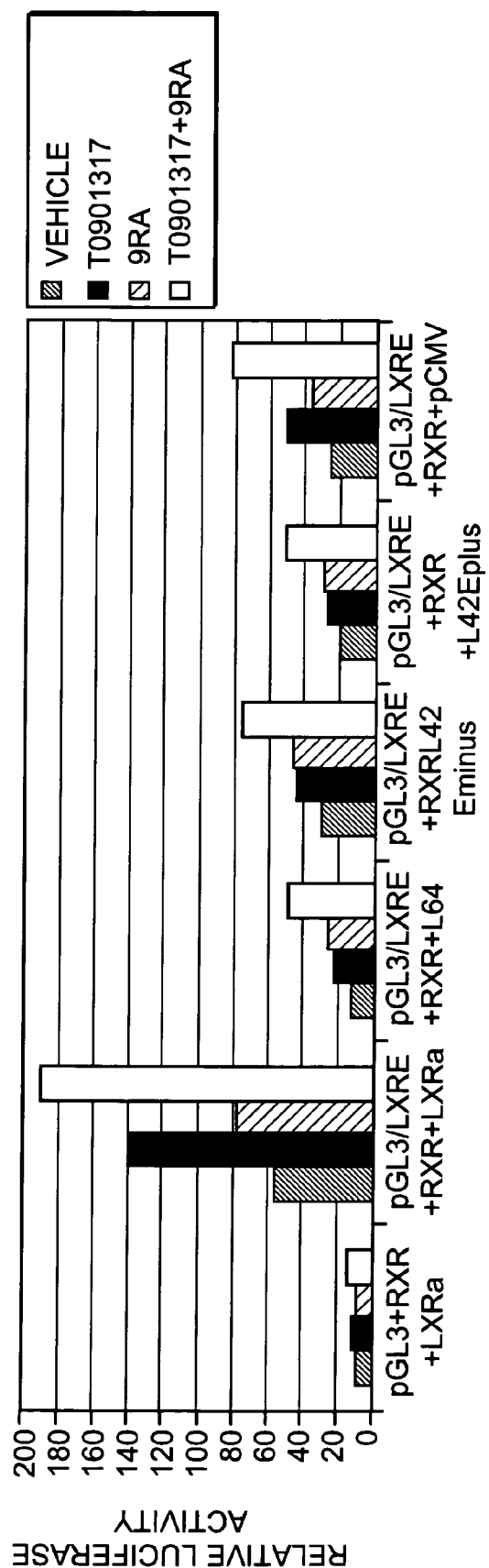
FIG. 9 is a bar graph depicting the results of experiments assaying LXRα-64 and LXRα-42 inhibition of LXR ligand-dependent activation of a reporter gene.
Figure 10:
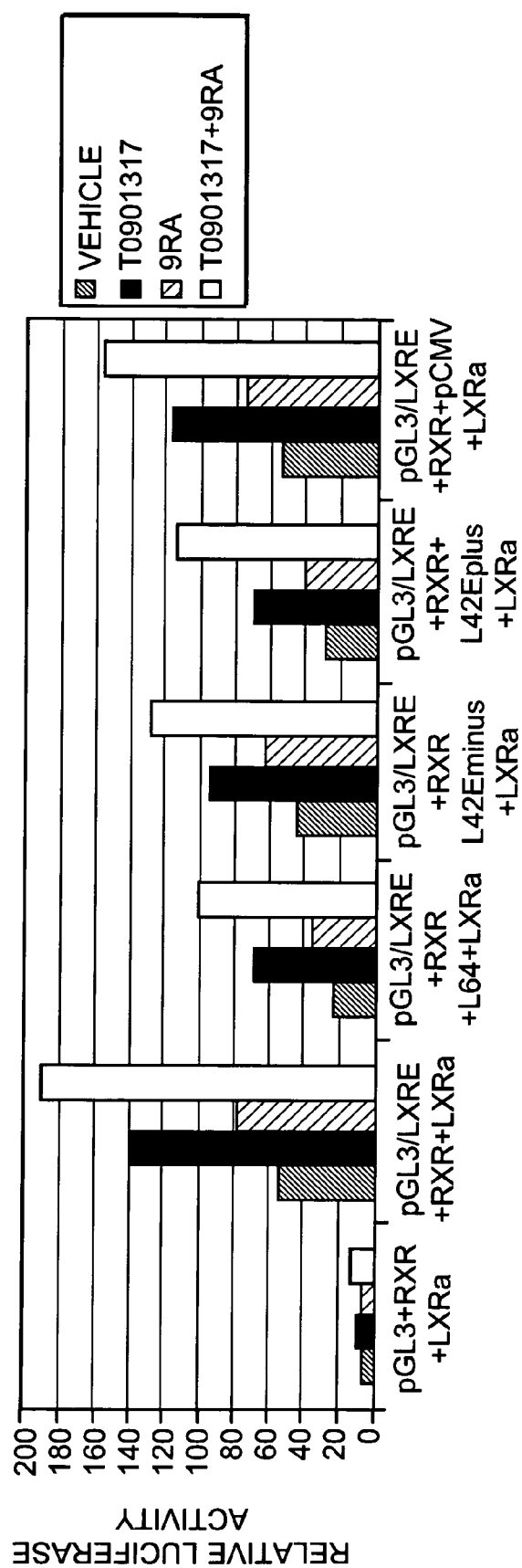
FIG. 10 is a bar graph depicting the results of experiments assaying the inhibition of LXR ligand-dependent activation of a reporter gene by LXRα-64 and LXRα-42. The difference between this experiment and the experiment whose results are shown in FIG. 9 is that 293 cells were cotransfected with the wild type LXRα and each of the new variants simultaneously.

It is also demonstrated herein that the novel LXRα variants are functional in that they can act as dominant negative modulators of wild-type LXRα activity. In addition, LXRα-64 and LXRα-42e⁺ and LXRα-42e⁻ variants have been found to be upregulated by LXR or RXR agonists in human monocyte/macrophage THP-1 cells (FIG. 8). Furthermore, LXR ligand-dependent activation was found to be sharply decreased when the novel LXRα-64, LXRα-42e⁺, and LXRα-42e⁻ variants were co-transfected with a reporter gene (FIGS. 9 and 10). Ligand-dependent induction of LXR-dependent pathway genes was also decreased in the presence of LXRα-64 in the presence of an LXRα agonist (FIGS. 11 and 12), and in some cases, even in the absence of an LXRα agonist (FIG. 11).

The three novel LXRα variants have also been shown to antagonize the biological/biochemical activity of a naturally occurring (wild type) LXRα protein by acting as dominant negative genes. A portion of an LXRα protein, e.g., a DNA binding domain (DBD), can also activate, somewhat less efficiently than a wild type LXRα, the biological/biochemical activities of a wild type LXRα protein.

Increasing the expression or activity of an LXRα variant (e.g., LXRα-64) is useful for treating disorders associated with the expression of SREBP-C1. For example, disrupting the activity of an LXRα, e.g., by overexpressing an LXRα-64 or increasing the activity of an LXRα-64 that is expressed in a cell (e.g., by administering a compound that differentially binds to LXRα-64 compared to wild type LXRα) can provide a method of inhibiting the insulin induction of SREBP-C1, and therefore provides a method of inhibiting undesirable induction of fatty acid synthesis by insulin. In another example, overexpressing an LXRα variant (e.g., LXRα-64) or selectively activating an LXRα variant (for example, with a compound that differentially binds to the LXRα-variant) can result in inhibition of SREBP-C1, and therefore provides a method of treating hypertriglyceridemia, which is a condition that is a strong predictor of heart disease. In another example, lowered SREBP-C1 expression (by increased expression or activity of an LXRα variant such as LXRα-64) can result in lower expression of VLDL-TGs (very low density lipoprotein triglycerides), a desirable effect in certain disorders such as diabetes and certain types of hyperlipoproteinemia. Wild type LXR has the effect of upregulating ABCA1, which is involved in reverse cholesterol transport and it has been found that an LXRα variant can inhibit basal expression of SREBP-1C, which is involved in triglyceride synthesis.

Nuclear receptors that heterodimerize with RXR and activation of these heterodimers results in increased expression of specific genes. In the case of undesirable expression of one or more of these genes (e.g., LXR-mediated upregulation of SREBP1c), then overexpression of an LXRα-64 is beneficial to a subject if expression of the LXRα variant binds to the RXR, thereby decreasing the availability of the RXR for heterodimerization and therefore reducing induction undesirable gene expression.

As more fully described below, the present invention provides isolated nucleic acids that encode each of the novel variants of LXRα homologues and fragments thereof. The invention further provides vectors for propagation and expression of the nucleic acids of the present invention, host cells comprising the nucleic acids and vectors of the present invention, proteins, protein fragments, and protein fusions of the present invention, and antibodies specific for all of any one of the variants. The invention provides pharmaceutical or physiologically acceptable compositions comprising, the polypeptides, polynucleotides and/or antibodies of the present invention, as well as, typically, a physiologically acceptable carrier. The present invention additionally provides diagnostic, investigational, and therapeutic methods based on the LXRα-64, LXRα-42e⁺ and LXRα-42e⁻ nucleic acid fragments, polypeptides and antibodies of the present invention.

Definitions

The following definitions and abbreviations are provided for the full understanding of terms and abbreviations used in this specification.

As used herein and in the appended claims, the singular forms "a", "an", and "the" include the plural reference unless the context clearly indicates otherwise. Thus, for example, a reference to "a host cell" includes a plurality of such host cells, and a reference to "an antibody" is a reference to one or more antibodies and equivalents thereof known to those skilled in the art, and so forth.

The abbreviations in the specification correspond to units of measure, techniques, properties or compounds as follows: "min" means minutes, "h" means hour(s), "μL" means microliter(s), "mL" means milliliter(s), "mM" means millimolar, "M" means molar, "mmole" means millimole(s), "kb" means kilobase, "bp" means base pair(s), and "IU" means International Units.

"Dulbecco's-modified Eagle Medium" is abbreviated DMEM.

"High performance liquid chromatography" is abbreviated HPLC.

"High throughput screening" is abbreviated HTS.

"Open reading frame" is abbreviated ORF.

"Polyacrylamide gel electrophoresis" is abbreviated PAGE.

"Sodium dodecyl sulfate-polyacrylamide gel electrophoresis" is abbreviated SDS-PAGE.

"Polymerase chain reaction" is abbreviated PCR.

"Reverse transcriptase polymerase chain reaction" is abbreviated RT-PCR.

"Liver X receptor alpha" is abbreviated LXRα.

"Retinoid X receptor" is abbreviated RXR. RXR refers to all RXRs including RXRα, RXRβ, RXRγ, and combinations thereof.

"DNA binding domain" is abbreviated DBD.

"Ligand binding domain" is abbreviated LBD.

"Untranslated region" is abbreviated UTR.

"Sodium dodecyl sulfate" is abbreviated SDS.

In the context of this disclosure, a number of terms shall be utilized. As used herein, the term "nucleic acid molecule" refers to the phosphate ester form of ribonucleotides (RNA molecules) or deoxyribonucleotides (DNA molecules), or any phosphoester analogs, in either single-stranded form, or a double-stranded helix. Double-stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described according to the normal convention of giving only the sequence in the 5' to 3' direction along the nontranscribed strand of DNA (i.e., the strand having a sequence corresponding to the mRNA).

A "recombinant nucleic acid molecule" is a nucleic acid molecule that has undergone a molecular biological manipulation, or is derived from a molecule that has undergone biological manipulation, i.e., non-naturally occurring nucleic acid molecule. Furthermore, the term "recombinant DNA molecule" refers to a nucleic acid sequence that is not naturally occurring, or can be made by the artificial combination of two otherwise separated segments of sequence, i.e., by ligating together pieces of DNA that are not normally continuous. By "recombinantly produced" is meant production of a non-naturally occurring combination, often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, John Wiley & Sons, New York, N.Y. (1989), and *DNA Cloning: A Practical Approach*, Volumes I and II (ed. D. N. Glover) IREL Press, Oxford, (1985).

In some cases, a recombinant nucleic acid molecule is constructed to replace a codon with a redundant codon encoding the same or a conservative amino acid, while typically introducing or removing a sequence recognition site. Alternatively, a recombinant nucleic acid molecule is designed to join together nucleic acid segments of desired functions to generate a single genetic entity comprising a desired combination of functions not found in the common naturally occurring forms of a manipulated sequence. Restriction enzyme recognition sites can be the target of such artificial manipulations, but other site-specific targets, e.g., promoters, DNA replication sites, regulation sequences, control sequences, or other useful features may be incorporated by design. Examples of recombinant nucleic acid molecules include recombinant vectors, such as cloning or expression vectors that contain DNA sequences, which are in a 5' to 3' (sense) orientation or in a 3' to 5' (antisense) orientation. Vectors suitable for making recombinant vectors (e.g., expression vectors) that include LXRα variant sequences and fragments thereof are known in the art.

The terms "polynucleotide," "nucleotide sequence," "nucleic acid," "nucleic acid molecule," "nucleic acid sequence," "nucleic acid fragment," "oligonucleotide," "gene," "mRNA encoded by a gene" refer to a series of nucleotide bases (also called "nucleotides") in DNA and RNA, and include any chain of two or more nucleotides, RNA or DNA (either single or double stranded, coding, complementary or antisense), or RNA/DNA hybrid sequences of more than one nucleotide in either single chain or duplex form (although each of the above species may be particularly specified).

The polynucleotides can be chimeric mixtures or derivatives, or modified versions thereof, and can be single-stranded or double-stranded. A polynucleotide can be modified at a base moiety, sugar moiety, or phosphate backbone, for example, to improve stability of the molecule or alter its hybridization parameters. An antisense polynucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylamino methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. A nucleotide sequence typically carries genetic information, including the information used by cellular machinery to make proteins and enzymes. These terms include double- or single-stranded genomic and cDNA, RNA, any synthetic polynucleotide, genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing modified bases, for example thio-uracil, thio-guanine, and fluoro-uracil, or containing carbohydrate, or lipids.

A "genomic DNA" is a DNA strand that has a nucleotide sequence homologous with a gene. By way of example, a fragment of chromosomal DNA is a genomic DNA.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Polynucleotides of the invention can be synthesized using methods known in the art, e.g., by use of an automated DNA synthesizer (such as those that are commercially available from Biosearch, Applied Biosystems). As examples, phosphorothioate oligonucleotides can be synthesized by the method of Stein et al., Nucl. Acids Res., 16, 3209, (1988), methylphosphonate oligonucleotides can be prepared by use of controlled pore glass polymer supports (Sarin et al., Proc. Natl. Acad. Sci. U.S.A. 85, 7448-7451, (1988).

A number of methods have been developed for delivering antisense DNA or RNA to cells, e.g., antisense molecules can be injected directly into a tissue site. Modified antisense molecules that are designed to target specific cells (e.g., an antisense nucleic acid linked to a peptide or antibody that can specifically bind to a receptor or antigen expressed on the target cell surface) can be administered systemically. An antisense RNA molecule can be generated by in vitro or in vivo transcription of a DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense constructs that synthesize antisense RNA constitutively or inducibly, depending on the promoter used, can be introduced stably into cell lines. To improve intracellular concentrations of the antisense to a level sufficient to suppress translation of targeted endogenous mRNAs, one may utilize a recombinant DNA construct in which the antisense oligonucleotide is placed under the control of a strong promoter. The use of such a construct to transfect target cells will result in the transcription of sufficient amounts of single-stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA in the cell. Such a vector can remain episomal or become chromosomally integrated, as long as it can be transcribed to produce the desired antisense RNA. Such vectors can be constructed by recombinant DNA technology methods known in the art. Vectors can be plasmid, viral, or others known in the art that are suitable for replication and expression in mammalian cells. Expression of a sequence encoding an antisense RNA can be facilitated using any promoter known in the art to act in mammalian, e.g., human cells. Such promoters can be inducible or constitutive. Such promoters include, but are not limited to, the SV40 early promoter region (Bernoist and Chambon, Nature, 290, 304-310, (1981)), the promoter contained in the 3' long terminal repeat of Rous sarcoma virus (Yamamoto et al., Cell, 22, 787-797, (1980)), the herpes thymidine kinase promoter (Wagner et al., Proc. Natl. Acad. Sci. U.S.A. 78, 1441-1445, (1981)), and the regulatory sequences of the metallothionein gene (Brinster et al., Nature 296, 39-42, (1982)). Any type of plasmid, cosmid, yeast artificial chromosome, or viral vector can be used to prepare the recombinant DNA construct that can be introduced directly into a tissue site. Alternatively, viral vectors can be used that selectively infect the desired tissue, in which case administration may be accomplished by another route (e.g., systemically).

Ribozymes are RNA molecules possessing the ability to specifically cleave single-stranded RNA in a manner analogous to DNA restriction endonucleases. Through the modification of nucleotide sequences that encode a ribozyme, it is possible to engineer molecules that recognize specific nucleotide sequences in an RNA molecule and cleave it (Cech, JAMA, 260, 3030, (1988)). A major advantage of this approach is that, because they are sequence-specific, only mRNAs with specific sequences are inactivated.

The polynucleotides described herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids can also be modified by other means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, or carbamates) and with charged linkages (e.g., phosphorothioates or phosphorodithioates). Polynucleotides may contain one or more additional covalently linked moieties, such as, for example, proteins (e.g., nucleases, toxins, antibodies, signal peptides, or poly-L-lysine), intercalators (e.g., acridine or psoralen), chelators (e.g., metals, radioactive metals, iron, or oxidative metals), and alkylators. The polynucleotides may be derivatized by formation of a methyl or ethyl phosphotriester or an alkyl phosphoramidate linkage. Furthermore, the polynucleotides herein can also be modified with a label capable of providing a detectable signal, either directly or indirectly. Exemplary labels include radioisotopes, fluorescent molecules, biotin, and the like.

The term "upstream" refers to a location that is toward the 5' end of the polynucleotide from a specific reference point.

The terms "base paired" and "Watson and Crick base paired" are used interchangeably herein to refer to nucleotides that can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (see Stryer, (1995) *Biochemistry*, 4th edition, which disclosure is hereby incorporated by reference in its entirety).

The term "exon" refers to a nucleic acid sequence found in genomic DNA that is predicted (e.g., using bioinformatics) and/or experimentally confirmed to contribute contiguous sequence to a mature mRNA transcript.

The terms "branch site" and "3' acceptor sites" refer to consensus sequences of 3-splice junctions in eukaryotic mRNAs. Almost all introns begin with GU and end with AG. From the analysis of many exon-intron boundaries, extended consensus sequences of preferred nucleotides at the 5 and 3 ends have been established. In addition to AG, other nucleotides just upstream of the 3' splice junction also are important for precise splicing (i.e., branch site consensus, YNYURAY and 3' acceptor site, (Y)nNAG G).

The term "nucleic acid fragment encoding polypeptide" encompasses a polynucleotide that includes only the coding sequence as well as a polynucleotide that includes coding sequence and additional coding or non-coding sequence.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook, J. et al. eds., *Molecular Cloning: A Laboratory Manual* (2d Ed. 1989) Cold Spring Harbor Laboratory Press, NY. Vols. 1-3 (ISBN 0-87969-309-6). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to a higher $T_m$, e.g., 50% formamide, 5× or 6×SSC. In general, high stringency conditions are hybridization conditions hybridization in 6×SSC (1 M NaCl), 50% formamide, 1% SDS at 42° C., followed by washing for 20 minutes in 1×SSC, 0.1% SDS at 42° C., and then washing three times for 20 minutes each at 68° C. in 0.2×SSC, 0.1% SDS. Hybridization requires that the two nucleic acids contain complementary sequences although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (Sambrook et al. eds., *Molecular Cloning: A Laboratory Manual* (2d Ed. 1989) Cold Spring Harbor Laboratory Press, NY. Vols. 1-3. (ISBN 0-87969-309-6), 9.50-9.51). For hybridization with shorter nucleic acids, i.e., oligonucleotides, the position of mismatches becomes more important, and the length of the oligonucleotide determines its specificity (Sambrook et al. eds., *Molecular Cloning: A Laboratory Manual* (2d Ed. 1989) Cold Spring Harbor Laboratory Press, NY. Vols. 1-3. (ISBN 0-87969-309-6), 11.7-11.8). The $T_m$ of such sequences can also be calculated and appropriate hybridization conditions determined.

Nucleic acid molecules described herein include nucleic acid sequences that hybridize under stringent conditions to the LXRα variant coding sequences described herein and complementary sequences thereof. For the purposes of this invention, the term "stringent conditions" means hybridization will occur only if there is at least 90%, e.g., at least 95% identity between the nucleic acid sequences. Accordingly, the present invention also includes isolated nucleic fragments that are complementary to the complete sequences as reported in the accompanying Sequence Listing as well as those that are at least 95% identical to such sequences, and polynucleotides having sequences that are complementary to the aforementioned polynucleotides. The polynucleotides of the present invention that hybridize to the complement of LXRα variant coding sequences described herein generally encode polypeptides that retain substantially the same biological function or activity as the mature LXRα polypeptide encoded by the cDNA of SEQ ID NO:3, SEQ ID NO:5 or SEQ ID NO:7.

A "substantial portion" of an amino acid or nucleotide sequence is a sufficient amount of the amino acid sequence of a polypeptide or the nucleotide sequence of a gene to putatively identify that polypeptide or gene, either by direct evaluation of the sequence by one skilled in the art, or by computer automated sequence comparison and identification using an algorithm such as BLAST (Basic Local Alignment Search Tool; Altschul, S. F., et al., (1993) J. Mol. Biol. 215:403-410; see also ncbi.nlm.nih.gov/BLAST. In general, a sequence of at least ten, e.g., at least 15, at least 20, at least 25, or at least 30 or more contiguous nucleotides is necessary to putatively identify a polypeptide or nucleic acid sequence as homologous to a known protein or gene. Moreover, with respect to nucleotide sequences, gene specific oligonucleotide probes comprising 15-30 (e.g., 20-30) contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-25 bases (e.g., 12-20 bases, 15-20 bases) can be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The present specification teaches partial or complete amino acid and nucleotide sequences encoding one or more particular LXR variants. The skilled artisan, having the benefit of the sequences as reported herein, can use all or a substantial portion of the disclosed sequences for purposes known to those skilled in this art. Accordingly, the present invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine.

"Identity" or "similarity", as known in the art, refers to relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991. Methods commonly employed to determine identity or similarity between sequences include, but are not limited to those disclosed in Carillo, H. and Lipman, D., SIAM *J. Applied Math.* 48:1073 (1988). Methods to determine identity and similarity are codified in publicly available computer programs. Computer program methods to determine identity and similarity between two or more sequences include, but are not limited to, GCG program package (Devereux, J., et al., Nucleic Acids Res. 12(1): 387 (1984)), BLASTP, BLASTN, and FASTA (Paschal, S. F. et al., J. Molec. Biol. 215: 403 (1990)).

The term "homologous" refers to the degree of sequence similarity between two polymers (i.e., polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

The term "percent homology" refers to the extent of amino acid sequence identity between polypeptides. The homology between any two polypeptides is a direct function of the total number of matching amino acids at a given position in either sequence, e.g., if half of the total number of amino acids in either of the sequences are the same then the two sequences are said to exhibit 50% homology.

The term "ortholog" refers to genes or proteins that are homologs via speciation, e.g., closely related and assumed to have common descent based on structural and functional considerations. Orthologous proteins generally have the same function and the same activity in different species. The term "paralog" refers to genes or proteins that are homologs via gene duplication, e.g., duplicated variants of a gene within a genome. See also, Fritch, W M (1970) Syst. Zool. 19:99-113. The term "ortholog" may refer to a polypeptide from another species that corresponds to LXRα variant-like polypeptide amino acid sequence as set forth in SEQ ID NOS:4, 6, 8, 17, or 19. For example, mouse and human LXRα-like polypeptides are considered to be orthologs of each other.

The term "fragment", "analog", and "derivative" when referring to the polypeptide of the present invention (e.g., SEQ ID NOS:4, 6, 8, 17, and 19), can refer to a polypeptide that retains essentially at least one biological function or activity as the reference polypeptide. Thus, an analog includes a precursor protein that can be activated by cleavage of the precursor protein portion to produce an active mature polypeptide. The fragment, analog, or derivative of the polypeptide described herein (e.g., SEQ ID NOS:4, 6, 8, 17, and 19) may be one having conservative or non-conservative amino acid substitution. The substituted amino acid residues may or may not be encoded by the genetic code, or the substitution may be such that one or more of the substituted amino acid residues includes a substituent group, is one in which the polypeptide is fused with a compound such as polyethylene glycol to increase the half-life of the polypeptide, or one in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

"Conserved" residues of a polynucleotide sequence are those residues that occur unaltered in the same position of two or more related sequences being compared. Residues that are relatively conserved are those that are conserved amongst more related sequences than residues appearing elsewhere in the sequences.

Related polynucleotides are polynucleotides that share a significant proportion of identical residues.

Different polynucleotides "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides also "correspond" to each other if they serve a similar function, such as encoding a related polypeptide in different species, strains or variants that are being compared.

An "analog" of a DNA, RNA or a polynucleotide, refers to a molecule resembling a naturally occurring polynucleotide in form and/or function (e.g., in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al., Chemical Reviews 90, 543-584, (1990).

The term "naturally occurring", as applied to an object, refers to the fact that an object may be found in nature. For example, a polypeptide or polynucleotide sequence that is present in an organism (including bacteria) that may be isolated from a source in nature and which has not been intentionally modified by man in the laboratory is naturally occurring. As used herein, the term "naturally occurring" is used to refer to a known LXRα, which is also referred to as "wild type" LXRα. This use of the term should not be construed to mean that the LXRα variants described herein are not naturally occurring.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., a nucleotide sequence can encode an amino acid sequence for a polypeptide or protein, e.g., enzyme.

The term "codon degeneracy" refers to divergence in the genetic code permitting variation of the polynucleotide sequence without affecting the amino acid sequence of an encoded polypeptide. Accordingly, the present invention relates to any nucleic acid fragment or the complement thereof that encodes all or a substantial portion of the amino acid sequence encoding an LXRα-64, LXRα-42e$^+$, or LXRα-42e$^-$ protein as set forth in SEQ ID NOS:4, 6, and 8.

The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence is (usually provided in sequence listings), and the non-coding strand, used as the template for transcription of a gene or cDNA, can be referred to as encoding the protein or other product of that gene or cDNA.

The polynucleotide of the present invention, can be in the form of RNA or in the form of DNA, which DNA includes cDNA and synthetic DNA. The DNA may be single-stranded or double-stranded. If it is single-stranded, it can be the coding strand or non-coding (antisense) strand. The coding sequence can be identical to the coding sequence of any one of SEQ ID NOS:3, 5, 7, 16, 18 or a fragment thereof or may be a different coding sequence which, as a result of degeneracy or redundancy of the genetic code, encodes for the same polypeptide as the reference coding sequence, e.g., one of SEQ ID NOS:3, 5, 7, 16, 18, or a fragment thereof.

The present invention includes variants of the hereinabove described polynucleotides described herein that encode fragments, analogs, and derivatives of the polynucleotides characterized by the deduced amino acid sequence of SEQ ID NOS:4, 6, 8, 17, or 19. The variant of the polynucleotide can be a naturally occurring allelic variant of the polynucleotide or a non-naturally occurring variant of the polynucleotide.

A polynucleotide of the present invention may have a coding sequence that is a naturally occurring allelic variant of the coding sequence characterized by the DNA sequence of the SEQ ID NOS:4, 6 or 8, 17 and 19.

The polynucleotide that encodes the mature polypeptide, i.e., an LXRα, may include only the coding sequence for the mature polypeptide or the coding sequence for the mature polypeptide and additional sequence such as gene control sequence, regulatory sequence, or secretory sequence.

The present invention therefore includes polynucleotides such that the coding sequence for the mature polypeptide may be operatively linked in the same reading frame to a polynucleotide sequence that aids in expression and secretion of a polypeptide from a host cell (e.g., a signal peptide). The polynucleotide may also encode a precursor protein.

A polynucleotide of the present invention may also have coding sequence fused in-frame to a marker sequence, such as hexa-histidine tag (Qiagen Inc.), at either 3' or 5' terminus of the gene, e.g., to allow purification of the polypeptide.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-known procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available.

The term "gene" refers to a nucleic acid fragment that expresses a specific protein, including regulatory sequences preceding (5' noncoding sequences) and following (3' noncoding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Target gene," "target gene sequence," "target DNA sequence," or "target sequence" refers to a gene where the gene, its RNA transcript, or its protein product is modulated by a transcription factor. The target sequence may include an intact gene, an exon, an intron, a regulatory sequence or any region between genes. The target gene may comprise a portion of a particular gene or genetic locus in the subject's genomic DNA. "Target gene," as used herein, refers to a differentially expressed gene involved in LXR responsive pathways. "Differential expression", refers to both quantitative as well as qualitative differences in a gene's temporal and/or tissue expression patterns. Examples of LXR target genes are SREBP-1c (sterol regulatory binding element 1c), FAS, CYP7A1 (cholesterol 7-alpha hydroxylase), ApoE, CETP (cholesterol ester transfer protein), LPL (lipoprotein lipase), ABCA1 (ATP-binding cassette transporter-1), ABCG1, ABCG5, ABCG8, ABCG4, and PLTP (phospholipid transfer protein) (Edwards et al. Vasc. Pharmacol. 38, (2002) 249-256). The term "regulatory sequences" refer to nucleotide sequences located upstream (5' non-coding sequences), within, or downstream (3' non-coding sequences) of a coding sequence, and which influence), e.g., transcription, RNA processing, RNA stability, or translation of the associated coding sequence. Regulatory sequences may include promoters, translation leader sequences, introns, and polyadenylation recognition sequences.

The term "gene control sequence" refers to the DNA sequences required to initiate gene transcription plus those required to regulate the rate at which initiation occurs. Thus a gene control sequence may consist of the promoter, where the general transcription factors and the polymerase assemble, plus all the regulatory sequences to which gene regulatory proteins bind to control the rate of these assembly processes at the promoter. For example, the control sequences that are suitable for prokaryotes may include a promoter, optionally an operator sequence, and a ribosome binding site. Eukaryotic cells are known to utilize promoters, enhancers, and/or polyadenylation signals.

The term "promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The term "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The term "domain" refers to an amino acid fragment with specific biological properties. This term encompasses all known structural and linear biological motifs. Examples of such motifs include but are not limited to helix-turn-helix motifs, leucine zippers, glycosylation sites, ubiquitination sites, alpha helices, and beta sheets, signal peptides which direct the secretion of proteins, sites for post-translational modification, enzymatic active sites, substrate binding sites, and enzymatic cleavage sites.

"DNA-binding domain" refers to the portion of any DNA binding protein that specifically interacts with desoxyribonucleotide strands. A sequence-specific DNA binding protein binds to a specific sequence or family of specific sequences showing a high degree of sequence identity with each other.

The term "LBD" or "ligand-binding domain" refers to the protein domain of a nuclear receptor, such as a steroid superfamily receptor or other suitable nuclear receptor as discussed herein, which binds a ligand (e.g., a steroid hormone).

The term "reporter gene" means any gene that encodes a product whose expression is detectable and/or quantifiable by physical, immunological, chemical, biochemical, or biological assays. A reporter gene product may, for example, have one of the following attributes, without restrictions: a specific nucleic acid chip hybridization pattern, fluorescence (e.g., green fluorescent protein), enzymatic activity, toxicity, or an ability to be specifically bound by a second molecule, labeled or unlabeled.

The term "RNA transcript" refers to the product resulting from RNA polymerase-catalyzed transcription of a DNA sequence. When the RNA transcript is a complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. The complementarity of an antisense RNA may be with any part of the specific nucleotide sequence, i.e., at the 5' non-coding sequence, 3' non-coding sequence, introns, or the coding sequence. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

"Functional RNA" refers to sense RNA, antisense RNA, ribozyme RNA, or other RNA that may not be translated but yet has an effect on cellular processes.

An "anti-sense" copy of a particular polynucleotide refers to a complementary sequence that is capable of hydrogen bonding to the polynucleotide and can therefor be capable of modulating expression of the polynucleotide. These are DNA, RNA or analogs thereof, including analogs having altered backbones, as described above. The polynucleotide to which the anti-sense copy binds may be in single-stranded form or in double-stranded form. A DNA sequence linked to a promoter in an "anti-sense orientation" may be linked to the promoter such that an RNA molecule complementary to the coding mRNA of the target gene is produced.

The antisense polynucleotide may comprise at least one modified sugar moiety selected from the group including but not limited to arabinose, 2-fluoroarabinose, xylulose, and hexose. In one embodiment, the antisense oligonucleotide may comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The term "sense" refers to sequences of nucleic acids that are in the same orientation as the coding mRNA nucleic acid sequence. A DNA sequence linked to a promoter in a "sense orientation" is linked such that an RNA molecule that contains sequences identical to an mRNA is transcribed. The produced RNA molecule, however, need not be transcribed into a functional protein.

A "sense" strand and an "anti-sense" strand when used in the same context refer to single-stranded polynucleotides that are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

The term "polynucleotide encoding polypeptide" encompasses a polynucleotide that may include only the coding sequence as well as a polynucleotide that may include additional coding or non-coding sequence.

The term "siRNA" or "RNAi" refers to small interfering RNAs and the process by which they function. siRNAs are capable of causing RNA interference and can cause post-transcriptional silencing of specific genes in cells, for example, in mammalian cells (including human cells) and in the body, for example, mammalian bodies (including humans). The phenomenon of RNA interference is described and discussed in Bass, Nature, 411, 428-29, (2001); Elbahir et al., Nature, 411, 494-98, (2001); and Fire et al., Nature, 391, 806-11, (1998), where methods of making interfering RNA also are discussed. The siRNAs based upon the sequence disclosed herein can be made by approaches known in the art, including the use of complementary DNA strands or synthetic approaches. Exemplary siRNAs could have up to 29 bps, 25 bps, 22 bps, 21 bps, 20 bps, 15 bps, 10 bps, 5 bps or any integer thereabout or therebetween.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein.

The term "overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

The term "altered levels" refers to the production of gene product(s) in transgenic organisms in amounts or proportions that differ from that of normal or non-transformed organisms. Over expression of the polypeptide of the present invention may be accomplished by first constructing a chimeric gene or chimeric construct in which the coding region is operatively linked to a promoter capable of directing expression of a gene or construct in the desired tissues at the desired stage of development. For reasons of convenience, the chimeric gene or chimeric construct may comprise promoter sequences and translation leader sequences derived from the same genes. 3' Non-coding sequences encoding transcription termination signals may also be provided. The instant chimeric gene or chimeric construct may also comprise one or more introns in order to facilitate gene expression. Plasmid vectors comprising the instant chimeric gene or chimeric construct can then be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene or chimeric construct. The skilled artisan will also recognize that different independent transformation events will result in different levels and patterns of expression (Jones et al., 1985, EMBO J. 4:2411-2418; De Almeida et al., 1989, Mol. Gen. Genetics 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The terms "cassette" or "expression cassette" refer to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

The term "expression system" means a host cell and compatible vector under suitable conditions, e.g., for the expression of a protein coded for by foreign DNA carried by the vector and introduced to the host cell. Common expression systems include E. coli host cells and plasmid vectors, insect host cells and Baculovirus vectors, and mammalian host cells and vectors.

The term "transfection" refers to the insertion of an exogenous polynucleotide into a host cell, irrespective of the method used for the insertion, or the molecular form of the polynucleotide that is inserted. The insertion of a polynucleotide per se and the insertion of a vector or plasmid comprised of the exogenous polynucleotide are included. The exogenous polynucleotide may be transcribed and translated by the cell, maintained as a nonintegrated vector, for example, a plasmid, or may be stably integrated into the host genome.

The term "transformed" refers to any known method for the insertion of a nucleic acid fragment into a host prokaryotic cell. The term "transfected" refers to any known method for the insertion of a nucleic acid fragment into a host eukaryotic cell. Such transformed or transfected cells include stably transformed or transfected cells in which the inserted DNA is rendered capable of replication in the host cell. They also include transiently expressing cells that express the inserted DNA or RNA for limited periods of time. The transformation or transfection procedure depends on the host cell being transformed. It can include packaging the nucleic acid fragment in a virus as well as direct uptake of the nucleic acid fragment, such as, for example, electroporation, lipofection, or microinjection. Transformation and transfection can result in incorporation of the inserted DNA into the genome of the host cell or the maintenance of the inserted DNA within the host cell in plasmid form. Methods of transformation are well known in the art and include, but are not limited to, lipofection, electroporation, viral infection, and calcium phosphate mediated direct uptake. Transfection methods are known to those in the art including calcium phosphate DNA co-precipitation (Methods in Molecular Biology, Vol. 7, Gene Transfer and Expression Protocols, Ed. E. J. Murray, Humana Press (1991)); DEAE-dextran; electroporation; cationic liposome-mediated transfection; and tungsten particle-facilitated microparticle bombardment (Johnston, Nature 346:776-777 (1990)). Strontium phosphate DNA co-precipitation (Brash et al., Molec. Cell. Biol. 7:2031-2034 (1987) is an alternative transfection method.

"Cells," "host cells," or "recombinant host cells" are terms used interchangeably herein. It is understood that such terms refer not only to the particular subject cell but also to the progeny or potential progeny of such a cell. Because certain modifications may occur in succeeding generations due to either mutation or environmental influences, such progeny may not be identical to the parent cell, but are still included within the scope of the term as used herein. The term "recombinant cell" refers to a cell that contains heterologous nucleic acid, and the term "naturally occurring cell" refers to a cell that does not contain heterologous nucleic acid introduced by the hand of man.

The cell may be a prokaryotic or a eukaryotic cell. Typical prokaryotic host cells include various strains of E. coli. Typical eukaryotic host cells are mammalian, such as Chinese hamster ovary cells or human embryonic kidney 293 cells (HEK 293 cells). The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA. It is further understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The term "clone" refers to a population of cells derived from a single cell or common ancestor by mitosis. A "cell line" refers to a clone of a primary cell that is capable of stable growth in vitro for several generations.

The term "cell growth" refers to an increase in the size of a population of cells.

The term "cell division" refers to mitosis, i.e., the process of cell reproduction.

The term "proliferation" refers to growth and division of cells. "Actively proliferating" means cells that are actively growing and dividing.

The term "differentiate" refers to having a different character or function from the original type of tissues or cells. Thus, "differentiation" is the process or act of differentiating.

The term "gene-inducible system" refers to the use of ligands to regulate gene expression. Several regulatory systems have been developed that utilize small molecules to induce gene expression (reviewed in Clackson, Curr. Opin. Chem. Biol., 1, 210-218, (1997); Lewandoski, Nat Rev Genet. 2, 743-755, (2001). A gene-inducible system is a molecular tool which allows for low to undetectable basal expression of a target gene when the system is not activated and increased expression levels of the target gene when the system is activated.

The term "inhibiting cellular proliferation" refers to slowing and/or preventing the growth and division of cells. Cells may further be specified as being arrested in a particular cell cycle stage: G1 (Gap 1), S phase (DNA synthesis), G2 (Gap 2) or M phase (mitosis).

The term "preferentially inhibiting cellular proliferation" refers to slowing and/or preventing the growth and division of cells as compared to normal cells.

The term "apoptosis" refers to programmed cell death as signaled by the nuclei in normally functioning human and animal cells when age or state of cell health and condition dictates. "Apoptosis" is an active process requiring metabolic activity by the dying cell, often characterized by cleavage of the DNA into fragments that give a so called laddering pattern on gels. Cells that die by apoptosis do not usually elicit the inflammatory responses that are associated with necrosis, though the reasons are not clear. Cancerous cells, however, are unable to experience, or have a reduction in, the normal cell transduction or apoptosis-driven natural cell death process. Morphologically, apoptosis is characterized by loss of contact with neighboring cells, concentration of cytoplasm, endonuclease activity-associated chromatin condensation and pyknosis, and segmentation of the nucleus, among others.

The term "polypeptide" refers to a polymer of amino acids without regard to the length of the polymer; thus, "peptides," "oligopeptides", and "proteins" are included within the definition of polypeptide and used interchangeably herein. The term refers to a naturally occurring or synthetic polymer of amino acid monomers (residues), irrespective of length, where amino acid monomer here includes naturally occurring amino acids, naturally occurring amino acid structural variants, or synthetic non-naturally occurring analogs that are capable of participating in peptide bonds. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, proteins—structure and molecular properties, 2nd Ed., T. E. Creighton, W. H. Freeman and Company, New York (1993); posttranslational covalent modification of proteins, b. c. Johnson, Ed., Academic Press, New York, pgs. 1-12, 1983; Seifter et al., Meth. Enzymol. 182:626-646, 1990; Rattan et al., Ann. NY Acad. Sci. 663:48-62, 1992). Also included within the definition are polypeptides which contain one or more analogs of an amino acid (including, for example, non-naturally occurring amino acids, amino acids which only occur naturally in an unrelated biological system, or modified amino acids from mammalian systems), polypeptides with substituted linkages, as well as other modifications known in the art, both naturally occurring and non-naturally occurring. The term "polypeptide" may also be used interchangeably with the term "protein" or "peptide".

The term "peptide" refers to any polymer of two or more amino acids, wherein each amino acid is linked to one or two other amino acids via a peptide bond (—CONH—) formed between the NH.sub.2 and the COOH groups of adjacent amino acids. Preferably, the amino acids are naturally occurring amino acids, particularly alpha-amino acids of the L-enantiomeric form. However, other amino acids, enantiomeric forms, and amino acid derivatives may be included in a peptide. Peptides include "polypeptides," which, upon hydrolysis, yield more than two amino acids. Polypeptides may include proteins, which typically comprise 50 or more amino acids. The term "oligopeptide" herein denotes a protein, polypeptide, or peptide having 25 or fewer monomeric subunits.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below.

The term "variant(s)" refers to a polypeptide plurality of polypeptides that differ from a reference polypeptide respectively. Generally, the differences between the polypeptide that differs in amino acid sequence from reference polypeptide, and the reference polypeptide are limited so that the amino acid sequences of the reference and the variant are closely similar overall and, in some regions, may be identical. A variant and reference polypeptide may differ in amino acid sequence by one or more substitutions, deletions, additions, fusions and truncations, which may be present in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. Additionally, a variant may be a fragment of a polypeptide of the invention that differs from a reference polypeptide sequence by being shorter than the reference sequence, such as by a terminal or internal deletion. A variant of a polypeptide of the invention also includes a polypeptide that retains essentially the same biological function or activity as such polypeptide e.g., precursor proteins that can be activated by cleavage of the precursor portion to produce an active mature polypeptide. Moreover, a variant may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines. Among polypeptide variants in this regard are variants that differ from the aforementioned polypeptides by amino acid substitutions, deletions or additions. The substitutions, deletions or additions may involve one or more amino acids. Alterations in the sequence of the amino acids may be conservative or non-conservative amino acid substitutions, deletions or additions. All such variants defined above are deemed to be within the scope of those skilled in the art from the teachings herein and from the art.

The LXRα variant described herein that is designated LXRα-64 (SEQ ID NO:4), is homologous to the previously known LXRα in that it contains a DNA binding domain and a ligand binding domain; however, different from the known LXRα in its middle part of the sequence in that it contains 64 new amino acids. By virtue of the partial identity, and partial divergence of their amino acid sequences, the variant and the known homologues may have some functionality in common but may differ in other functions. For example, wild-type LXRα is known to be a sensor for cellular oxysterols and, when activated by its agonists, increase the expression of genes that control sterol and fatty acid metabolism/homeostasis where as LXRα-L64, LXRα-42e$^+$ and LXRα-42e$^-$ function as dominant negative modulators of the wild type LXRα.

The term "dominant negative polypeptide" means an inactive variant of a protein, which, by interacting with the cellular machinery, displaces an active protein from its interaction with the cellular machinery or competes with the active protein, thereby reducing the effect of the active protein. For example, a dominant negative receptor that binds a ligand but does not transmit a signal in response to binding of the ligand can reduce the biological effect of expression of the ligand. Likewise, a dominant negative catalytically inactive kinase that interacts normally with target proteins but does not phosphorylate the target proteins can reduce phosphorylation of the target proteins in response to a cellular signal. Similarly, a dominant negative transcription factor that binds to a promoter site in the control region of a gene but does not increase gene transcription can reduce the effect of a normal transcription factor by occupying promoter binding sites without increasing transcription.

The term "splice variant" refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of them may encode different amino acid sequences. The term splice variant may also refer to the proteins encoded by the above cDNA molecules. The splice variant may be partially identical in sequence to the known homologous gene product. "Splice variants" refer to a plurality of proteins having non-identical primary amino acid sequence but that share amino acid sequence encoded by at least one common exon.

As used herein, the phrase "alternative splicing" and its linguistic equivalents includes all types of RNA processing that lead to expression of plural protein isoforms from a single gene; accordingly, the phrase "splice variant(s)" and its linguistic equivalents embraces mRNAs transcribed from a given gene that, however processed, collectively encode plural protein isoforms. For example, and by way of illustration only, splice variants can include exon insertions, exon extensions, exon truncations, exon deletions, alternatives in the 5' untranslated region ("5' UT") and alternatives in the 3' untranslated region ("3' UT"). Such 3' alternatives include, for example, differences in the site of RNA transcript cleavage and site of poly(A) addition (e.g., Gautheret et al., *Genome Res.* 8:524-530 (1998)).

The term "isolated" means that the material is removed from its original or native environment (e.g., the natural environment if it is naturally occurring). Therefore, a naturally occurring polynucleotide or polypeptide present in a living animal is not isolated, but the same polynucleotide or polypeptide, separated by human intervention from some or all of the coexisting materials in the natural system, is isolated. For example, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Such polynucleotides could be part of a vector, integrated into a host cell chromosome at a heterologous site, and/or such polynucleotides or polypeptides could be part of a composition, and still be isolated in that such vector or composition is not part of the environment in which it is found in nature.

The term "purified" does not require absolute purity; rather, it is intended as a relative definition. Purification of starting material or natural material to at least one order of magnitude, preferably two or three orders, and more preferably four or five orders of magnitude is expressly contemplated. Similarly, the term "substantially purified" refers to a substance, which has been separated or otherwise removed, through human intervention, from the immediate chemical environment in which it occurs in Nature. Substantially purified polypeptides or nucleic acids may be obtained or produced by any of a number of techniques and procedures generally known in the field.

The term "purified" is further used herein to describe a polypeptide or polynucleotide of the present invention that has been separated from other compounds including, but not limited to, polypeptides, polynucleotides, carbohydrates, or lipids. The term "purified" may be used to specify the separation of monomeric polypeptides of the invention from oligomeric forms such as homodimers, heterodimers, or trimers. The term "purified" may also be used to specify the separation of covalently closed (i.e., circular) polynucleotides from linear polynucleotides. A substantially pure polypeptide or polynucleotide typically comprises about 50%, preferably 60 to 90% weight/weight of a polypeptide or polynucleotide sample, respectively, more usually about 95%, and preferably is over about 99% pure but, may be specified as any integer of percent between 50 and 100. Polypeptide and polynucleotide purity, or homogeneity, is indicated by a number of means well known in the art, such as agarose or polyacrylamide gel electrophoresis of a sample, followed by visualizing a single band upon staining the gel. For certain purposes, higher resolution can be provided by using HPLC or other means that are known in the art. As an alternative embodiment, purification of the polypeptides and polynucleotides of the present invention may be expressed as "at least" a percent purity relative to heterologous polypeptides and polynucleotides (DNA, RNA or both). In one embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. In another embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

A protein may be said to be "isolated" when it exists at a purity not found in nature where purity may be adjudged with respect to the presence of proteins of other sequence, with respect to the presence of non-protein compounds, such as nucleic acids, lipids, or other components of a biological cell, or when it exists in a composition not found in nature, such as in a host cell that does not naturally express that protein.

The polypeptide and the polynucleotides of the present invention are preferably provided in an isolated form, and preferably are purified to homogeneity.

The term "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides include but are not limited to intracellular localization signals.

The term "antibody" refers to a polypeptide, at least a portion of which is encoded by at least one immunoglobulin gene, or fragment thereof, and that can bind specifically to a desired target molecule. The term includes naturally occurring forms, as well as fragments and derivatives.

Fragments may include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'$_2$, and single chain Fv (scFv) fragments. Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), *Intracellular Antibodies: Research and Disease Applications*, Springer-Verlag New York, Inc. (1998) (ISBN: 3540641513), the disclosure of which is incorporated herein by reference in its entirety).

The term "immunoreactive" refers to a polypeptide when it is "immunologically reactive" with an antibody, i.e., when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art. An "immunoreactive" polypeptide may also be "immunogenic."

Antibodies can be produced by any known technique, including harvest from cell culture of native B lymphocytes, harvest from culture of hybridomas, recombinant expression systems, and phage display.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier. The portions of the antigen that make contact with the antibody are denominated "epitopes".

The term "molecular binding partners"—and equivalently, "specific binding partners"—refer to pairs of molecules, typically pairs of biomolecules, which exhibit specific binding. Non-limiting examples are receptor and ligand, antibody and antigen, and biotin to any of avidin, streptavidin, NeutrAvidin™ and CaptAvidin™.

The term "binding partner" or "interacting proteins" refers to a molecule or molecular complex which is capable of specifically recognizing or being recognized by a particular molecule or molecular complex, as for example, an antigen and an antigen-specific antibody or an enzyme and its inhibitor. Binding partners may include, for example, biotin and avidin or streptavidin, IgG, and protein A, receptor-ligand couples, protein-protein interaction, and complementary polynucleotide strands. The term "binding partner" may also refer to polypeptides, lipids, small molecules, or nucleic acids that bind to polypeptides in cells. A change in the interaction between a protein and a binding partner can manifest itself as an increased or decreased probability that the interaction forms, or an increased or decreased concentration of protein-binding partner complex. For example, LXRα-64 or LXRα-42 protein may bind with another protein or polypeptide and form a complex that may result in modulating LXR or RXR activity.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample.

The term "dimeric" refers to a specific multimeric molecule where two protein polypeptides are associated through covalent or non-covalent interactions. "Dimeric molecule" can be receptors that are comprised of two identical (homodimeric) or different (heterodimeric) protein molecule subunits.

The term "homodimer" refers to a dimeric molecule wherein the two subunit constituents are essentially identical, for example RXR and RXR. The "homodimeric complex" refers to a protein complex between two identical receptors (e.g., RXR/RXR). The "homodimeric complex" may include dimeric proteins with minor microheterogeneities that occasionally arise on production or processing of recombinant proteins. The term "homodimerization" refers to the process by which two identical subunits (e.g., RXR and RXR) dimerize.

The term "heterodimer" refers to a dimeric molecule wherein the two subunit constituents are different, for example RXR and LXR. The term "heterodimeric complex" refers to a protein complex between any one of the nuclear receptors (e.g., RXR and any one of the variants of the present invention, or, RXR and LXRα, LXRβ, PPARα, PPARγ, PPARδ, RAR, XR, or PXR). The term "heterodimerization" refers to a process by which two different subunits (e.g., RXR and LXRα-64) dimerize.

The term "naturally heterodimerizes" refers to a process by which a molecule (e.g., polypeptide) normally heterodimerizes with different molecules in nature. For example, polypeptides that naturally heterodimerize with RXR are the nuclear receptors that normally heterodimerize with RXR in nature such as LXRα, LXRβ, PPARα, PPARγ, PPARδ, RAR, XR, and PXR.

The term "LXR responsive pathway" refers to any one of the pathways known in the art which involve activation or deactivation of a nuclear receptor (e.g., LXR or RXR), and which are at least partially mediated by the LXR.

The term "signal transduction pathway" refers to the molecules that propagate an extracellular signal through the cell membrane to become an intracellular signal. This signal can then stimulate a cellular response. The polypeptide molecules involved in signal transduction processes may be receptor and non-receptor proteins.

The term "receptor" refers to a molecular structure within a cell or on the surface of the cell that is generally characterized by the selective binding of a specific substance. Exemplary receptors include cell-surface receptors for peptide hormones, neurotransmitters, antigens, complement fragments and immunoglobulins as well as cytoplasmic receptors for steroid hormones.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. A "modulator" of a protein refers to a wide range of molecules (e.g., antibody, nucleic acid fragment, small molecule, peptide, oligopeptide, polypeptide, or protein) and/or conditions which can, either directly or indirectly, exert an influence on the activation and/or repression of the protein (e.g., receptor of interest), including physical binding to the protein, alterations of the quantity or quality of expression of the protein, altering any measurable or detectable activity, property, or behavior of the protein, or in any way interacts with the protein or compound.

The term "inhibit" refers to the act of diminishing, suppressing, alleviating, preventing, reducing or eliminating, whether partial or whole, a function or an activity. For example, inhibition of gene transcription or expression refers to any level of downregulation of these functions, including complete elimination of these functions. The term "inhibit" can be applied to both in vitro as well as in vivo systems. As used herein, the term "inhibitor" or "repressor" refer to any agent that inhibits.

The term "small molecule" refers to a synthetic or naturally occurring chemical compound, for instance a peptide or oligonucleotide that may optionally be derivatized, natural product or any other low molecular weight (typically less than about 5 KD) organic, bioinorganic or inorganic compound, of either natural or synthetic origin. Such small molecules may be a therapeutically deliverable substance or may be further derivatized to facilitate delivery.

The term "inducer" refers to any agent that induces, enhances, promotes or increases a specific activity, such as lipid metabolism, or LXR molecule expression.

The term "agent" or "test agent" or "test sample" refers to any molecule or combination of more than one molecule that is to be tested.

Examples of agents of the present invention include but are not limited to peptides, proteins, small molecules, and antibodies. Nucleotide fragments and portions, as well as antisense embodiments described, above may also serve as agents, if desired. Agents can be randomly selected or rationally selected or designed. As used herein, an agent is said to be "randomly selected" when the agent is chosen randomly without considering the specific interaction between the agent and the target compound or site. As used herein, an agent is said to be "rationally selected or designed," when the agent is chosen on a non-random basis that takes into account the specific interaction between the agent and the target compound or site and/or the conformation in connection with the agent's action.

The term "biological sample" is broadly defined to include any cell, tissue, biological fluid, organ, multi-cellular organism, and the like. A biological sample may be derived, for example, from cells or tissue cultures in vitro. Alternatively, a biological sample may be derived from a living organism or from a population of single-cell organisms. A biological sample may be a live tissue such as liver. The term "biological sample" is also intended to include samples such as cells, tissues or biological fluids isolated from a subject, as well as samples present within a subject. That is, the detection method of the invention can be used to detect LXR variant mRNA, protein, genomic DNA, or activity in a biological sample in vitro as well as in vivo. For example, in vitro techniques for detection of LXR variant mRNA include TaqMan analysis, northern hybridization, and in situ hybridization. In vitro techniques for detection of LXRα protein include enzyme-linked immunosorbent assays (ELISAs), western blots, immunoprecipitations and immunofluorescence. In vitro techniques for detection of LXR variant genomic DNA include southern hybridizations.

The term "test sample" refers to a biological sample from a subject of interest. For example, a test sample can be a cell sample or tissue sample. A "test sample" and "biological sample" are used interchangeably herein.

The term "body fluid" refers to any body fluid including, without limitation, serum, plasma, lymph fluid, synovial fluid, follicular fluid, seminal fluid, amniotic fluid, milk, whole blood, sweat, urine, cerebro-spinal fluid, saliva, sputum, tears, perspiration, mucus, tissue culture medium, tissue extracts, and cellular extracts. It may also apply to fractions and dilutions of body fluids. The source of a body fluid can be a human body, an animal body, an experimental animal, a plant, or other organism.

The terms "treatment", "treating", and "therapy" to any process, action, application, therapy, or the like, wherein a subject, including a human being, is provided medical aid with the object of improving the subject's condition, directly or indirectly, or slowing the progression of a condition or disorder in the subject.

Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease. As used herein, a "therapeutic agent" refers to any substance or combination of substances that assists in the treatment of a disease. Accordingly, a therapeutic agent includes, but is not limited to, small molecules, peptides, antibodies, ribozymes and antisense oligonucleotides.

Therapeutic agent or therapeutic compositions may also include a compound in a pharmaceutically acceptable form that prevents and/or reduces the symptoms of a particular disease. For example a therapeutic composition may be a pharmaceutical composition that prevents and/or reduces the symptoms of a lipid metabolism disorder. It is contemplated that the therapeutic composition of the present invention will be provided in any suitable form. The form of the therapeutic composition will depend on a number of factors, including the mode of administration. The therapeutic composition may contain diluents, adjuvants and excipients, among other ingredients.

The term "therapeutically effective amount" refers to the amount of a compound or composition of compounds that, when administered to a subject for treating a disease, is sufficient to effect such treatment for the disease. The "therapeutically effective amount" will vary, according to parameters known to those in the art, for example, depending on the compound, the disease, the severity of the disease, and the age, weight, or sex of the mammal to be treated.

The term "subject" refers to any mammal, including a human, or non-human subject. Non-human subjects can include experimental, test, agricultural, entertainment or companion animals.

The present invention incorporates by reference methods and techniques known in the field of molecular and cellular biology. These techniques include, but are not limited to techniques described in the following publications: Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4), Sambrook, J. et al. eds., *Molecular Cloning: A Laboratory Manual* (2d Ed. 1989) Cold Spring Harbor Laboratory Press, NY. Vols. 1-3. (ISBN 0-87969-309-6); Miller, J. H. & M. P. Calos eds., *Gene Transfer Vectors For Mammalian Cells* (1987) Cold Spring Harbor Laboratory Press, NY (ISBN 0-87969-198-0). The DNA coding for the protein of the present invention may be any one provided that it comprises the nucleotide sequence coding for the above-mentioned protein of the present invention.

Nucleic Acid Molecules

The present invention relates to isolated nucleic acid molecules that encode three novel LXRα variant proteins (i.e., LXRα-64, LXRα-42e$^+$, and LXRα-42e$^-$). Also included are nucleic acid molecules having at least 90% sequence identity to an LXRα variant protein or a fragment thereof, degenerate variants of an LXRα variant, variants that encode an LXRα-64, LXRα-42e$^+$, and LXRα-42e$^-$ protein having conservative or moderately conservative substitutions, cross-hybridizing nucleic acids (e.g., that hybridize under conditions of high stringency), and fragments thereof.

The sequences of the present invention are presented, respectively, in SEQ ID NO:3 (full length nucleotide sequence of LXRα-64, cDNA), SEQ ID NO:4 (full length amino acid sequence of LXRα-64), SEQ ID NO:5 (nucleotide sequence encoding the entirety of LXRα-42e$^+$), SEQ ID NO:6 (full length amino acid sequence of LXRα-42e$^+$), SEQ ID NO:7 (nucleotide sequence encoding the entirety of LXRα-42e$^-$), SEQ ID NO:8 (full length amino acid sequence of LXRα-42e$^-$), SEQ ID NO:16 (unique nucleotide sequence of LXRα-64 variant that connects exon 6 and 7 of wild type LXRα and creates a bigger exon 6 in LXRα-64 variant compared to exon 6 of the wild type LXRα), SEQ ID NO:17 (deduced amino acid sequence encoded by SEQ ID NO:16), SEQ ID NO:18 (unique nucleotide sequence of LXRα-42e that combines with exon 8 of wild type LXRα to create a longer exon 8 in LXRα-42e variants compared the exon 8 of wild type LXRα), and SEQ ID NO:19 (the deduced amino acid sequence encoded by SEQ ID NO:18).

The nucleic acids of the present invention can be produced by polymerase chain reaction (PCR). Such reactions are known to one of skill in the art, e.g., U.S. Pat. Nos. 4,754,065; 4,800,159; 4,683,195, and 4,683,202 provide PCR techniques and methods. These U.S. patents are hereby incorporated by reference in their entirety.

In another embodiment of the present invention, an LXRα-64, LXRα-42e$^+$ or LXRα-42e$^-$ nucleic acid molecule is a synthetic nucleic acid or a mimetic of a nucleic acid that may have increased bioavailability, stability, potency, or decreased toxicity compared to a naturally occurring LXRα variant. Such synthetic nucleic acids may have alterations of the basic A, T, C, G, or U bases or sugars that make up the nucleotide polymer to as to alter the effect of the nucleic acid.

LXRα variant and nucleic acid fragments derived from LXRα variants described herein can be used as reagents in isolation procedures, diagnostic assays, and forensic procedures. For example, sequences from an LXRα-64, LXRα-42e$^+$ or LXRα-42e$^-$ polynucleotide described herein to which they can hybridize (e.g., under stringent hybridization conditions) can be detectably labeled and used as a probe to isolate other sequences. In addition, sequences from an LXRα-64, LXRα-42e$^+$, or LXRα-42e$^-$ polynucleotide can be used to design PCR primers for use in isolation, diagnostic, or forensic procedures.

The LXRα-64, LXRα-42e$^+$, and LXRα-42e$^-$ nucleic acid molecules described herein can also be used to clone sequences located upstream of the LXRα variant sequences on corresponding genomic DNA. Such upstream sequences may be capable of regulating gene expression, and may include, e.g., promoter sequences, enhancer sequences, or other upstream sequences that influence transcription or translation levels. Once identified and cloned, these upstream regulatory sequences can be used in expression vectors designed to direct the expression of an inserted gene in a desired spatial, temporal, developmental, or quantitative fashion.

Sequences derived from polynucleotides described herein can be used to isolate the promoters of the corresponding genes using chromosome walking techniques. Chromosome walking techniques are known in the art, e.g., the GenomeWalker® kit available from BD Biosciences Clontech (Palo Alto, Calif.), which may be used according to the manufacturer's instructions.

Once the upstream genomic sequences have been cloned and sequenced, prospective promoters and transcription start sites within the upstream sequences may be identified by comparing the sequences upstream of the polynucleotides of the inventions with databases containing known transcription start sites, transcription factor binding sites, or promoter sequences.

In addition, promoters in the upstream sequences may be identified using promoter reporter vectors as follows: The expression of a reporter gene is detected when placed under the control of regulatory active polynucleotide fragment or variant of the LXRα-64, LXRα-42e$^+$ and LXRα-42e$^-$ promoter region located upstream of the first exon of the LXRα-64, LXRα-42e$^+$, or LXRα-42e$^-$ genes. Suitable promoter reporter vectors, into which the LXRα-64, LXRα-42e$^+$, or LXRα-42e$^-$ promoter sequences may be cloned include pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, beta-galactosidase, or green fluorescent protein. The sequences upstream an LXRα-64, LXRα-42e$^+$, or LXRα-42e$^-$ coding region are inserted into the cloning sites upstream of the reporter gene in both orientations and introduced into an appropriate host cell. The level of reporter protein is assayed and compared to the level obtained from a vector that lacks an insert in the cloning site. The presence of an elevated expression level by the vector containing the insert with respect to the control vector indicates the presence of a promoter in the insert. In some cases, the upstream sequences are cloned into vectors that contain an enhancer for increasing transcription levels from weak promoter sequences. A significant level of expression by the insert-containing vector above that observed for the vector lacking an insert indicates that a promoter sequence is present in the inserted upstream sequence. Promoter sequence within the upstream genomic DNA may be further defined by site directed mutagenesis, linker scanning analysis, or other techniques familiar to those in the art.

The strength and the specificity of the promoter of each LXRα-64, LXRα-42e$^+$ and LXRα-42e$^-$ gene can be assessed through the expression levels of a detectable polynucleotide operatively linked to the LXRα-64, LXRα-42e$^+$, or LXRα-42e$^-$ promoters in different types of cells and tissues. The detectable polynucleotide may be either a polynucleotide that specifically hybridizes with a predefined oligonucleotide probe, or a polynucleotide encoding a detectable protein, including LXRα-64, LXRα-42e$^+$ and LXRα-42e$^-$ polypeptides or fragments or variants thereof. This type of assay is well known to those skilled in the art. Some of the methods are discussed in more detail elsewhere in the application.

The promoters and other regulatory sequences located upstream of the polynucleotides of the inventions may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described herein. For example, if a promoter that confers a high level of expression in muscle is desired, the promoter sequence upstream of a polynucleotide of the invention derived from an mRNA that is expressed at a high level in muscle may be used in the expression vector.

Furthermore, nucleic acid fragments of the invention may be used to isolate and/or purify nucleic acids similar thereto using any methods well known to those skilled in the art including the techniques based on hybridization or on amplification described in this section. These methods may be used to obtain the genomic DNAs which encode the mRNAs from which the LXRα-64, LXRα-42e$^+$ and LXRα-42e$^-$ cDNAs are derived, mRNAs corresponding to LXRα-64, LXRα-42e$^+$ and LXRα-42e$^-$ cDNAs, or nucleic acids which are homologous to LXRα-64, LXRα-42e$^+$ and LXRα-42e$^-$ cDNAs or fragments thereof, such as variants, species homologues or orthologs.

Alternatively the nucleic acid fragments and genes of the present invention can be used as a reference to identify subjects (e.g., mammals, humans, patients) expressing decreases of functions associated with these receptors.

Vectors and Host Cells

The present invention relates to the vectors that include polynucleotides of the present invention, host cells that genetically engineered with vectors of the present invention such as cloning vector or expression vector and to the production of polypeptides of the present invention by recombinant techniques. For example, LXRα-64, LXRα-42e$^+$ and LXRα-42e$^-$ nucleic acid molecule could be linked to a vector. The vector may be a self-replicating vector or a replicative incompetent vector. The vector may be a pharmaceutically acceptable vector for methods of gene therapy.

The present invention further relates to a method of production of the polypeptides of the present invention by expressing polynucleotides encoding the polypeptides of the present invention in a suitable host and recovering the expressed products employing known recombinant techniques. The polypeptides of the present invention can also be synthesized using peptide synthesizers. Host cells can be engineered with the vectors of the present invention. The host organism (recombinant host cell) may be any eukaryotic or prokaryotic cell, or multicellular organism. Alternative embodiments can employ mammalian or human cells, especially embryonic mammalian and human cells. Suitable host cells include but are not limited to mammalian cells such as Human Embryonic Kidney cells (HEK 293), Human hepatoma cells (HepG2), Chinese hamster ovary cells (CHO), the monkey COS-1 cell line, the mammalian cell CV-1), amphibian cells (e.g., Xenopus egg cell). Yeast cells (*Saccharomyces cerevisiae, Schizosaccharomyces pombe, Pichia pastoris*), and insect cells. Furthermore, various strains of *E. coli* (e.g., DH5□ HB101, MC1061) may be used as host cells in particular for molecular biological manipulation.

The vectors may be cloning vectors or expression vectors such as in the form of a plasmid, a cosmid, or a phage or any other vector that is replicable and viable in the host cell. The engineered host cells can be cultured in conventional nutrient media modified as appropriate for activating promoters, selecting transformants or amplifying a polynucleotide of the present invention. The culture conditions such as pH, temperature, and the like, are those suitable for use with the host cell selected for expression of the polynucleotide are known to the ordinarily skilled in the art.

Plasmids generally are designated herein by a lower case "p" preceded and/or followed by capital letters and/or numbers, in accordance with standard naming conventions that are familiar to those of skill in the art. The plasmids herein are either commercially available, publicly available on unrestricted bases, or can be constructed from available plasmids by routine application of well-known, published procedures. Additionally, many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The appropriate DNA sequence may be inserted into the vector by a variety of the procedures known in the art.

The DNA sequence in the expression vector may be operatively linked to an appropriate expression control sequence(s) (promoter) to direct mRNA synthesis. Such promoters include but are not limited to SV40, human cytomegalovirus (CMV) promoters (e.g., pCMV/myc vectors, pcDNA 3.1 vector or any form of the pcDNA series), SP6, T7, and T3 RNA polymerase promoters. The expression vector may also include a ribosome binding site for translation initiation, a transcription terminator, and an appropriate sequence for amplifying the expression. The expression vector may also include one or more selectable marker genes to provide a specific phenotype for the selection of transformed host cells such as neomycin resistance for eukaryotic cells or ampicillin resistance for E. coli.

The expression vectors may include at least one selectable marker. Such markers include but are not limited to dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces, and Salmonella typhimurium cells; fungal cells, such as yeast cells; insect cells such as Drosophila S2 and Spodoptera Sf9 cells; animal cells such as CHO, Cos, and Bowes melanoma cells; and plant cells. Appropriate culture media and conditions for the above-described host cells are known in the art.

Illustrative examples of vectors for use in bacteria include, but are not limited to, pA2, pQE70, pQE60 and pQE-9, available from Qiagen (Valencia, Calif.); pBS vectors, Phagescript vectors, Bluescript™ vectors, pNH8A, pNH16a, pNH18A, pNH46A, available from Stratagene (Cedar Creek, Tex.); and pGEMEX®-1, pGEMEX®-2, PinPoint™ X series, pET-5 series, available from Promega (Madison, Wis.). Eukaryotic vectors include, but are not limited to, pWLNEO, pSV2CAT, pOG44, pXT1, and pSG, available from Stratagene; and pSVK3, pBPV, pMSG, and pSVL available from Pharmacia. Other suitable vectors will be apparent to the skilled artisan.

The gene can be placed under the control of a promoter, ribosome binding site (for bacterial expression), suitable gene control sequence, or regulatory sequences so that the DNA sequence encoding the protein is transcribed into RNA in the host cell transformed by a vector containing the expression construct. Such promoters include but are not limited to SV40, human cytomegalovirus (CMV) promoters (e.g., pCMV/myc vectors, pcDNA 3.1 vector or any form of the pcDNA series), SP6, T7, and T3 RNA polymerase promoters. In some cases it may be desirable to add sequences that cause the secretion of the polypeptide from the host cell, with subsequent cleavage of the secretory signal.

For some applications, it is desirable to reduce or eliminate expression of genes encoding a polypeptide of the present invention. To accomplish this, a chimeric gene or a chimeric construct designed for co-suppression of the instant polypeptide can be constructed by linking a gene or gene fragment encoding that polypeptide to a promoter sequences. Alternatively, a chimeric gene or chimeric construct designed to express antisense RNA for all or part of the instant nucleic acid fragment can be constructed by linking the gene or gene fragment in reverse orientation to a promoter sequences. Either the co-suppression or antisense chimeric genes can be introduced into desired host cell via transformation wherein expression of the corresponding endogenous genes are reduced or eliminated.

Polypeptides

LXRα variant polypeptides are useful for a variety of applications, including but not limited to producing antibodies (e.g., that specifically bind to an LXRα variant), modulating LXR wild type activity, and altering fatty acid and cholesterol metabolism (e.g., by modulating gene expression of enzymes that regulate fatty acid and cholesterol metabolism in a cell in which the LXRα variant is expressed). LXRα variant polypeptides are also useful for identifying compounds that differentially bind to LXRα wild type polypeptides and LXRα variant polypeptides. Such compounds are candidate compounds for differentially regulating metabolic activities associated with LXRα.

The polypeptides of the present invention can be produced by growing suitable host cells transformed by an expression vector described above under conditions whereby the polypeptide of interest is expressed. The polypeptides can then be isolated and purified. Methods purifying proteins from cell cultures are known in the art and include, but not limited to, ammonium sulfate precipitation, anion or cation exchange chromatography, and affinity chromatography.

Cell-free translation systems can also be employed to produce the polypeptides of the present invention using the RNAs derived from the polynucleotides of the present invention.

The polypeptides of the present invention can be produced by growing suitable host cells transformed by an expression vector (e.g., as described herein) under conditions whereby the polypeptide of the interest is expressed. The polypeptide may then be isolated and purified. Methods of the purification of proteins from cell cultures are known in the art and include but are not limited to ammonium sulfate precipitation, anion or cation exchange chromatography, and affinity chromatography.

Cell-free translation systems may also be employed to produce the polypeptides of the present invention using the RNAs derived from the polynucleotides of the present invention.

Large-scale production of cloned LXRα-64, LXRα-42e$^+$, and LXRα-42e$^-$ can enable the screening of large numbers of LXRα-64, LXRα-42e$^+$, and LXRα-42e$^-$ analogs, and can facilitate the development of new or improved agonists and antagonists for the treatment of lipid metabolism disorders. More specifically, the screening of large numbers of analogs for LXRα-64, LXRα-42e$^+$, and LXRα-42e$^-$ activity could lead to development of improved drugs affecting lipid metabolism. Lipid metabolism disorders and conditions include but are not limited to atherosclerosis, diabetes, obesity, Alzheimer's disease, inflammatory disorders, and hypercholesterolemia.

For some applications it is useful to direct a polypeptide described herein to different cellular compartments, or to facilitate secretion of a polypeptide from the cell. It is thus envisioned that the chimeric gene described above may be further supplemented by altering the coding sequence to encode the instant polypeptides with appropriate intracellular targeting sequences such as transit sequences added and/or with targeting sequences that are already present removed.

Furthermore, the polypeptides of the present invention or cells expressing them can be used as immunogen to prepare antibodies using methods known to those skilled in the art.

For example, a polypeptide encoded by SEQ ID NOS:3, 5, or 7 or a fragment thereof and/or a polypeptide encoded by SEQ ID NO:16 or 18, or cells expressing any of the aforementioned polypeptides can be used as immunogens. Of particular use are antibodies directed against the novel 64 amino acids of LXRα-64, which are not present in wild type LXRα. The antibodies can be polyclonal or monoclonal, and may include chimeric, single chain, and Fab fragments or the products of a Fab expression library. The antibodies are useful for detecting the polypeptide of the present invention in situ in cells or in vitro in cell extracts.

In addition, a polypeptide of the present invention can be used as a target to facilitate design and/or identification of compounds that may be useful as drugs (e.g., candidate compounds). In particular, these compounds may be used to treat diseases resulting from alterations in pathways such as bile acid synthesis, control of plasma lipoprotein composition, the transport of cholesterol from peripheral tissues to the liver, regulation of cell proliferation, differentiation, and apoptosis. In addition, the polypeptides of the present invention can be used to identify additional targets (e.g., co-activator or co-repressor proteins) that may influence LXRα. Various uses of the LXRα variants of the present invention include but are not limited to therapeutic modulation of pathophysiologic isoprenoid synthetic pathway, cholesterol metabolism, cholesterol catabolism, bile acid synthesis, and cell differentiation (e.g., gene delivery approaches, gene silencing approaches, protein therapeutics, antibody therapeutics), diagnostic utility, pharmaceutical drug targets, identification of receptor-based agonists or antagonists, and study of the molecular mechanisms of LXRα action.

Moreover, in cells with low LXRα activity due to phenotypic expression of endogenous dominant negative LXRα variants of the present invention, gene-silencing approaches such as antisense, siRNA (small interfering RNA), can be employed as strategies to induce or stimulate LXRα activity. Additionally, the novel variants of the present invention may be used to make fusion LXRα variants that may be employed toward the development of receptor-based agonists and antagonists.

Furthermore, the novel sequences of the present invention, e.g., SEQ ID NO:16, and SEQ ID NO:18, can be used to generate a dominant negative regulator of wild type LXRα. Nucleic acid molecules of SEQ ID NO:16 or 18 or fragments thereof can be incorporated into any one of the existing variants such as LXRα, and/or other nuclear receptors. The resulting new polypeptides comprising the amino acid sequence encoded by SEQ ID NO:16 and 18 or fragments thereof (e.g., the sequences set forth in SEQ ID NO:17 and 19) can generate a dominant negative regulator of wild type LXRα.

The importance of LXRs, and particularly LXRα to the delicate balance of cholesterol metabolism and fatty acid biosynthesis has led to the development of modulators of LXRs that are useful as therapeutic agents or diagnostic agents for the treatment of disorders associated with bile acid and cholesterol metabolism. The novel dominant negative LXRα variants of the present invention can be utilized to develop such therapeutic agents or diagnostic agents. Accordingly, an embodiment of the present invention is a method of treating a condition characterized by an aberrant or unwanted level of LXR (e.g., LXRα) expression, in a subject. The method includes providing the subject with a therapeutically effective amount of an LXRα-64, LXRα-42e$^+$, or LXRα-42e$^-$ protein, homologous proteins, or fragments of an LXRα variant protein having a desirable activity such as the ability to inhabit an LXRα variant activity, or any combination thereof that can modulate an LXRα activity. The proteins may be provided by introducing into LXRα-bearing cells of the subject, a nucleic acid sequence encoding an LXRα-64, LXRα-42e$^+$, or LXRα-42e$^-$ protein, homologous protein, or fragment, or any combinations thereof under conditions such that the cells express an LXRα-64, LXRα-42e$^+$, or LXRα-42e$^-$ protein, homologous protein, or fragment thereof resulting in modulation of wild type LXRα receptor and/or other nuclear receptors that heterodimerize with RXR. Examples of these receptors include but are not limited to LXRα, LXRβ, PPARα, PPARγ, PPARδ, RAR, XR, and PXR.

Introduction of an LXRα variant nucleic acid into cells of a subject may comprise a) treating cells of the subject or a cultured cell or tissue suitable for transplantation into the subject (e.g., a cultured stem cell line, bone marrow cells, umbilical cord blood cells) ex vivo to insert the nucleic acid sequence into the cells; and b) introducing the cells from step a) into the subject (e.g., U.S. Pat. Nos. 6,068,836 and 5,506,674).

The subject may be an animal such as a mammal (e.g., mouse, rat, non-human primate, dog, goat, or sheep). The mammalian subject can be a human.

LXRs function as heterodimers with the retinoid X receptors (RXRs). Moreover, RXRs are unique in their ability to function as both homodimeric receptors and as heterodimeric partners (e.g., LXRα, LXRβ, PPARα, PPARγ, PPARδ, RAR, XR, and PXR (Miyata et al., J. Biol. Chem., 271 9189-9192, 1996)) in multiple hormone responsive pathways. LXR variants of the present invention, LXR64, LXRα-42e$^+$, and LXRα-42e$^-$ can heterodimerize with RXR. Thus, for example, where LXR64, LXRα-42e$^+$, and/or LXRα-42e$^-$ variants are translated, RXR will heterodimerize with these variants rather than heterodimerizing with LXRα, LXRβ, PPARα, PPARγ, PPARδ, RAR, XR, and/or PXR, or homodimerizing with itself (RXR). This reduces the pool of RXR available for heterodimerization with specific nuclear receptors, and/or homodimerizing.

Therefore, as dominant negative variants, the novel LXRα-64, LXRα-42e$^+$, and LXRα-42e$^-$ of the present invention may be used for targeting specific receptors such as LXRα, LXRβ, PPARα, PPARγ, PPARδ, RAR, XR, or PXR. Accordingly, dominant negative LXRα variants of the present invention offer utility for therapeutic modulation of pathophysiologic conditions, diagnosis, risk for developing a disease, or treatment of a wide variety of disease states in which RXR, LXR, or other nuclear receptor (e.g., LXRα, LXRβ, PPARα, PPARγ, PPARδ, RAR, PXR, XR) mediate processes associated with the pathophysiologic condition or disease. Examples of such diseases are atherosclerosis, diabetes, obesity, cancer, and drug metabolism disorders.

Furthermore, LXRα variants of the present invention can modulate target gene expression or target gene product activity by interacting with wild-type LXRα binding partners such as RXR. LXR or RXR activity, as used herein, refers to modulation of LXR (e.g., LXRα) or RXR target gene expression or activity, respectively.

In one embodiment, target gene specificity of RXR-containing cells can be altered by contacting the cells with at least one of the novel LXRα variants of the present invention. In one specific embodiment, the RXR-containing cell, target genes operatively associated with response element(s) having the sequence 5'-AGGTTAnnnnTGGTCA-3' (SEQ ID NO:15), wherein each "n" is independently selected from A, G, T or C, can be activated by contacting the cells with at least one of the novel LXRα variants of the present invention.

The effect of LXRα variants of the present invention on homodimerization or heterodimerization processes can be determined using various methods known in the art. Examples of these methods are described in Terrillon et al. Molecular Endocrinology 2003, 17: 677-691, Germain-Desprez et al., J. Biol. Chem., 2003, 278 (25) 22367-22373, and Mercier et al., J. Biol. chem. 2002, 277 (47) 44925-44931. For example, the activity of RXR can be determined by quantitative assessment of RXR homodimerization or heterodimerization using any of the techniques in the above references. For example, nuclear receptor homo- and heterodimerization can be quantitated by fusing one of the nuclear receptors (e.g., an RXR) cDNA to the energy donor Rluc (*Renilla* luciferase) at the carboxyl terminus and fusing the second nuclear receptor (e.g., an LXRα) cDNA to the energy acceptor GFP (green fluorescent protein). Using BRET technology (Biosignal Packard), which allows separation between the *Renilla* luciferase and the green fluorescent protein emission spectra, the homo- and heterodimerization of the nuclear receptors can be quantitated.

Furthermore, the present invention relates to methods of reducing the expression of mammalian SREBP-1 genes. The invention is based on the discovery that LXRα variants, as dominant negatives, inhibit wild-type LXRα and correspondingly can inhibit SREBP-1 expression in mammalian cells. The latter conclusion can readily be confirmed by assessing SREBP-1 gene expression in the presence and absence of the variants of the present invention. Abnormal expression of SREBP-1 gene is involved in conditions such as lipodystrophy, hyperglyceremia, hypertriglyceridemia and diabetes. The variants of the present invention are useful not only for therapeutic and prophylactic treatment of conditions that are mediated by SREBP-1 over-expression, but are also useful for investigation of the mechanisms of fatty acid homeostasis, and the causes and mechanisms of lipodystrophy.

Antibodies

The invention also provides an isolated and purified antibody, e.g., a monoclonal antibody or polyclonal antibody, including an idiotypic or anti-idiotypic antibody, which is specific for a novel LXRα variant. The polypeptides of the present invention or cells expressing them may be used as immunogen to prepare antibodies by methods known to those skilled in the art. For example, these polypeptides encoded by SEQ ID NOS:3, 5, 7, 16, or 18 or any portion of SEQ ID NOS:3, 5, 7, 16, or 18 and/or encoded by SEQ ID NO:3, 5, 7, 16, or 18 or cells expressing any of the aforementioned polypeptides may be used as immunogens. These antibodies can be polyclonal or monoclonal and may include chimeric, single chain, and Fab fragments or the products of the Fab expression library. The antibodies are useful for detecting the polypeptide of the present invention in situ in cells or in vitro in cell extracts. In general, an antibody specifically binds to a specific peptide or molecule. By "specifically binds" or "selectively binds" is meant a molecule that binds to a particular entity, e.g., an LXRα variant polypeptide in a sample, but which does not substantially recognize or bind to other molecules in the sample, e.g., a biological sample, which includes the particular entity.

For example, the antibody may specifically recognize the novel 64 amino acids of the novel variant. Rabbits are immunized with a peptide comprising SEQ ID NO:4 or an immunogenic portion thereof, or a fusion peptide comprising SEQ ID NO:4, and polyclonal antisera specific for the novel variants isolated. Alternatively, spleen cells from immunized animals are fused to myeloma cells to produce hybridomas. The hybridomas are then screened to identify ones secreting a monoclonal antibody specific for a polypeptide or peptide comprising the 64 amino acid sequences of the novel LXRα-64 variant. These antibodies are useful to detect the novel LXRα-64 variants in biological samples, e.g., clinical samples, to detect the relative amount of the novel variant to other variant.

Screening Assays

In general, the new methods described herein include methods of identifying compounds that can modulate the expression or activity of an LXRα variant. In some cases, the compounds are identified that modulate the expression or activity of an LXRα variant and either do not affect, or affect to a lesser extent, the expression or activity of a wild type LXRα.

Also included are methods of producing LXRα (e.g., large-scale production) of cloned LXRα would enable the screening of relatively large numbers of LXRα analogs, and would facilitate the development of new or improved agonists and antagonists in the clinical therapy of -scale production of cloned LXRα would enable the screening of large numbers of LXRα related disorders such as lipid metabolism disorders. More specifically, the screening of large numbers of analogs for scale production of cloned LXRα would enable the screening of large numbers of LXRα activity could lead to development of improved tools and drugs for use in diagnosis and clinical therapy of, e.g., lipodystrophy, hypertriglyceridemia, hyperglyceremia, diabetes, or hypercholesterolemia.

In one embodiment, the polypeptides of the present invention are used as targets to facilitate design and/or identification of compounds that modulate the expression or activity of the polypeptides, e.g., by binding to a polypeptide. Such compounds are candidate compounds for treating disorders associated with LXRα-mediated pathways, e.g., can be used as drugs to regulate one or more aspects of an LXRα pathway. In particular, such compounds can be used to treat diseases resulting from alterations in hormone responsive pathways such as diabetes and drug metabolism disorders. In addition, the polypeptides of the present invention can be used to identify additional targets (e.g., co-activator or co-repressor proteins) that may influence hormone signaling. Various uses of the LXRα variants of the present invention include but are not limited to therapeutic modulation of pathophysiologic conditions involving aberrant lipid metabolism (e.g., gene delivery approaches, gene silencing approaches, protein therapeutics antibody therapeutics), diagnostic utility, pharmaceutical drug targets, identification of receptor-based agonists or antagonists, and study of the molecular mechanisms of LXRα action.

The systematic study of LXRα variants will make it possible to deduce structure-activity relationships for the proteins in question. Knowledge of these variants with respect to the disease studied is fundamental, since it makes it possible to understand the molecular cause of the pathology. Furthermore, the novel LXRα variants may be used for targeting of specific receptor interactions as a distinct approach in identification of tissue selective nuclear receptor modulators such as LXRα, LXRβ, PPARα, PPARγ, PPARδ, RAR, XR, and PXR.

Accordingly, the invention provides methods (also referred to herein as "screening assays") for identifying modulators, i.e., candidate compounds or agents (e.g., proteins, peptides, peptidomimetics, peptoids, small molecules, or other drugs) that bind to LXRα variant proteins, have a stimulatory or inhibitory effect on, for example, LXRα variant expression or activity, or have a stimulatory or inhibitory effect on, for example, the expression or activity of an LXRα variant substrate. Compounds thus identified can be used to modulate the activity of target gene products (e.g., LXRα variant genes) in a therapeutic protocol, to elaborate the biological function of the target gene product, or to identify compounds that disrupt normal target gene interactions.

In one embodiment, the invention provides assays for screening candidate or test compounds that are substrates of an LXRα variant protein or polypeptide or a biologically active portion thereof. In another embodiment, the invention provides assays for screening candidate or test compounds that bind to or modulate the activity of an LXRα variant protein or polypeptide or a biologically active portion thereof.

The test compounds of the present invention can be obtained, for example, using any of the numerous approaches in combinatorial library methods known in the art, including biological libraries; peptoid libraries (libraries of molecules having the functionalities of peptides, but with a novel, non-peptide backbone that are resistant to enzymatic degradation but that nevertheless remain bioactive; see, e.g., Zuckermann et al. (1994) J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner, supra), plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

In one embodiment, an assay is a cell-based assay in which a cell that expresses an LXRα variant protein or biologically active portion thereof is contacted with a test compound, and the ability of the test compound to modulate a LXRα variant activity is determined. Determining the ability of the test compound to modulate LXRα variant activity can be accomplished by monitoring, for example, dominant negative activity of the LXRα variant in a cell expressing a wild type LXRα, e.g., by monitoring the expression of an LXRα-inducible gene or gene product. The cell, for example, can be of mammalian origin, e.g., human.

The ability of the test compound to modulate LXRα variant binding to a compound, e.g., a naturally occurring LXRα variant ligand, or to bind to an LXRα variant can also be evaluated. This can be accomplished, for example, by coupling the compound with a radioisotope or enzymatic label such that binding of the compound to the LXRα variant can be determined by detecting the labeled compound in a complex. Alternatively, an LXRα variant can be coupled with a radioisotope, enzymatic label, or engineered to include a peptide label to monitor the ability of a test compound to modulate LXRα variant binding to, e.g., an LXRα variant, wild type LXRα, or heterodimerize with another member of the steroid receptor superfamily in a complex. For example, compounds can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound to interact with an LXRα variant, with or without the labeling of any of the interactants, can be evaluated. For example, a microphysiometer can be used to detect the interaction of a compound with an LXRα variant without the labeling of either the compound or the LXRα variant (e.g., McConnell et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and an LXRα variant.

In yet another method, a cell-free assay is provided in which an LXRα variant protein or biologically active portion thereof is contacted with a test compound and the ability of the test compound to bind to the LXRα variant protein or biologically active portion thereof is evaluated. Preferred biologically active portions of the LXRα variant proteins to be used in assays include fragments that participate in interactions with LXRα variant molecules, non-LXRα variant molecules (e.g., fragments with high surface probability scores), and predicted ligand binding domains of an LXRα variant.

Soluble and/or membrane-bound forms of isolated proteins (e.g., LXRα variant proteins or biologically active portions thereof) can be used in the cell-free assays of the invention.

Cell-free assays involve preparing a reaction mixture of the target gene protein and the test compound under conditions and for a time sufficient to allow the two components to interact and bind, thus forming a complex that can be removed and/or detected using methods known in the art.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the LXRα variant protein to bind to a target molecule can be accomplished using real-time Biomolecular Interaction Analysis (BIA) (e.g., Sjolander and Urbaniczky (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product (e.g., an LXRα variant protein or fragment thereof) or the test substance is anchored onto a solid phase. The target gene product/test compound complexes anchored on the solid phase can be detected at the end of the reaction. In general, the target gene product can be anchored onto a solid surface, and the test compound (which is not anchored) can be labeled, either directly or indirectly, with detectable labels discussed herein.

It may be desirable to immobilize an LXR(X variant, an anti-LXRα variant antibody, or its target molecule to facilitate separation of complexed from uncomplexed forms of one or both of the proteins, as well as to accommodate automation of the assay. Binding of a test compound to an LXRα variant protein, or interaction of an LXRα variant protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, glutathione-S-transferase/LXRα variant fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein or LXRα variant protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of LXRα variant binding or activity determined using standard techniques.

Other techniques for immobilizing either a LXRα variant protein or a target molecule on matrices include using conjugation of biotin and streptavidin. Biotinylated LXRα variant protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with an LXRα variant protein or target molecules but which do not interfere with binding of the LXRα variant protein to its target molecule. Such antibodies can be derivatized to the wells of the plate, and unbound target or LXRα variant protein trapped in the wells by antibody conjugation. Methods for detecting such complexes, in addition to those described above for the GST-immobilized complexes, include immunodetection of complexes using antibodies reactive with the LXRα variant protein or target molecule, as well as enzyme-linked assays that rely on detecting an enzymatic activity associated with the LXRα variant protein or target molecule.

Alternatively, cell free assays can be conducted in a liquid phase. In such an assay, the reaction products can be separated from unreacted components by any of a number of techniques known in the art, including but not limited to differential centrifugation (for example, Rivas and Minton, (1993) *Trends Biochem Sci* 18:284-7); chromatography (gel filtration chromatography, ion-exchange chromatography); electrophoresis (e.g., Ausubel et al., eds. *Current Protocols in Molecular Biology* 1999, J. Wiley: New York.); and immunoprecipitation (for example, Ausubel et al., eds. (1999) *Current Protocols in Molecular Biology*, J. Wiley: New York). Such resins and chromatographic techniques are known to one skilled in the art (e.g., Heegaard, (1998) J. Mol. Recognit. 11:141-8; Hage and Tweed, (1997) J. Chromatogr. B. Biomed. Sci. Appl. 699:499-525). Further, fluorescence energy transfer may also be conveniently utilized, as described herein, to detect binding without further purification of the complex from solution.

In some cases, the assay includes contacting the LXRα variant protein or biologically active portion thereof with a known compound that binds the LXRα variant (e.g., an LXRα, LXRα variant, or other member of the steroid receptor superfamily) to form an assay mixture, contacting the assay mixture with a test compound, and determining the ability of the test compound to interact with an LXRα variant protein, wherein determining the ability of the test compound to interact with an LXRα variant protein includes determining the ability of the test compound to preferentially bind to the LXRα variant or biologically active portion thereof, to disrupt the interaction between the LXRα variant and the known compound, or to modulate the activity of a target molecule, as compared to the known compound (e.g., by monitoring dominant negative activity of the LXRα variant).

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The target genes/products for use in this embodiment are generally the LXRα variant genes identified herein. In an alternative embodiment, the invention provides methods for determining the ability of the test compound to modulate the activity of an LXRα variant protein through modulation of the activity of a downstream effector of a LXRα variant target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In some methods, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the LXRα variant proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, that bind to or interact with an LXRα variant ("LXRα variant -binding proteins" or "LXRα variant-bp") and are involved in LXRα variant activity. Such LXRα variant-bps can be activators or inhibitors of signals (e.g., ligands) by the LXRα variant proteins or LXRα variant targets as, for example, downstream elements of a LXRα variant-mediated signaling pathway. Kits for performing such assays are commercially available (e.g., Stratagene, La Jolla, Calif.; BD Biosciences Clontech, Palo Alto, Calif.).

In another embodiment, modulators of LXRα variant expression are identified. For example, a cell or cell free mixture is contacted with a candidate compound and the expression of an LXRα variant mRNA or protein evaluated relative to the level of expression of the LXRα variant mRNA or protein in the absence of the candidate compound. When expression of the LXRα variant mRNA or protein is greater in the presence of the candidate compound than in its absence, the candidate compound is identified as a stimulator of LXRα variant mRNA or protein expression. Alternatively, when expression of the LXRα variant mRNA or protein is less (statistically significantly less) in the presence of the candidate compound than in its absence, the candidate compound is identified as an inhibitor of the LXRα variant mRNA or protein expression. The level of the LXRα variant mRNA or protein expression can be determined by methods described herein for detecting the LXRα variant mRNA or protein.

In another aspect, the invention pertains to a combination of two or more of the assays described herein. For example, a modulating agent can be identified using a cell-based or a cell free assay, and the ability of the agent to modulate the activity of an LXRα variant protein can be confirmed in vivo, e.g., in an animal such as an animal model for hypercholesterolemia, or other disorder related to fatty acid metabolism.

This invention further pertains to novel agents identified by the above-described screening assays. Accordingly, it is within the scope of this invention to further use an agent identified as described herein (e.g., an LXRα variant modulating agent, an antisense LXRα variant nucleic acid molecule, an LXRα variant-specific antibody, or an LXRα variant-binding partner) in an appropriate animal model to determine the efficacy, toxicity, side effects, or mechanism of action, of treatment with such an agent. Furthermore, novel agents identified by the above-described screening assays can be used for treatments as described herein.

Transgenic Animals

The invention also relates to non-human transgenic animals. Such animals are useful for studying the function and/or activity of an LXRα variant protein and for identifying and/or evaluating modulators of LXRα variant expression or activity. As used herein, a "transgenic animal" is a non-human animal, such as a mammal, e.g., a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which generally is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous LXRα variant gene has been altered by, e.g., by homologous recombination between the endogenous gene and an exogenous DNA molecule introduced into a cell of the animal, e.g., an embryonic cell of the animal, prior to development of the animal. In some cases the ortholog of the LXRα variant is identified in the animal and ortholog sequence is used to generate the transgenic animal. When homology is sufficient between the known (e.g., human) and LXRα variant gene of interest, the human sequence can be used.

Intronic sequences and polyadenylation signals can also be included in the transgene to increase the efficiency of expression of the transgene. A tissue-specific regulatory sequence(s) can be operably linked to a transgene of the invention to direct expression of an LXRα variant protein to particular cells. A transgenic founder animal can be identified based upon the presence of an LXRα variant transgene in its genome and/or expression of the LXRα variant mRNA in tissues or cells of the animals. Transgenic animals can also be identified by other characteristics associated with the transgene. For example, a transgenic animal expressing an LXRα-64 transgene will have a decreased amount of SREBP-1C expression, which is particularly notable in the presence of an LXRα agonist compared to a control animal. A transgenic founder animal can then be used to breed additional animals carrying the transgene. Moreover, transgenic animals carrying a transgene encoding an LXRα variant protein can further be bred to other transgenic animals carrying other transgenes.

LXRα variant proteins or polypeptides can be expressed in transgenic animals, e.g., a nucleic acid encoding the protein or polypeptide can be introduced into the genome of an animal. In general, the nucleic acid is placed under the control of a tissue specific promoter, e.g., a milk or egg specific promoter, and recovered from the milk or eggs produced by the animal. Suitable animals for this application include mice, pigs, cows, goats, and sheep.

The invention also includes a population of cells from a transgenic animal. Methods of isolating and propagating such cells are known in the art and include the development and propagation of primary, secondary, and immortalized cells.

EXAMPLES

The present invention is further defined in the following Examples, in which all parts and percentages are by weight and degrees are Celsius, unless otherwise stated. It should be understood that these Examples, while indicating examples of embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. The Examples are not to be construed as limiting the scope or content of the invention in any way.

Example 1

Cloning of Human LXR Variants

Total RNA was isolated from THP-1 cells (human monocyte-macrophage cell line using a QIAGEN Kit (QIAGEN, Valencia, Calif.). The first-strand cDNA was synthesized from 0.1 µg of total THP-1 RNA in a 20 µL reaction mixture containing 4 µL of 5XRT reaction buffer, 10 units of Rnasin, 200 µM dNTP, 20 µM random primer, and 20 units of reverse transcriptase. The mixture was incubated at 42° C. for 1 hour and then at 53° C. for 30 minutes. The unhybridized RNA was then digested with 10 units of RNase H at 37° C. for 10 minutes. Two µL of the reverse transcriptase products were subjected to PCR amplification using human LXRα-specific primers. The primer sequences were LXRα-For: 5'-CGGTCGACATGTCCTTGTGGCTGGGG (SEQ ID NO:9); and LXRα-Rev: 5'-CAGCGGCCGCTTCGTGCACATCCCAGATCTC (SEQ ID NO:10) (restriction sites are underlined). Thirty-five cycles of amplification were performed in a thermocycler at 94° C. (30 seconds), 58° C. (30 seconds), and 72° C. (2 minutes). The RT-PCR products were analyzed on a 1.2% agarose gel. The same amount of total RNA was used as a template in the PCR to verify that the band was amplified from cDNA. The RT-PCR products were sub-cloned into the Sal I/Nit I sites of pCMV expression vector for sequencing. The result of sequencing the subclones was the identification of a number of novel sequences, including those termed herein LXRα-64, LXRα-42e$^+$, AND LXRα-42e$^-$.

Example 2

Sequencing and Preliminary Analysis of the Clone

Using the LXRα-For and LXRα-Rev primers of Example 1 (supra), three alternative variants of human LXRα were identified and cloned from human monocyte/macrophage THP-1 cells. The variants-were LXRα-64, which was found to be 64 amino acids longer than the native (wild-type) LXRα; LXRα-42e$^+$, which has,42 amino acids different from native LXRα; and LXRα-42e$^-$, which has 42 amino acids different from native LXRα and the sequence corresponding to exon 6 of native LXRα is missing. The comparison of nucleotide sequences and predicted amino acid sequences of the new LXRα variants with wild-type human LXRα are shown in FIGS. 1B, 2B, and 3B.

FIG. 1A illustrates the novel nucleotide sequence that is present in LXRα-64 that is not present in wild type LXRα (nucleotides 1121-1154). FIG. 1B illustrates the novel amino acid sequence that is present in LXRα-64 that is not present in wild type LXRα (amino acids 368-409).

FIG. 2A illustrates the novel nucleotide sequence that is present in LXRα-42e$^+$. The missing sequence in LXRα-42e$^+$ that is present in wild type LXRα (nucleotides 1121-1154) introduces a frame shift. This results in a novel amino acid sequence in LXRα-42e$^+$(amino acids 368-409 of LXRα-42e$^+$). LXRα-42e$^+$ lacks the amino acid sequence corresponding to amino acids 368-447 of wild type LXRα-42e$^+$.

FIG. 3A depicts the complete sequence for LXRα-42e$^-$ from nucleotides 651-1220. This figure does not depict the entire sequence of wild type LXRα from the corresponding region (nucleotides 651-1166). The sequence corresponding to nucleotides 708-887 of wild type LXRα are not present in LXRα-42e$^-$. The sequence corresponding to nucleotides 1101-1134 of LXR-42e$^-$ is not present in wild type LXRα. FIG. 3B shows sequences that are present in wild type LXRα and not in LXRα42e$^-$ (amino acids 237-296 and 368-447 of wild type LXRα) and sequences that are present only in LXRα-42e$^-$ (amino acids 308-349 of LXRα-42e$^-$).

The entire cDNA coding region and the predicted amino acid sequence of the new variants are shown in SEQ ID NO:3 (nucleotide sequence coding for LXRα-64), SEQ ID NO:4 (deduced amino acid sequence of LXRα-64), SEQ ID NO:5 (nucleotide sequence coding for LXRα-42e$^+$ cDNA), SEQ ID NO:6 (deduced amino acid sequence of LXRα-42e$^+$), SEQ ID NO:7 (nucleotide sequence coding for LXRα-42e$^-$), SEQ ID NO:8 (deduced amino acid sequence of LXRα-42e$^-$), SEQ ID NO:16 (unique nucleotide sequence of LXRα-64 that connects exons 6 and 7 of wild type LXRα, derived from intron 6, creating a larger exon 6), SEQ ID NO:17 (unique amino acid sequence in LXRα-64 and encoded by SEQ ID NO:16), SEQ ID NO:18 (the novel portion of exon 8 in LXRα-42e mRNAs that is not present in exon 8 of wild-type LXRα, and SEQ ID NO:19 (deduced amino acid sequence encoded by the additional sequence identified in LXRα-42 cDNAs).

Example 3

Gene Characterization

The genomic organization of the novel variants of the present invention, LXRα-64, LXRα-42$^+$ and LXRα-42$^-$, was determined. Transcription start sites, genomic structure, alternative splicing, and functional domains of the LXRα-64, LXRα-42$^+$ and LXRα-42$^-$ and their comparison with wild type LXRα are described in FIGS. 4, 5, and 6 respectively.

FIG. 4 diagrams the structure of LXRα-64 mRNA, showing that novel sequence is incorporated into sequence corresponding to exon 6 of wild type LXRα. Therefore, a probe having the novel sequence is useful for, e.g., identifying the expression of an LXRα-64 or identifying LXRα-64 variants. The amino acid sequence encoded by the novel sequence can be used as an antigen to generate an antibody that specifically binds to LXRα-64 variants. It is a characteristic of LXRα-64 variants that their mRNAs contain the novel sequence nucleic acid sequence and encode the novel amino acid sequence. Such variants may contain conservative substitutions.

FIG. 5 diagrams the structure of LXRα-42e$^+$ mRNA, showing that novel sequence is incorporated into sequence corresponding to exon 8 of wild type LXRα, the sequence introducing a stop signal into the sequence preceding exon 9. The new LXRα-42e$^+$ sequence also lacks exon 10 of wild type LXRα. A probe having the novel sequence is useful for, e.g., identifying the expression of an LXRα-42e$^+$ or identifying LXRα-42e$^+$ variants. It is a characteristic of LXRα-42e$^+$ variants that their mRNAs contain the novel nucleic acid sequence and encode the novel amino acid sequence. Such variants may contain conservative substitutions. Certain LXRα-42e$^+$ variants lack exon 10. In some cases an LXRα-42e$^+$ variant contains both the novel sequence and lacks exon 10.

FIG. 6 diagrams the structure of LXRα-42e$^-$ mRNA, showing that exon 6 of wild type LXRα is absent in LXRα-42e$^-$. (Some reports of wild type LXRα designate exon 1 as exon 1 A and exon 2 as exon 1 B. Under this terminology, exon 5 of the wild type LXRα corresponds to the missing exon 6 sequence.) A probe that includes the contiguous exon 5 and exon 7 sequence of LXRα-42e$^-$ is therefore useful, e.g., for specifically detecting expression of this sequence or for identifying novel variants of LXRα-42e$^-$. Accordingly, a characteristic of an LXRα-42e$^-$ variant is the lack of wild type exon 6. An amino acid sequence that is encoded by the sequence bridging exons 5 and 7 is also useful for generating an antibody that specifically binds to an LXRα-42e$^-$.

Example 4

Tissue Distribution

Tissue distribution studies were performed using real-time PCR and Multiple Tissue cDNA panels (MTC, human cDNA) from BD Biosciences Clontech (Palo Alto, Calif.). Real-time quantitative PCR assays were performed on the panels using an Applied Biosystems 7700 sequence detector (Foster City, Calif.). Each amplification mixture (50 μL) contained 50 ng of cDNA, 400 nM forward primer (SEQ ID NO:11), 400 nM reverse primer (SEQ ID NO:12), 200 nM dual-labeled fluorogenic probe (SEQ ID NO:13) (Applied Biosystems), 5.5 mM MgCl$_2$, and 1.25 units Gold Taq (Applied Biosystems). The primers amplify a portion of the LXRα sequences that is about 80 nucleotides in length. The PCR thermocycling parameters were 95° C. for 10 minutes, and 40 cycles at 95° C. for 15 seconds, and 60° C. for 1 minute. Together with the samples and no-template controls, a serially diluted cDNA standard was analyzed in parallel. All samples were analyzed for human glyceraldehyde-3-phosphate dehydrogenase (GAPDH) expression in parallel in the same run using probe and primers from predeveloped assays for GAPDH (Applied Biosystems). All of the target gene expression was normalized to the expression of GAPDH. Quantitative analysis was performed using the threshold procedure, following the manufacturer's protocol (Perkin-Elmer), and relative amounts were calculated from the standard curve.

The primers and probe used to detect LXRα variant LXRα-64 in these studies were as follows: L64-For (5'-TGGGAAGCAGGGATGAGG-3'; SEQ ID NO:11), L64-Rev (5'-GAGGGCTGGTCTTGGAGCA-3'; SEQ ID NO:12), and L64 TaqMan probe (FAM-TCGGCCTC-CCTGGAAGAGGCC-TAMRA; SEQ ID NO:13). The L64 primers and probe are localized to the 64 nucleotides that are found in the LXRα-64 cDNA.

LXRα-64 mRNA was found to be most abundantly expressed in liver (FIG. 7A). Transcripts were also detected at a relatively high level in small intestine, placenta, pancreas, ovary, and colon. Very little expression was observed in the other tester tissues. The primers and probe used to detect LXRα variant LXRα-42 in these studies were as follows: L42-For (5'-GGTGGAGGCATTTGCTGTGT-3'; SEQ ID NO:21), L42-Rev (5'-CCCAAATTGCAAC-CAAAATATAGA-3'; SEQ ID NO:22) and L42 probe (FAM-TTTAGGATGAGAGAGCTTGGCTGGAGCAT-TAMRA; SEQ ID NO:23). FAM/TAMRA fluorogenic probes are available from BioSearch Technologies (Novato, Calif.).

The expression of LXRα-42 had different pattern compared to LXRα-64. While the most abundant expression was observed in liver, the LXRα-42 sequences were detected only at low levels or were absent in the other tissues tested.

Wild type LXRα as well as LXRα variants are highly expressed in liver. Next to liver, wild type LXRα is present in the greatest abundance in pancreas followed by testis, small intestine, and spleen, which share similar levels of mRNA. Prostate, thymus, kidney, ovary, placenta, lung, and colon express less than testis, while leukocyte, heart, brain, and skeletal muscle contain negligible amounts of wild type LXRα mRNA. LXRα-64 is also expressed at the highest level in liver followed by small intestine. Placenta, pancreas, ovary, colon, and lung express less LXRα-64 than small intestine. Expression was observed to be even lower in kidney and leukocyte, while heart, brain, skeletal muscle, spleen, thymus, prostate, and testis contained negligible amounts of expression. LXRα-42 expression (LXRα-42e$^-$ plus LXRα-42e$^+$) in lung was lower than in liver. The remaining tissues (discussed supra) had significantly lower levels of expression compared to liver.

Example 5

Upregulation of LXRα-L64 by LXR Agonists in dTHP-1 Cells

Experiments were performed to determine whether agonists of wild type LXRα could also regulate the expression of LXRα variants. In these experiments, THP-1 cells were obtained from the American Type Culture Collection (ATCC) and cultured in RPMI medium containing 10% fetal bovine serum (FBS). For gene expression analysis in differentiated THP-1 cells, the THP1 cells were incubated in RPMI medium supplemented with 10% lipoprotein-deficient serum (LPDS) (Intracel Corp, Rockville, Md.) and treated with 150 nM phorbol ester for 3 days followed by treatment with LXR, RXR, or Peroxisome Proliferator-activated Receptor γ (PPARγ) agonist compounds, specifically with vehicle only (control), 10 μM T0901317, 10 μM GW 3965, 10 μM Ciglitazone, or 1 μM 9RA. The primers and TaqMan probe for the real-time RT-PCR was described as in Example 4. The data showed that expression of LXRα-64 and LXRα-42 mRNAs was increased in THP-1 cells incubated with either of the two synthetic LXR agonists T0901317 ([N-(2,2,2,-trifluoro-ethyl)-n-[4-(2,2,2,-trifluoro-1-hydroxy-1-trifluoromethyl-ethyl)-phenyl]-benzene-sulfonamide]) (Repa et al., Science 2000 289(5484):1524-9, and Schultz et al., Genes Dev. 2000 14(22):2831-8), GW3965 [3-(3-(2-chloro-3-trifluoromethylbenzyl-2,2-diphenylethylamino)propoxy)phenylacetic acid] (Collins et al., J. Med. Chem., 2002 45: 1963-1966 and Laffitte et al., Mol. Cell. Biol. 2001, 21: 7558-7568), PPARγ ligand (10 μM of citglitazone), and RXR ligand (9-cis retinoic acid) (FIGS. 8A and 8B).

These data demonstrate that expression of LXRα variants can be induced using known LXRα agonists.

Example 6

Functional Characterization of LXRα Variants

Human LXRα promoter (SEQ ID NO:14) was amplified by PCR using information from the published LXRα genomic structure and sequence (GenBank accession no. AC090589. A fragment spanning from −2660 to −2363 (relative to the transcription start site from exon 1) of LXRα promoter which contains the LXR response element (5'-TGACCAgcagTAACCT-3', SEQ ID NO:20) (Laffitte et al. 2001, Mol. Cell. Biol. 21, 7558-7568 and Whitney et al., 2001, J. Biol. Chem. 276, 43509-43515) of LXRα was subcloned into pGL3 basic plasmid to create pGL-3-LXRα-Luc. The GenBank accession number of the LXRα "native" sequence used as a reference for the experiments and analysis disclosed herein is Genbank accession number for human LXRα is BC008819. Coding regions of human LXRα, and RXRα (GenBank accession number BC007925) were amplified by RT-PCR according to the sequences in GenBank and subcloned into pCMV/myc/nuc expression vectors (Invitrogen, Carlsbad, Calif.). The new LXRα-L64 coding region was subcloned into pCMV/myc/nuc expression vectors.

HEK 293 cells were grown in Dulbecco's modified Eagle's medium (DMEM) containing 10% FBS. Transfections were performed in triplicate in 24 well plates using Lipofectamine 2000 (Invitrogen). Each well was transfected with 400 ng of reporter plasmid, 100 ng of receptor expression vector, and 200 ng of pCMV-βgal reference plasmid containing a bacterial β-galactosidase gene. Additions to each well were adjusted to contain constant amounts of DNA and of pCMV (Invitrogen, Carlsbad, Calif.) expression vector. After six to eight hours following transfection, the cells were washed once with phosphate-buffered saline (PBS), and then incubated with fresh medium containing 10% lipoprotein-deficient serum (LPDS) (Intracel Corp, Rockville, Md.) and an LXR agonist, RXR agonist, or vehicle control for 24 hours. The cells were harvested, analyzed, and the extracts were assayed for luciferase and β-galactosidase activity in a microplate luminometer/photometer reader (Lucy-1; Anthos, Salzburg, Austria). Luciferase activity was normalized to β-galactosidase activity.

In more detail, HEK 293 cells were contransfected with either control pGL3-basic vector (Promega Madison, Wis. 53711) or pGL3-LXRα-Luc (part of LXRα promoter containing the LXRE sequence of LXRα promoter (TGAC-CAgcagTAACCT; SEQ ID NO:20) was subcloned into Kpn I/Xho I sites of pGL3-basic vector) reporters with pCMV-h LXRα/pCMV-hRXRα, pCMV-LXRα-64/pCMV-hRXRα, pCMV-LXRα-42e+/pCMV-hRXRα, pCMV-LXRα-42e−/pCMV-hRXRα respectively. Following transfection, cells were incubated for 24 hours in DMEM supplemented with 10% lipoprotein-deficient serum (LPDS) and 10 µM T0901317 or vehicle control then luciferase activity assayed and normalized.

As shown in FIG. 9, when the new LXRα variants were co-transfected with the reporter gene, the LXR ligand-dependent activation was sharply decreased as compared with the co-transfected native LXRα. Furthermore, as shown in FIG. 10, when the variants and LXRα were simultaneously co-transfected with the reporter gene, the activation of exogenous LXRα was inhibited as compared with LXRα co-transfected along. These data indicated that the newly cloned LXRα variants can function as dominant negative regulators of native LXRα expression.

Example 7

Regulation of LXR Target Genes by LXR Variant

An important feature of LXRα is its involvement in multiple physiologic effects, some of which are advantageous to an organism and some of which are, at least in certain cases, deleterious to the organism. Thus, the discovery described herein of new LXRα variants provides targets to permit the differential regulation of different aspects of LXRα activity in a cell. To determine the function of the variants, the expression of LXR target genes in the presence of an expressed LXRα variant was examined.

In these experiments, coding regions of human LXRα, RXRα, and the LXRα variant (LXRα-64) were amplified by RT-PCR. The PCR products were subcloned into pCMV/myc/nuc expression vectors (Invitrogen, Carlsbad, Calif.) and used in the experiments described infra.

Expression experiments were conducted in HEK 293 cells that were propagated in Dulbecco's modified Eagle's medium (DMEM) containing 10% FBS. The cultured cells were transfected with either the expression vector containing a sequence encoding LXRα (wild type) or an expression vector encoding LXRα-64. All samples were co-transfected with an expression vector encoding an RXRα sequence. Transfections were performed in triplicate in 24 well plates using the Lipofectamine 2000 (Invitrogen, Carlsbad, Calif.). Each well was transfected with 200 ng of the LXRα expression vector (LXRα), the LXRα-64 expression vector (L64), or control plasmid (pCMV) along with 200 ng of human RXRα expression vector (RXRα). Additions to each well were adjusted to contain constant amounts of DNA and of pCMV expression vector. Six to eight hours following transfection, the cells were washed once with phosphate-buffered saline (PBS), then incubated with fresh medium containing 10% lipoprotein-deficient serum (LPDS) (Intracel Corp, Rockville, Md.) and a synthetic LXR agonist (TO901317) and/or RXR agonist (9-cis-retinoic acid, 9RA), or vehicle only (control) for 48 hours. The cells were then harvested and total RNA was isolated from the cells using a QIAGEN kit. The levels of gene expression were determined with Real-time quantitative PCR assays using an Applied Biosystems 7700 sequence detector.

When a sequence encoding the new variant, LXRα-64, was cotransfected with human RXRα-encoding sequence and expressed in HEK 293 cells, basal, LXR ligand-dependent, and LXR+RXR ligand-dependent induction of SREBP-c1 (an LXR target gene) expression was sharply decreased compared to expression of SREBP-c1 in cells transfected with either wild type LXRα with RXRα or empty expression vector with RXR α (FIG. 11). The basal expression of another LXR target gene, ABCA1 was not affected by the introduction of the variant L64 with RXRα into the cells. However, LXR as well as LXR+RXR-ligand dependent induction of ABCA1 expression was less in cells expressing LXRα-64 and RXRα compared to expression in cells transfected with native LXRa and RXRa or empty expression vector with RXRa. (FIG. 12).

These data demonstrate that the LXRα variants can differentially regulate the expression of LXR target genes in HEK 293 cells, serving as dominant negative modulators of LXRα-induced gene expression. Thus, regulating expression or activity of an LXRα variant provides a method of differentially regulating LXRα-associated effects in cells.

These data also demonstrate that over expressing an LXRα variant can inhibit SREBP-C1 expression. Also, induction of expression of SREBP-1C by an LXR agonist is significantly decreased in a cell expressing an LXRα variant (e.g., LXRα-64. Therefore, increasing the expression or activity of an LXRα variant (e.g., LXRα-64) is useful for treating disorders associated with the expression of SREBP-1C. For example, disrupting the activity of an LXRα, e.g., by over expressing an LXRα-64 or increasing the activity of an LXRα-64 that is expressed in a cell (e.g., by administering a compound that differentially binds to LXRα-64 compared to wild type LXRα) can provide a method of inhibiting the insulin induction of SREBP-1C, and therefore provides a method of inhibiting undesirable induction of fatty acid synthesis by insulin. In another example, over expressing an LXRα variant (e.g., LXRα-64) or selectively activating an LXRα variant (for example, with a compound that differentially binds to the LXRα-variant) can result in inhibition of SREBP-1C, and therefore provides a method of treating hypertriglyceridemia, which is a condition that is a strong predictor of heart disease. In another example, lowered SREBP-1C expression (by increased expression or activity of an LXRα variant such as LXRα-64) can result in lower expression of VLDL-TGs (very low density lipoprotein triglycerides), a desirable effect in certain disorders such as diabetes and certain types of hyperlipoproteinemia.

Wild type LXR expression in the presence of an LXR agonist has the effect of upregulating ABCA1, which is involved in reverse cholesterol transport. Expression of an LXRα variant (e.g., LXRα-64) has little apparent effect on cellular processes. Therefore, overexpression of an LXRα variant can be beneficial in that it decreases expression of a particular LXRα target gene (e.g., SREBP-1C) but does not affect another LXRα target gene whose expression may be desirable (e.g., ABCA1).

Nuclear receptors that heterodimerize with RXR and activation of these heterodimers results in increased expression of specific genes. In the case of undesirable expression of one or more of these genes (e.g., LXR-mediated upregulation of SREBP1c), then overexpression of an LXRα-64 can be beneficial to a subject if expression of the LXRα variant binds to the RXR, thereby decreasing the availability of the RXR for heterodimerization and therefore reducing induction undesirable gene expression.

Sequences

SEQ ID NO:1 cDNA of the Entire Coding Region of Wild Type LXRα

```
   1 atgtccttgt ggctgggggc ccctgtgcct gacattcctc ctgactctgc
  51 ggtggagctg tggaagccag gcgcacagga tgcaagcagc caggcccagg
 101 gaggcagcag ctgcatcctc agagaggaag ccaggatgcc ccactctgct
 151 gggggtactg caggggtggg gctggaggct gcagagccca cagccctgct
 201 caccagggca gagccccctt cagaacccac agagatccgt ccacaaaagc
 251 ggaaaaaggg gccagccccc aaaatgctgg ggaacgagct atgcagcgtg
 301 tgtggggaca aggcctcggg cttccactac aatgttctga gctgcgaggg
 351 ctgcaaggga ttcttccgcc gcagcgtcat caagggagcg cactacatct
 401 gccacagtgg cggccactgc cccatggaca cctacatgcg tcgcaagtgc
 451 caggagtgtc ggcttcgcaa atgccgtcag gctggcatgc gggaggagtg
 501 tgtcctgtca gaagaacaga tccgcctgaa gaaactgaag cggcaagagg
 551 aggaacaggc tcatgccaca tccttgcccc ccaggcgttc ctcacccccc
 601 caaatcctgc cccagctcag cccggaacaa ctgggcatga tcgagaagct
 651 cgtcgctgcc cagcaacagt gtaaccggcg ctccttttct gaccggcttc
 701 gagtcacgcc ttggcccatg gcaccagatc cccatagccg ggaggcccgt
 751 cagcagcgct ttgcccactt cactgagctg gccatcgtct ctgtgcagga
 801 gatagttgac tttgctaaac agctacccgg cttcctgcag ctcagccggg
 851 aggaccagat tgccctgctg aagacctctg cgatcgaggt gatgcttctg
 901 gagacatctc ggaggtacaa ccctgggagt gagagtatca ccttcctcaa
 951 ggatttcagt tataaccggg aagactttgc caaagcaggg ctgcaagtgg
1001 aattcatcaa ccccatcttc gagttctcca gggccatgaa tgagctgcaa
1051 ctcaatgatg ccgagtttgc cttgctcatt gctatcagca tcttctctgc
1101 agaccggccc aacgtgcagg accagctcca ggtggagagg ctgcagcaca
1151 catatgtgga agccctgcat gcctacgtct ccatccacca tccccatgac
1201 cgactgatgt tcccacggat gctaatgaaa ctggtgagcc tccggaccct
1251 gagcagcgtc cactcagagc aagtgtttgc actgcgtctg caggacaaaa
1301 agctcccacc gctgctctct gagatctggg atgtgcacga atga
```

SEQ ID NO:2

The Deduced Amino Acid Sequence of Wild Type LXRα

```
  1 MSLWLGAPVP DIPPDSAVEL WKPGAQDASS QAQGGSSCIL REEARMPHSA
 51 GGTAGVGLEA AEPTALLTRA EPPSEPTEIR PQKRKKGPAP KMLGNELCSV
101 CGDKASGFHY NVLSCEGCKG FFRRSVIKGA HYICHSGGHC PMDTYMRRKC
151 QECRLRKCRQ AGMREECVLS EEQIRLKKLK RQEEEQAHAT SLPPRRSSPP
201 QILPQLSPEQ LGMIEKLVAA QQQCNRRSFS DRLRVTPWPM APDPHSREAR
251 QQRFAHFTEL AIVSVQEIVD FAKQLPGFLQ LSREDQIALL KTSAIEVMLL
301 ETSRRYNPGS ESITFLKDFS YNREDFAKAG LQVEFINPIF EFSRAMNELQ
```

-continued

```
351 LNDAEFALLI AISIFSADRP NVQDQLQVER LQHTYVEALH AYVSIHHPHD
401 RLMFPRMLMK LVSLRTLSSV HSEQVFALRL QDKKLPPLLS EIWDVHE*
```

SEQ ID NO:3

The cDNA Sequence that Codes for LXRα-64

```
   1 atgtccttgt ggctgggggc ccctgtgcct gacattcctc ctgactctgc
  51 ggtggagctg tggaagccag gcgcacagga tgcaagcagc caggcccagg
 101 gaggcagcag ctgcatcctc agagaggaag ccaggatgcc ccactctgct
 151 gggggtactg caggggtggg gctggaggct gcagagccca cagccctgct
 201 caccagggca gagccccctt cagaacccac agagatccgt ccacaaaagc
 251 ggaaaaaggg gccagccccc aaaatgctgg ggaacgagct atgcagcgtg
 301 tgtggggaca aggcctcggg cttccactac aatgttctga gctgcgaggg
 351 ctgcaaggga ttcttccgcc gcagcgtcat caagggagcg cactacatct
 401 gccacagtgg cggccactgc cccatggaca cctacatgcg tcgcaagtgc
 451 caggagtgtc ggcttcgcaa atgccgtcag gctggcatgc gggaggagtg
 501 tgtcctgtca gaagaacaga tccgcctgaa gaaactgaag cggcaagagg
 551 aggaacaggc tcatgccaca tccttgcccc ccaggcgttc ctcacccccc
 601 caaatcctgc cccagctcag cccggaacaa ctgggcatga tcgagaagct
 651 cgtcgctgcc cagcaacagt gtaaccggcg ctccttttct gaccggcttc
 701 gagtcacgcc ttggcccatg gcaccagatc cccatagccg ggaggcccgt
 751 cagcagcgct ttgcccactt cactgagctg gccatcgtct ctgtgcagga
 801 gatagttgac tttgctaaac agctacccgg cttcctgcag ctcagccggg
 851 aggaccagat tgccctgctg aagacctctg cgatcgaggt ggctggagaa
 901 gggcaaggga tgaagggaga agcagagtgg gattatctgt gggagggggcc
 951 tccagacatc gagctgggag agccaaatct gctgggaagc agggatgagg
1001 agaatcggcc tccctggaag aggccatgct ccaagaccag ccctcctagt
1051 ccccgtttga ggtttgctgc ttgtgtgcag gtgatgcttc tggagacatc
1101 tcggaggtac aaccctggga gtgagagtat caccttcctc aaggatttca
1151 gttataaccg ggaagacttt gccaaagcag ggctgcaagt ggaattcatc
1201 aacccatct cgagttctc cagggccatg aatgagctgc aactcaatga
1251 tgccgagttt gccttgctca ttgctatcag catcttctct gcagaccggc
1301 ccaacgtgca ggaccagctc caggtggaga ggctgcagca cacatatgtg
1351 gaagccctgc atgcctacgt ctccatccac catccccatg accgactgat
1401 gttcccacgg atgctaatga aactggtgag cctccggacc ctgagcagcg
1451 tccactcaga gcaagtgttt gcactgcgtc tgcaggacaa aaagctccca
1501 ccgctgctct ctgagatctg ggatgtgcac gaatga
```

SEQ ID NO:4

The Deduced Amino Acid Sequence of LXRα-64

```
  1 MSLWLGAPVP DIPPDSAVEL WKPGAQDASS QAQGGSSCIL REEARMPHSA
 51 GGTAGVGLEA AEPTALLTRA EPPSEPTEIR PQKRKKGPAP KMLGNELCSV
101 CGDKASGFHY NVLSCEGCKG FFRRSVIKGA HYICHSGGHC PMDTYMRRKC
151 QECRLRKCRQ AGMREECVLS EEQIRLKKLK RQEEEQAHAT SLPPRRSSPP
201 QILPQLSPEQ LGMIEKLVAA QQQCNRRSFS DRLRVTPWPM APDPHSREAR
251 QQRFAHFTEL AIVSVQEIVD FAKQLPGFLQ LSREDQIALL KTSAIEVAGE
301 GQGMKGEAEW DYLWEGPPDI ELGEPNLLGS RDEENRPPWK RPCSKTSPPS
351 PRLRFAACVQ VMLLETSRRY NPGSESITFL KDFSYNREDF AKAGLQVEFI
401 NPIFEFSRAM NELQLNDAEF ALLIAISIFS ADRPNVQDQL QVERLQHTYV
451 EALHAYVSIH HPHDRLMFPR MLMKLVSLRT LSSVHSEQVF ALRLQDKKLP
501 PLLSEIWDVH E*
```

SEQ ID NO:5

The cDNA Sequence of the Coding Region of LXRα-42e$^+$

```
   1 atgtccttgt ggctgggggc ccctgtgcct gacattcctc ctgactctgc
  51 ggtggagctg tggaagccag gcgcacagga tgcaagcagc caggcccagg
 101 gaggcagcag ctgcatcctc agagaggaag ccaggatgcc ccactctgct
 151 gggggtactg cagggtgggg gctggaggct gcagagccca cagccctgct
 201 caccagggca gagccccctt cagaacccac agagatccgt ccacaaaagc
 251 ggaaaaaggg gccagccccc aaaatgctgg ggaacgagct atgcagcgtg
 301 tgtggggaca aggcctcggg cttccactac aatgttctga gctgcgaggg
 351 ctgcaaggga ttcttccgcc gcagcgtcat caagggagcg cactacatct
 401 gccacagtgg cggccactgc cccatggaca cctacatgcg tcgcaagtgc
 451 caggagtgtc ggcttcgcaa atgccgtcag gctggcatgc gggaggagtg
 501 tgtcctgtca gaagaacaga tccgcctgaa gaaactgaag cggcaagagg
 551 aggaacaggc tcatgccaca tccttgcccc ccaggcgttc ctcaccccc
 601 caaatcctgc cccagctcag cccggaacaa ctgggcatga tcgagaagct
 651 cgtcgctgcc cagcaacagt gtaaccggcg ctccttttct gaccggcttc
 701 gagtcacgcc ttggcccatg caccagatc cccatagccg ggaggcccgt
 751 cagcagcgct tgcccactt cactgagctg gccatcgtct ctgtgcagga
 801 gatagttgac tttgctaaac agctacccgg cttcctgcag ctcagccggg
 851 aggaccagat tgccctgctg aagacctctg cgatcgaggt gatgcttctg
 901 gagacatctc ggaggtacaa ccctgggagt gagagtatca ccttcctcaa
 951 ggatttcagt tataaccggg aagactttgc caaagcaggg ctgcaagtgg
1001 aattcatcaa ccccatcttc gagttctcca gggccatgaa tgagctgcaa
1051 ctcaatgatg ccgagtttgc cttgctcatt gctatcagca tcttctctgc
1101 aggtgtggag gaggggcaat gggaaacagc aagagactta caccaaggag
```

```
1151 ggctgcaggt cccacaggaa tcggtggggg gagggggtg gtggcttggg 1201 agggtggagg catttgctgt gttattttag
```

SEQ ID NO:6

The Deduced Amino Acid Sequence of LXRα-42e+

```
  1 MSLWLGAPVP DIPPDSAVEL WKPGAQDASS QAQGGSSCIL REEARMPHSA

51 GGTAGVGLEA AEPTALLTRA EPPSEPTEIR PQKRKKGPAP KMLGNELCSV

101 CGDKASGFHY NVLSCEGCKG FFRRSVIKGA HYICHSGGHC PMDTYMRRKC

151 QECRLRKCRQ AGMREECVLS EEQIRLKKLK RQEEEQAHAT SLPPRRSSPP

201 QILPQLSPEQ LGMIEKLVAA QQQCNRRSFS DRLRVTPWPM APDPHSREAR

251 QQRFAHFTEL AIVSVQEIVD FAKQLPGFLQ LSREDQIALL KTSAIEVMLL

301 ETSRRYNPGS ESITFLKDFS YNREDFAKAG LQVEFINPIF EFSRAMNELQ

351 LNDAEFALLI AISIFSAGVE EGQWETARDL HQGGLQVPQE SVGGGGWWLG

401 RVEAFAVLF*
```

SEQ ID NO:7 cDNA Sequence that Codes for LXRα-42e−

```
   1 atgtccttgt ggctgggggc ccctgtgcct gacattcctc ctgactctgc 51 ggtggagctg tggaagccag gcgcacagga tgcaagcagc caggcccagg 101 gaggcagcag ctgcatcctc agagaggaag ccaggatgcc ccactctgct 151 ggggtactg cagggtggg gctggaggct gcagagccca cagccctgct 201 caccagggca gagccccctt cagaacccac agagatccgt ccacaaaagc 251 ggaaaaaggg gccagccccc aaaatgctgg ggaacgagct atgcagcgtg 301 tgtggggaca aggcctcggg cttccactac aatgttctga gctgcgaggg 351 ctgcaaggga ttcttccgcc gcagcgtcat caagggagcg cactacatct 401 gccacagtgg cggccactgc cccatggaca cctacatgcg tcgcaagtgc 451 caggagtgtc ggcttcgcaa atgccgtcag gctggcatgc gggaggagtg 501 tgtcctgtca aagaacagat ccgcctgaa gaaactgaag cggcaagagg 551 aggaacaggc tcatgccaca tccttgcccc ccaggcgttc ctcaccccc 601 caaatcctgc cccagctcag cccggaacaa ctgggcatga tcgagaagct 651 cgtcgctgcc cagcaacagt gtaaccggcg ctccttttct gaccggcttc 701 gagtcacggt gatgcttctg gagacatctc ggaggtacaa ccctgggagt 751 gagagtatca ccttcctcaa ggatttcagt tataaccggg aagactttgc 801 caaagcaggg ctgcaagtgg aattcatcaa ccccatcttc gagttctcca 851 gggccatgaa tgagctgcaa ctcaatgatg ccgagtttgc cttgctcatt 901 gctatcagca tcttctctgc aggtgtggag gagggcaat gggaaacagc 951 aagagactta caccaaggag ggctgcaggt cccacaggaa tcggtggggg 1001 gaggggggtg gtggcttggg agggtggagg catttgctgt gttattttag
```

SEQ ID NO:8

Deduced Amino Acid Sequence of LXRα-42e⁻

```
  1 MSLWLGAPVP DIPPDSAVEL WKPGAQDASS QAQGGSSCIL REEARMPHSA
 51 GGTAGVGLEA AEPTALLTRA EPPSEPTEIR PQKRKKGPAP KMLGNELCSV
101 CGDKASGFHY NVLSCEGCKG FFRRSVIKGA HYICHSGGHC PMDTYMRRKC
151 QECRLRKCRQ AGMREECVLS EEQIRLKKLK RQEEEQAHAT SLPPRRSSPP
201 QILPQLSPEQ LGMIEKLVAA QQQCNRRSFS DRLRVTVMLL ETSRRYNPGS
251 ESITFLKDFS YNREDFAKAG LQVEFINPIF EFSRAMNELQ LNDAEFALLI
301 AISIFSAGVE EGQWETARDL HQGGLQVPQE SVGGGGWWLG RVEAFAVLF*
```

SEQ ID NO:9

The Nucleotide Sequence of the Forward Primer, LXRα-For

```
5'-CGGTCGACATGTCCTTGTGGCTGGGG
```

SEQ ID NO:10

The Nucleotide Sequence of the Reverse Primer, LXRα-Rev

```
5'-CAGCGGCCGCTTCGTGCACATCCCAGATCTC
```

SEQ ID NO:11

The Nucleotide Sequence of the Forward Primer, L64-For

```
5'-TGGGAAGCAGGGATGAGG-3'
```

SEQ ID NO:12

The Nucleotide Sequence of the Reverse Primer, L64-Rev

```
5'-GAGGGCTGGTCTTGGAGCA-3'
```

SEQ ID NO:13

The Nucleotide Sequence of the L64 TaqMan Probe

```
FAM-TCGGCCTCCCTGGAAGAGGCC-TAMRA
```

SEQ ID NO:14

Part of LXRα Promoter Sequence; Used for the Luciferase Assay Referred to in Example 6

```
  1 tgggaactgg agttcatagc aaaacaggaa gagccggtga gcaggaaact
 51 gggaatgggg caggggtga atgaccagca gtaaccctcag cagcttgcct
101 cccacatctg gactggagca tctgcagggt tctcagcctc tccctgtag
151 cccaccagcc ctggctgctt ccattacagc acttcactgg cccaagacgc
201 aacaagacaa gattgtcctg gactctgaca cagcaaaggg actggagtga
251 ggacatctgg gttctgatcc cagcccagcc actaactgtg tggtcttgga
```

SEQ ID NO:15

The Nucleotide Sequence of the LXR Response Element (LXRE)

```
5'-AGGTCAnnnnAGGTCA-3'
```

SEQ ID NO:16

The Unique Nucleotide Sequence of the LXRα-64 Variant that Forms a New, Larger Exon 6 and Connects Exons 6 and 7 of Wild Type LXRα

```
GCTGGAGAAG   GGCAAGGGAT   GAAGGGAGAA   GCAGAGTGGG
ATTATCTGTG   GGAGGGGCCT   CCAGACATCG   AGCTGGGAGA
GCCAAATCTG   CTGGGAAGCA   GGGATGAGGA   GAATCGGCCT
CCCTGGAAGA   GGCCATGCTC   CAAGACCAGC   CCTCCTAGTC
CCCGTTTGAG   GTTTGCTGCT   TGTGTGCAGG   TG
```

SEQ ID NO:17

The Deduced Amino Acid Sequence Encoded by SEQ ID NO:16

```
VAGEGQGMKGEAEWDYLWEGPPDIELGEPNLLGS
RDEENRPPWKRPCSKTSPPSPRLRFAACVQ
```

SEQ ID NO:18

The Unique Nucleotide Sequence of LXRα-42e that Forms a New Exon 8 that Includes Exon 8 of Wild Type LXRα and Creates a Longer Exon 8 LXRα-42 Variant.

```
GTGTGGAGGA  GGGGCAATGG  GAAACAGCAA  GAGACTTACA
CCAAGGAGGG  CTGCAGGTCC  CACAGGAATC  GGTGGGGGGA
GGGGGGTGGT  GGCTTGGGAG  GGTGGAGGCA  TTTGCTGTGT
TATTTTAGGA  TGAGAGAGCT  TGGCTGGAGC  ATGTCTCTAT
ATTTTGGTTG  CAATTTGGGG  TATGGAACTG  GACCCTGGCC
AGACCTGCTC  CTCAACTCTC  TTGGTGACCT  ATAG
```

SEQ ID NO:19

The Deduced Amino Acid Sequence Encoded by SEQ ID NO:18

```
GVEEGQWETARDLHQGGLQVPQESVGGGGWWLGRVEAFAVLF
```

SEQ ID NO:20

The Nucleotide Sequence of the LXR Response Element (LXRE) in LXRα Promoters

```
5'-TGACCAgcagTAACCT-3'
```

SEQ ID NO:21

The Nucleotide Sequence of L42-For

```
5'-GGTGGAGGCATTTGCTGTGT-3'
```

SEQ ID NO:22

The Nucleotide Sequence of L42-Rev

```
5'-CCCAAATTGCAACCAAAATATAGA-3'
```

SEQ ID NO:23

The Nucleotide Sequence of L42 Probe

```
FAM-TTTAGGATGAGAGAGCTTGGCTGGAGCAT-TAMRA
```

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a human liver X receptor alpha (LXRα) variant polypeptide or a complement of an isolated nucleic acid molecule encoding an LXRα variant polypeptide selected from the group consisting of:
   (a) an isolated nucleic acid molecule encoding SEQ ID NO:4, wherein the isolated nucleic acid molecule encodes a polypeptide that has LXR-responsive pathway activity; and
   (b) an isolated nucleic acid molecule that fully is complementary to the isolated nucleic acid of (a).

2. An isolated nucleic acid molecule consisting of SEQ ID NO:3, wherein the isolated nucleic acid molecule encodes a polypeptide that has LXR-responsive pathway activity.

3. The isolated nucleic acid molecule of claim 1, wherein the isolated nucleic acid molecule is a DNA molecule.

4. The isolated nucleic acid molecule of claim 1, wherein the isolated nucleic acid molecule is an RNA molecule.

5. The isolated nucleic acid molecule of claim 1(a), wherein the isolated nucleic acid molecule comprises SEQ ID NO:3.

6. The nucleic acid molecule of claim 1, wherein the polypeptide encoded by the isolated nucleic acid molecule can form a dimer with a wild-type LXRα.

7. The nucleic acid molecule of claim 1, wherein the polypeptide encoded by the isolated nucleic acid molecule can form a heterodimer with a retinoid X receptor (RXR).

8. The nucleic acid molecule of claim 7, wherein the RXR is an RXRα, RXRβ, or RXRγ.

9. A construct comprising an isolated nucleic acid molecule of claim 1.

10. The construct of claim 9, wherein the isolated nucleic acid molecule is operatively linked to a regulatory sequence.

11. The construct of claim 9, wherein the construct is a plasmid.

12. The construct of claim 9, wherein the construct comprises pCMV/myc or pcDNA 3.1, or is a derivative thereof.

13. A host cell comprising an isolated nucleic acid molecule of claim 1.

14. An isolated host cell comprising the construct of claim 9.

15. The host cell of claim 13, wherein the host cell is a prokaryotic cell.

16. The host cell of claim 13, wherein the host cell is an *E. coli*.

17. The host cell of claim 13, wherein the host cell is a mammalian cell.

18. The host cell of claim 13, wherein the host cell is a human cell.

19. The host cell of claim 13, wherein the host cell is an isolated human embryonic cell.

20. The host cell of claim 13, wherein the host cell is selected from the group consisting of a human hepatoma cell (HepG2), a Chinese hamster ovary cell (CHO), a monkey COS-1 cell, and a human embryonic kidney cell (HEK 293).

21. The host cell of claim 13, wherein, the host cell is selected from the group consisting of a *Saccharomyces cerevisiae* cell, a *Schizosaccharomyces pombe* cell, and a *Pichia pastoris* cell.

* * * * *